(12) United States Patent
Garofalo et al.

(10) Patent No.: US 10,702,305 B2
(45) Date of Patent: Jul. 7, 2020

(54) OPERATIVE CANNULAS AND RELATED METHODS

(71) Applicant: CooperSurgical, Inc., Trumbull, CT (US)

(72) Inventors: Rosemary Michelle Garofalo, North Haven, CT (US); Russell Heinrich, Guilford, CT (US); Thomas William Winegar, Trumbull, CT (US)

(73) Assignee: CooperSurgical, Inc., Trumbull, CT (US)

( * ) Notice: Subject to any disclaimer, the term of this patent is extended or adjusted under 35 U.S.C. 154(b) by 232 days.

(21) Appl. No.: 15/416,360

(22) Filed: Jan. 26, 2017

(65) Prior Publication Data

US 2017/0273716 A1    Sep. 28, 2017

Related U.S. Application Data

(60) Provisional application No. 62/311,947, filed on Mar. 23, 2016, provisional application No. 62/364,008, filed on Jul. 19, 2016, provisional application No. 62/393,827, filed on Sep. 13, 2016.

(51) Int. Cl.
*A61B 17/34* (2006.01)
*A61B 1/00* (2006.01)
*A61B 1/307* (2006.01)
*A61B 17/00* (2006.01)
(Continued)

(52) U.S. Cl.
CPC ........ *A61B 17/3423* (2013.01); *A61B 1/0014* (2013.01); *A61B 1/00135* (2013.01); *A61B 1/307* (2013.01); *A61B 17/3439* (2013.01); *A61B 17/29* (2013.01); *A61B 2017/0023* (2013.01); *A61B 2017/0042* (2013.01); *A61B 2017/345* (2013.01); *A61B 2017/347* (2013.01);
(Continued)

(58) Field of Classification Search
CPC ............ A61B 17/3423; A61B 17/0218; A61B 17/4241; A61B 1/307; A61M 29/00
USPC .................................. 600/184–199, 201–249
See application file for complete search history.

(56) References Cited

U.S. PATENT DOCUMENTS

| 4,201,199 A | 5/1980 | Smith |
| 4,441,509 A | 4/1984 | Kotsifas et al. |
| 4,475,539 A | 10/1984 | Konomura |

(Continued)

FOREIGN PATENT DOCUMENTS

| CN | 2565407 | 8/2003 | ............. A61B 17/42 |
| CN | 2638669 | 9/2004 | ............. A61B 1/313 |

(Continued)

OTHER PUBLICATIONS

U.S. Appl. No. 12/911,297, filed Oct. 25, 2010, Ouyang.

(Continued)

*Primary Examiner* — Si Ming Ku
(74) *Attorney, Agent, or Firm* — Fish & Richardson P.C.

(57) ABSTRACT

An operative cannula includes an elongate shaft that includes a wall structure and a channel extending along the wall structure. The wall structure defines an interior pocket sized to receive a tubular member and is configured to grasp the tubular member when the tubular member is disposed within the interior pocket. The channel is configured to allow passage of an instrument from a proximal end region of the elongate shaft through a distal end region of the elongate shaft.

22 Claims, 34 Drawing Sheets

(51) Int. Cl.
*A61B 17/29* (2006.01)
*A61B 17/42* (2006.01)

(52) U.S. Cl.
CPC ............... *A61B 2017/3447* (2013.01); *A61B 2017/4216* (2013.01)

(56) References Cited

U.S. PATENT DOCUMENTS

| | | | |
|---|---|---|---|
| 4,836,189 | A | 6/1989 | Alfred et al. |
| 5,483,951 | A | 1/1996 | Frassica et al. |
| 5,484,422 | A | 1/1996 | Sloane et al. |
| 5,498,230 | A | 3/1996 | Adair |
| 5,506,912 | A | 4/1996 | Nagasaki et al. |
| 5,527,262 | A | 6/1996 | Monroe et al. |
| 5,591,119 | A | 1/1997 | Adair |
| 5,609,561 | A | 3/1997 | Uehara et al. |
| 5,637,074 | A | 6/1997 | Andino et al. |
| 5,662,586 | A | 9/1997 | Monroe et al. |
| 5,666,965 | A | 9/1997 | Bales et al. |
| 5,734,418 | A | 3/1998 | Danna |
| 5,751,341 | A | 5/1998 | Chaleki et al. |
| 5,823,940 | A | 10/1998 | Newman |
| 5,860,953 | A | 1/1999 | Snoke et al. |
| 5,873,816 | A | 2/1999 | Kagawa et al. |
| 5,879,289 | A | 3/1999 | Yarush et al. |
| 5,885,214 | A | 3/1999 | Monroe et al. |
| 5,902,230 | A | 5/1999 | Takahashi et al. |
| 5,929,901 | A | 7/1999 | Adair et al. |
| 5,986,693 | A | 11/1999 | Adair et al. |
| 5,993,378 | A | 11/1999 | Lemelson |
| 6,043,839 | A | 3/2000 | Adair et al. |
| 6,066,089 | A | 5/2000 | Costello et al. |
| 6,095,970 | A | 8/2000 | Hidaka et al. |
| 6,102,920 | A | 8/2000 | Sullivan et al. |
| 6,106,457 | A | 8/2000 | Perkins et al. |
| 6,152,871 | A * | 11/2000 | Foley ............... A61B 17/3421 600/114 |
| 6,203,493 | B1 | 3/2001 | Ben-Haim |
| 6,211,904 | B1 | 4/2001 | Adair et al. |
| 6,221,007 | B1 | 4/2001 | Green |
| 6,275,855 | B1 | 8/2001 | Johnson |
| 6,310,642 | B1 | 10/2001 | Adair et al. |
| 6,315,712 | B1 | 11/2001 | Rovegno |
| 6,348,035 | B1 | 2/2002 | Takami |
| 6,387,043 | B1 | 5/2002 | Yoon |
| 6,419,626 | B1 | 7/2002 | Yoon |
| 6,428,470 | B1 | 8/2002 | Thompson |
| 6,468,265 | B1 | 10/2002 | Evans et al. |
| 6,478,730 | B1 | 11/2002 | Bala et al. |
| 6,554,765 | B1 | 4/2003 | Yarushi et al. |
| 6,593,587 | B2 | 7/2003 | Pease |
| 6,652,453 | B2 | 11/2003 | Smith et al. |
| 6,709,408 | B2 | 3/2004 | Fisher |
| 6,717,166 | B2 | 4/2004 | Pease |
| 6,858,857 | B2 | 2/2005 | Pease et al. |
| 6,858,858 | B2 | 2/2005 | Pease |
| 6,923,757 | B2 | 8/2005 | Abe et al. |
| 6,929,600 | B2 | 8/2005 | Hill |
| 6,979,290 | B2 | 12/2005 | Mourlas et al. |
| 6,982,740 | B2 | 1/2006 | Adair et al. |
| 7,030,904 | B2 | 4/2006 | Adair et al. |
| 7,033,314 | B2 | 4/2006 | Kamrava et al. |
| 7,074,182 | B2 | 7/2006 | Rovegno |
| 7,081,097 | B2 | 7/2006 | Martone et al. |
| 7,099,078 | B2 | 8/2006 | Spencer |
| 7,144,250 | B2 | 12/2006 | Fischer et al. |
| 7,214,183 | B2 | 5/2007 | Miyake |
| 7,365,768 | B1 | 4/2008 | Ono et al. |
| 7,384,308 | B2 | 6/2008 | Boehnlein et al. |
| 7,431,619 | B2 | 10/2008 | Boehnlein et al. |
| 7,445,596 | B2 | 11/2008 | Kucklick et al. |
| 7,500,947 | B2 | 3/2009 | Kucklick et al. |
| 7,520,854 | B2 | 4/2009 | Sato |
| 7,530,946 | B2 | 5/2009 | Hartwick |
| 7,581,988 | B2 | 9/2009 | Boehnlein et al. |
| 7,584,534 | B2 | 9/2009 | Pease et al. |
| 7,758,495 | B2 | 7/2010 | Pease et al. |
| 7,783,133 | B2 | 8/2010 | Dunki-Jacobs et al. |
| 7,794,409 | B2 | 9/2010 | Damarati |
| 7,846,107 | B2 | 12/2010 | Hoffman et al. |
| 7,850,601 | B2 | 12/2010 | Uchimura et al. |
| 7,927,272 | B2 | 4/2011 | Bayer et al. |
| 7,946,981 | B1 | 5/2011 | Cubb |
| 7,959,561 | B2 | 6/2011 | Akui et al. |
| 7,976,459 | B2 | 7/2011 | Laser |
| 7,979,689 | B2 | 7/2011 | Watt et al. |
| 8,004,560 | B2 | 8/2011 | Sato et al. |
| 8,007,433 | B2 | 8/2011 | Iketani |
| 8,022,979 | B2 | 9/2011 | Miyamoto et al. |
| 8,025,670 | B2 | 9/2011 | Sharp et al. |
| 8,033,993 | B2 | 10/2011 | Amano et al. |
| 8,133,169 | B2 | 3/2012 | Nagase et al. |
| 8,142,346 | B2 | 3/2012 | Shoroji et al. |
| 8,144,191 | B2 | 3/2012 | Kawanishi et al. |
| 8,157,726 | B2 | 4/2012 | Melder |
| 8,177,710 | B1 | 5/2012 | Hosaka et al. |
| 8,182,416 | B1 | 5/2012 | Hosaka et al. |
| 8,189,043 | B2 | 5/2012 | Schneider et al. |
| 8,218,074 | B2 | 7/2012 | Pease et al. |
| 8,317,689 | B1 | 11/2012 | Remijan et al. |
| 8,356,527 | B2 | 1/2013 | Hudson |
| 8,382,665 | B1 | 2/2013 | Fam |
| 8,403,831 | B2 | 3/2013 | Kishioka |
| 8,416,291 | B2 | 4/2013 | Carrey et al. |
| 8,453,639 | B2 | 6/2013 | Kim et al. |
| 8,460,182 | B2 | 6/2013 | Ouyang et al. |
| 8,535,219 | B2 | 9/2013 | Smith et al. |
| 8,556,801 | B2 | 10/2013 | Liu |
| 8,574,151 | B2 | 11/2013 | Mitsuhashi |
| 8,581,971 | B2 | 11/2013 | Miyamoto et al. |
| 8,591,401 | B2 | 11/2013 | Miyayashiki et al. |
| 8,597,179 | B2 | 12/2013 | Kokubo |
| 8,638,361 | B2 | 1/2014 | Tanabe et al. |
| 8,641,605 | B2 | 2/2014 | Shoroji et al. |
| 8,656,697 | B2 | 2/2014 | Zubiate et al. |
| 8,872,906 | B2 | 10/2014 | Bayer et al. |
| 8,968,190 | B2 * | 3/2015 | Stopek ............... A61B 17/3423 600/205 |
| 2002/0077550 | A1 | 6/2002 | Rabiner et al. |
| 2003/0040659 | A1 | 2/2003 | Kazakevish |
| 2003/0195390 | A1 | 10/2003 | Graumann |
| 2004/0054254 | A1 | 3/2004 | Miyake |
| 2004/0122327 | A1 | 6/2004 | Belson et al. |
| 2004/0210161 | A1 | 10/2004 | Burdorff et al. |
| 2004/0220478 | A1 | 11/2004 | Wallace et al. |
| 2005/0075538 | A1 | 4/2005 | Banik et al. |
| 2005/0085690 | A1 | 4/2005 | Tien |
| 2005/0136372 | A1 | 6/2005 | Fischer et al. |
| 2006/0004258 | A1 | 1/2006 | Sun et al. |
| 2006/0058703 | A1 | 3/2006 | Huenerbein |
| 2006/0106281 | A1 | 5/2006 | Boulais et al. |
| 2006/0155168 | A1 | 7/2006 | Pease |
| 2006/0184187 | A1 | 8/2006 | Surti |
| 2006/0258955 | A1 | 11/2006 | Hoffman et al. |
| 2007/0030344 | A1 | 2/2007 | Miyamoto et al. |
| 2007/0033626 | A1 | 2/2007 | Yang et al. |
| 2007/0038020 | A1 | 2/2007 | Tien |
| 2007/0129604 | A1 | 6/2007 | Hatcher et al. |
| 2007/0167681 | A1 | 7/2007 | Gill et al. |
| 2007/0185379 | A1 | 8/2007 | Newman et al. |
| 2007/0225556 | A1 | 9/2007 | Ortiz et al. |
| 2007/0225561 | A1 | 9/2007 | Watanabe et al. |
| 2007/0249904 | A1 | 10/2007 | Amano et al. |
| 2007/0265492 | A1 | 11/2007 | Sonnenschein et al. |
| 2008/0042861 | A1 | 2/2008 | Dacquay et al. |
| 2008/0045791 | A1 | 2/2008 | Gal et al. |
| 2008/0051628 | A1 | 2/2008 | Pecherer et al. |
| 2008/0058591 | A1 | 3/2008 | Saadat et al. |
| 2008/0058595 | A1 | 3/2008 | Snoke et al. |
| 2008/0076966 | A1 | 3/2008 | Isaacson |
| 2008/0097469 | A1 | 4/2008 | Gruber et al. |
| 2008/0097470 | A1 | 4/2008 | Gruber et al. |
| 2008/0108869 | A1 | 5/2008 | Sanders et al. |
| 2008/0132763 | A1 | 6/2008 | Isaacson |

(56) References Cited

U.S. PATENT DOCUMENTS

| | | |
|---|---|---|
| 2008/0195128 A1 | 8/2008 | Orbay et al. |
| 2008/0200758 A1 | 8/2008 | Orbay et al. |
| 2008/0243031 A1 | 10/2008 | Seibel et al. |
| 2009/0030276 A1 | 1/2009 | Saadat et al. |
| 2009/0082695 A1 | 3/2009 | Whitehead |
| 2009/0105538 A1 | 4/2009 | Van Dam et al. |
| 2009/0112058 A1 | 4/2009 | Kagawa |
| 2009/0118575 A1 | 5/2009 | Ichikawa et al. |
| 2009/0118580 A1 | 5/2009 | Sun et al. |
| 2009/0167849 A1 | 7/2009 | Niida |
| 2009/0196459 A1 | 8/2009 | Watt et al. |
| 2009/0221873 A1 | 9/2009 | McGrath |
| 2009/0225159 A1 | 9/2009 | Schneider et al. |
| 2009/0231419 A1 | 9/2009 | Bayer |
| 2009/0318758 A1 | 12/2009 | Farr et al. |
| 2010/0022824 A1 | 1/2010 | Cybulski |
| 2010/0030020 A1 | 2/2010 | Sanders et al. |
| 2010/0033563 A1 | 2/2010 | Boehnlein et al. |
| 2010/0033986 A1 | 2/2010 | Schober et al. |
| 2010/0121139 A1 | 5/2010 | Ouyang et al. |
| 2010/0121142 A1 | 5/2010 | Ouyang et al. |
| 2010/0121155 A1 | 5/2010 | Ouyang et al. |
| 2010/0128116 A1 | 5/2010 | Sato et al. |
| 2010/0185052 A1 | 7/2010 | Chang |
| 2010/0191050 A1 | 7/2010 | Zwolinski |
| 2010/0238278 A1 | 9/2010 | Rovegno |
| 2010/0262000 A1 | 10/2010 | Wallace et al. |
| 2010/0284580 A1 | 11/2010 | Ouyang et al. |
| 2010/0286477 A1 | 11/2010 | Ouyang et al. |
| 2011/0009694 A1 | 1/2011 | Schultz et al. |
| 2011/0034773 A1 | 2/2011 | Ishigami et al. |
| 2011/0090331 A1 | 4/2011 | Draper |
| 2011/0092842 A1 | 4/2011 | Decaria et al. |
| 2011/0112360 A1 | 5/2011 | Swann et al. |
| 2011/0112361 A1 | 5/2011 | Ishigami et al. |
| 2011/0130627 A1 | 6/2011 | McGrail et al. |
| 2011/0130632 A1 | 6/2011 | McGrail et al. |
| 2011/0137127 A1 | 6/2011 | Schwartz et al. |
| 2011/0160537 A1 | 6/2011 | Chen |
| 2011/0201884 A1 | 8/2011 | Kishioka |
| 2011/0218457 A1 | 9/2011 | Song et al. |
| 2011/0270038 A1 | 11/2011 | Jiang et al. |
| 2011/0270179 A1 | 11/2011 | Ouyang et al. |
| 2011/0273556 A1 | 11/2011 | Lyons et al. |
| 2012/0095458 A1 | 4/2012 | Cybulski |
| 2012/0099735 A1 | 4/2012 | Chen |
| 2012/0100729 A1 | 4/2012 | Ouyang et al. |
| 2012/0116160 A1 | 5/2012 | Nieman et al. |
| 2012/0130160 A1 | 5/2012 | Bonye |
| 2012/0209065 A1 | 8/2012 | Hosaka et al. |
| 2012/0209066 A1 | 8/2012 | Hosaka et al. |
| 2012/0209067 A1 | 8/2012 | Hosaka et al. |
| 2012/0265009 A1 | 10/2012 | Ouyang et al. |
| 2012/0277528 A1 | 11/2012 | Qiao |
| 2012/0289778 A1 | 11/2012 | Chan |
| 2012/0310045 A1 | 12/2012 | Hu et al. |
| 2012/0323073 A1 | 12/2012 | Azuma et al. |
| 2013/0041220 A1 | 2/2013 | Kutsuma |
| 2013/0046316 A1 | 2/2013 | Sullivan et al. |
| 2013/0050455 A1 | 2/2013 | Yagi |
| 2013/0066151 A1 | 3/2013 | Chen |
| 2013/0066152 A1 | 3/2013 | Chen |
| 2013/0072754 A1 | 3/2013 | Okamoto et al. |
| 2013/0079594 A1 | 3/2013 | Motoki |
| 2013/0096376 A1 | 4/2013 | Takei et al. |
| 2013/0225924 A1 | 8/2013 | Simms et al. |
| 2013/0231533 A1 | 9/2013 | Papademetriou et al. |
| 2013/0244453 A1 | 9/2013 | Sakamoto |
| 2013/0253368 A1 | 9/2013 | Are et al. |
| 2013/0289347 A1 | 10/2013 | Ito et al. |
| 2013/0296648 A1 | 11/2013 | Ouyang et al. |
| 2013/0303846 A1 | 11/2013 | Cybulski |
| 2013/0345503 A1 | 12/2013 | Friedrich |
| 2013/0345518 A1 | 12/2013 | Law et al. |
| 2014/0031621 A1 | 1/2014 | Liu |
| 2014/0039253 A1 | 2/2014 | Fang et al. |
| 2014/0039264 A1* | 2/2014 | Heiman ............ A61B 5/04001 600/202 |
| 2014/0073853 A1 | 3/2014 | Swisher et al. |
| 2014/0276207 A1 | 9/2014 | Ouyang et al. |
| 2014/0288460 A1 | 9/2014 | Ouyang et al. |
| 2014/0316207 A1* | 10/2014 | Hain ................. A61B 1/00073 600/194 |
| 2015/0099933 A1* | 4/2015 | Schwartz .......... A61M 16/0488 600/186 |
| 2015/0190128 A1* | 7/2015 | Fenn ..................... A61B 1/018 600/202 |
| 2016/0174819 A1 | 6/2016 | Ouyang et al. |

FOREIGN PATENT DOCUMENTS

| | | | |
|---|---|---|---|
| CN | 2754555 | 2/2006 | ............ A61B 1/313 |
| CN | 1924779 | 3/2007 | ............ G06F 3/048 |
| CN | 101422351 | 5/2009 | ............ A61B 1/00 |
| CN | 201282962 | 8/2009 | ............ A61B 1/05 |
| CN | 201641951 | 11/2010 | ............ A61B 1/07 |
| CN | 201658404 | 12/2010 | ............ A61B 17/42 |
| CN | 201701193 | 1/2011 | ............ A61B 1/05 |
| JP | 10-508240 | 8/1998 | ............ A61B 10/00 |
| JP | 2003-88499 | 3/2003 | ............ A61B 1/04 |
| JP | 2007-252559 | 10/2007 | ............ A61B 1/00 |
| JP | 2010-506669 | 3/2010 | ............ A61B 1/04 |
| WO | WO 1994/008512 | 4/1994 | ............ A61B 10/00 |
| WO | WO 2001/029817 | 4/2001 | ............ G09G 5/20 |
| WO | WO 2008/048688 | 4/2008 | ............ A61B 1/303 |
| WO | WO 2009/150231 | 12/2009 | ............ A61B 5/00 |
| WO | WO 2010/011781 | 1/2010 | ............ A61B 17/00 |
| WO | WO 2011/006052 | 1/2011 | ............ A61B 1/05 |
| WO | WO 2011/038310 | 3/2011 | ............ A61B 1/04 |
| WO | WO 2012/060932 | 5/2012 | ............ A61B 1/00 |
| WO | WO 2012/151073 | 11/2012 | ............ A61B 1/018 |
| WO | WO 2014/031192 | 2/2014 | ............ A61B 1/00 |
| WO | WO 2014/065901 | 5/2014 | ............ A61B 1/00 |

OTHER PUBLICATIONS

International Search Report for International Application No. PCT/US13/40992, dated Oct. 17, 2013 (3 pages).
International Search Report for International Application No. PCT/US13/49074, dated Oct. 1, 2013 (1 page).
EndoSee Corporation Brochure, www.endosee.com, Apr. 2013, 2 pages.
Ethicon Versascope Brochure VS001R2, S/06, 6 pages.
VeraStep Bladeless Trocars, Covidien Catalog, 2015 (2 pages).
Ethicon Corporation Brochure, Gynecare Versascope Hysteroscopy System, http://www.normedi.com/images/download/BR911_Versascope.pdf, 2013 (6 pages).
Ethicon Gynecare Versascope™ Hysteroscopy System, http://gb.ethicon.com/healthcare-professionals/products/gynaecology-solutions/gynecare-versascope-hysteroscopy-system, 2016 (3 pages).

* cited by examiner

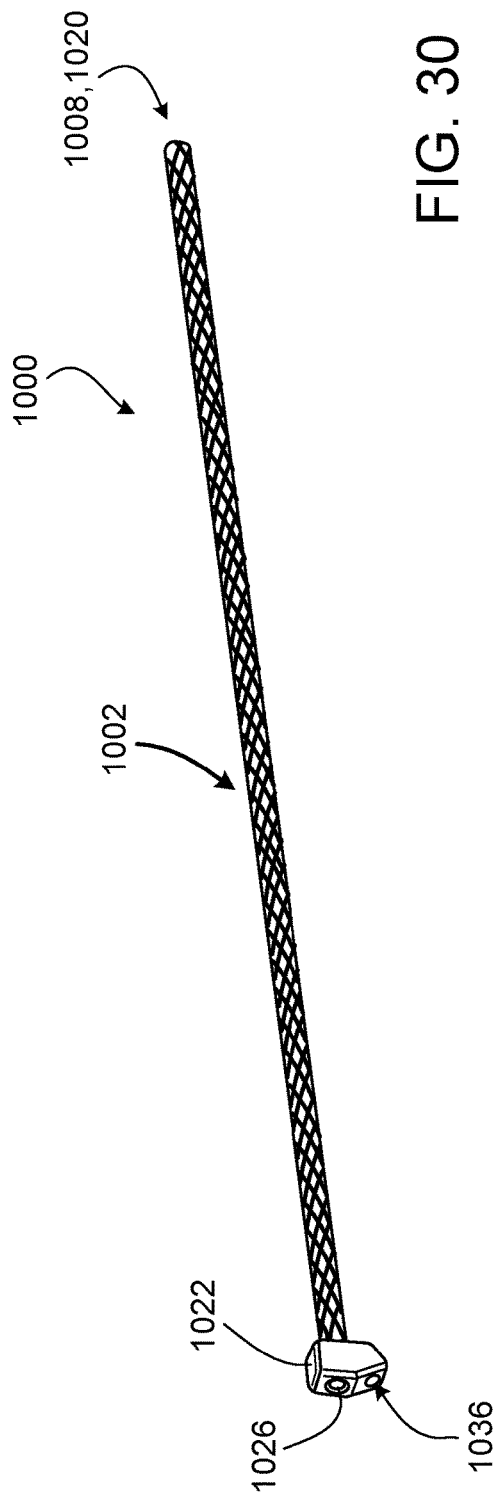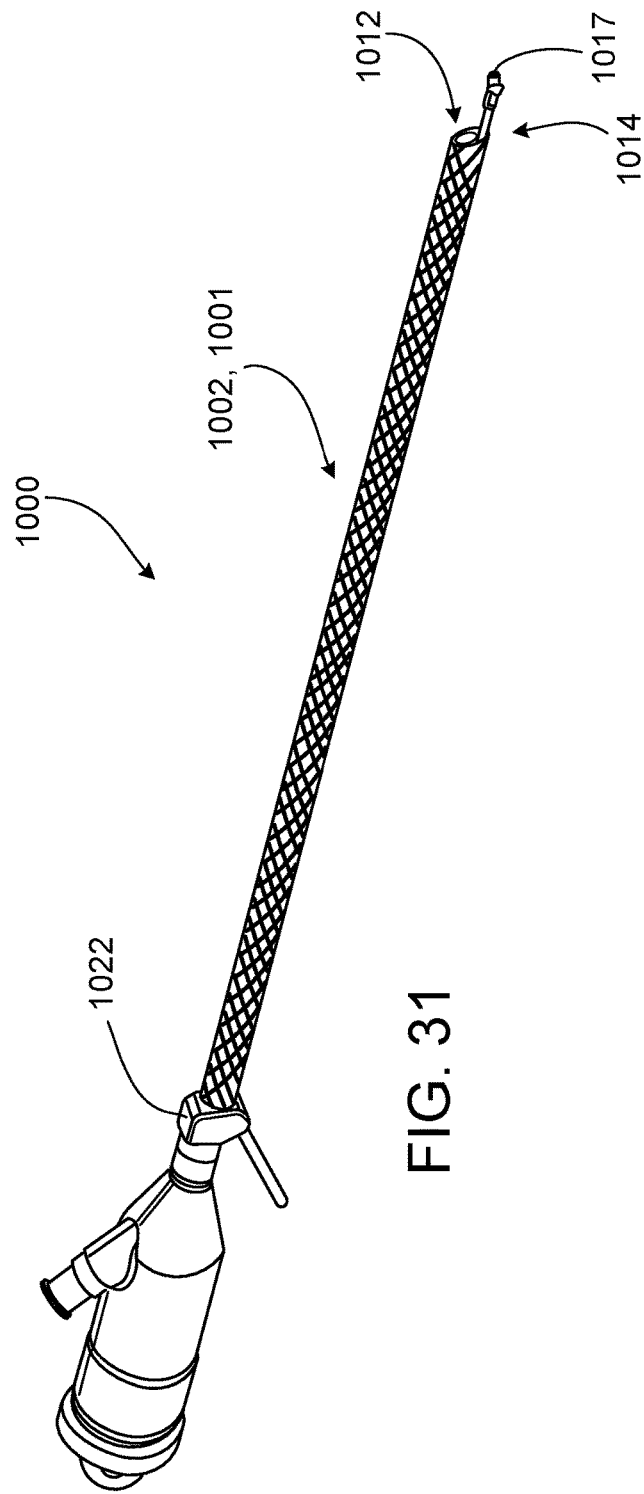

OPERATIVE CANNULAS AND RELATED METHODS

CROSS-REFERENCE TO RELATED APPLICATIONS

This application claims priority to U.S. Provisional Patent Application No. 62/311,947, filed on Mar. 23, 2016, U.S. Provisional Patent Application No. 62/364,008, filed on Jul. 19, 2016, and U.S. Provisional Patent Application No. 62/393,827, filed on Sep. 13, 2016, the entire contents of which are incorporated herein by reference.

TECHNICAL FIELD

This disclosure relates to operative cannulas and related methods.

BACKGROUND

Endoscopic cannulas (e.g., cannulas of hysteroscopes) can be used to view a uterine cavity of a patient for diagnosing uterine pathologies and other abnormalities, such as endometriosis, uterine fibroids (e.g., myomas), uterine polyps, intrauterine cancer, lesions, adhesions, and hyperplasias. For example, an endoscopic cannula including an integral working channel can be inserted through a cervix of the patient and into the uterine cavity, where the endoscopic cannula may visualize an abnormality, another anatomical feature of interest, or a foreign body within the uterine cavity. In cases where an intervention (e.g., a device retrieval or an operation, such as a biopsy procedure, a polypectomy, an excision, or a cautery) is required for further diagnosis or for treatment, a surgical instrument may be inserted through the working channel of the endoscopic cannula and into the uterine cavity to perform the intervention. Following completion of the intervention and removal of the endoscopic cannula and the surgical instrument from the patient, the endoscopic cannula can be disinfected according to standard protocols for reuse in another endoscopic procedure.

SUMMARY

In general, this disclosure relates to disposable operative cannulas and related methods. Such operative cannulas can be used to perform an intervention (e.g., an operation, a device retrieval, or another procedure) within a body cavity (e.g., a uterine cavity) of a patient.

In one aspect, an operative cannula includes an elongate shaft that includes a wall structure and a channel extending along the wall structure. The wall structure defines an interior pocket sized to receive a tubular member and is configured to grasp the tubular member when the tubular member is disposed within the interior pocket. The channel is configured to allow passage of an instrument from a proximal end region of the elongate shaft through a distal end region of the elongate shaft.

Embodiments may include one or more of the following features.

In some embodiments, the wall structure includes two wall portions that define an exterior opening of the elongate shaft, the exterior opening having a width that is smaller than a diameter of the tubular member.

In certain embodiments, the two wall portions are configured to be urged apart to widen the exterior opening.

In some embodiments, each of the two wall portions defines multiple slots.

In certain embodiments, the elongate shaft is deformable such that the elongate shaft can assume a curvature of the tubular member when the tubular member is disposed within the interior pocket of the elongate shaft and the elongate shaft is moved along the tubular member.

In some embodiments, the elongate shaft is made of one or more materials having a hardness in a range of about 0 Shore A to about 100 Shore A.

In certain embodiments, the elongate shaft is made of one or more materials having a hardness in a range of about 5 Shore D to about 95 Shore D.

In some embodiments, the elongate shaft is rigid such that the tubular member assumes a profile of the wall structure of the elongate shaft when the tubular member is disposed within the interior pocket of the elongate shaft and the elongate shaft is moved along the tubular member.

In certain embodiments, the wall structure is a coiled wall.

In some embodiments, the coiled wall is configured to be urged apart to provide an entryway to the interior pocket.

In certain embodiments, the channel has a beveled distal end that defines a channel opening.

In some embodiments, the channel opening has an area that is greater than a cross-sectional area of the channel.

In certain embodiments, the channel is located adjacent to the interior pocket.

In some embodiments, the operative cannula further includes a handle portion extending from the proximal end region of the elongate shaft.

In certain embodiments, the handle portion is a clip.

In some embodiments, the operative cannula further includes an entry port extending laterally from the channel.

In certain embodiments, the elongate shaft is sized to be inserted through a cervix of a patient.

In some embodiments, the instrument is a surgical device.

In certain embodiments, the operative cannula is a single-use device.

In some embodiments, the operative cannula is configured to facilitate a medical intervention within a body cavity of a patient.

In certain embodiments, the operative cannula further includes a guide that surrounds the elongate shaft.

In some embodiments, the elongate shaft is slidable axially with respect to the guide.

In certain embodiments, the guide includes a recess formed complementary to a proximal portion of the elongate shaft.

In some embodiments, the guide includes a support member that surrounds the channel.

In certain embodiments, the guide includes a locking feature positioned along a proximal portion of the guide, the locking feature being configured to engage a corresponding feature positioned along a proximal portion of the tubular member to secure the operative cannula to the tubular member.

In some embodiments, the channel includes a fabric.

In certain embodiments, the fabric is a medical grade yarn.

In some embodiments, the channel includes multiple openings arranged in a pattern along the channel.

In certain embodiments, the channel includes a rigid portion adjacent the fabric.

In some embodiments, the channel is radially expandable.

In another aspect, a method of using an operative cannula includes placing a tubular member into an interior pocket defined by a wall structure of an elongate shaft of the operative cannula, passing an instrument through a channel extending along the wall structure of the elongate shaft until the instrument exits the channel at a distal end region of the elongate shaft into a body cavity of a patient, and performing an intervention in the body cavity of the patient using the instrument.

Embodiments may include one or more of the following features.

In some embodiments, placing the tubular member into the interior pocket includes clipping the operative cannula onto a proximal portion of the tubular member.

In certain embodiments, placing the tubular member into the interior pocket includes urging the tubular member through an exterior opening defined by two wall portions of the wall structure, the exterior opening having a width that is smaller than a diameter of the tubular member.

In some embodiments, the two wall portions are configured to be urged apart to widen the exterior opening.

In certain embodiments, each of the two wall portions defines multiple slots.

In some embodiments, the method further includes moving the elongate shaft distally until the distal end region of the elongate shaft is positioned along a distal portion of the tubular member.

In certain embodiments, the elongate shaft is deformable such that the elongate shaft assumes a curvature of the tubular member as the elongate shaft is moved along the tubular member.

In some embodiments, the elongate shaft is made of one or more materials having a hardness in a range of about 0 Shore A to about 100 Shore A.

In certain embodiments, the elongate shaft is made of one or more materials having a hardness in a range of about 5 Shore D to about 95 Shore D.

In some embodiments, the elongate shaft is rigid such that the tubular member assumes a profile of the wall structure of the elongate shaft as the elongate shaft is moved along the tubular member.

In certain embodiments, the wall structure is a coiled wall.

In some embodiments, the coiled wall is configured to be urged apart to provide an entryway to the interior pocket.

In certain embodiments, the channel has a beveled distal end that defines a channel opening.

In some embodiments, the channel opening has an area that is greater than a cross-sectional area of the channel.

In certain embodiments, the channel is located adjacent to the interior pocket.

In some embodiments, the operative cannula includes a handle portion extending from a proximal end region of the elongate shaft.

In certain embodiments, the handle portion is a clip.

In some embodiments, the method further includes squeezing the clip to widen the wall structure of the elongate shaft.

In certain embodiments, the method further includes inserting the instrument into an entry port extending laterally from the channel.

In some embodiments, the method further includes withdrawing the instrument from the channel.

In certain embodiments, the method further includes moving the elongate shaft proximally until the operative cannula is positioned along the proximal portion of the tubular member.

In some embodiments, the method further includes removing the operative cannula from the tubular member.

In certain embodiments, the elongate shaft is sized to be inserted through a cervix of the patient.

In some embodiments, the instrument is a surgical device.

In certain embodiments, the method further includes disposing of the operative cannula after performing the operation.

In some embodiments, the method further includes attaching a guide of the operative cannula to the tubular member, the guide surrounding the elongate shaft.

In certain embodiments, the method further includes attaching the guide to a proximal portion of the tubular member.

In some embodiments, the method further includes moving the elongate shaft distally with respect to the guide until a proximal member extending from the elongate shaft abuts a distal component of the guide.

In certain embodiments, the distal component surrounds the channel.

In some embodiments, the method further includes moving the elongate shaft proximally with respect to the guide until a proximal member extending from the elongate shaft abuts a proximal structure of the guide.

In certain embodiments, the proximal structure includes a recess.

In some embodiments, the guide includes a locking feature positioned along a proximal portion of the guide, the locking feature being configured to engage a corresponding feature positioned along a proximal portion of the tubular member to secure the operative cannula to the tubular member.

In certain embodiments, the channel includes a fabric.

In some embodiments, the channel includes multiple openings arranged in a pattern along the channel.

In certain embodiments, the channel is radially expandable.

In some embodiments, the wall structure includes a fabric.

In certain embodiments, the fabric is a medical grade yarn.

In some embodiments, the fabric is formed as a braided structure.

In certain embodiments, the wall structure is radially expandable.

In some embodiments, the method further includes inserting the instrument into an entry port leading to the channel.

In certain embodiments, the method further includes inserting the tubular member into an entry port leading to the interior pocket.

In another aspect, an operative cannula includes an elongate shaft including a wall structure configured to slide onto a tubular member, the wall structure defining an interior pocket sized to receive the tubular member. The operative cannula further includes a channel extending along the interior pocket and configured to allow passage of an instrument from a proximal end of the elongate shaft through a distal end of the elongate shaft.

Embodiments may include one or more of the following features.

In some embodiments, the wall structure is a tube.

In certain embodiments, the channel includes two wall portions that define an exterior opening along the elongate shaft.

In some embodiments, the two wall portions are configured to be urged apart to widen the exterior opening.

In certain embodiments, the wall structure is formed as a flexible clamshell.

In some embodiments, the channel is located internal to the wall structure and adjacent the interior pocket.

In certain embodiments, the wall structure is configured to be urged apart along an exterior opening of the elongate shaft.

In some embodiments, the operative cannula further includes a flexible sheath surrounding the elongate structure.

In certain embodiments, the elongate shaft is deformable such that the elongate shaft can assume a curvature of the tubular member when the tubular member is disposed within the interior pocket of the elongate shaft and the elongate shaft is moved along the tubular member.

In some embodiments, the elongate shaft is made of one or more materials having a hardness in a range of about 0 Shore A to about 100 Shore A.

In certain embodiments, the elongate shaft is made of one or more materials having a hardness in a range of about 5 Shore D to about 95 Shore D.

In some embodiments, the channel includes a beveled distal end that defines a channel opening.

In certain embodiments, the channel opening has an area that is greater than a cross-sectional area of the channel.

In some embodiments, the operative cannula further includes a handle portion extending from the proximal end of the elongate shaft.

In certain embodiments, the handle portion includes a tab.

In some embodiments, the elongate shaft is sized to be inserted through a cervix of a patient.

In certain embodiments, the instrument is a surgical device.

In some embodiments, the operative cannula is a single-use device.

In certain embodiments, the operative cannula is configured to facilitate a medical intervention within a body cavity of a patient.

In another aspect, an operative cannula includes an elongate shaft configured to slide onto a tubular member. The elongate shaft is radially expandable to form an interior pocket configured to receive the tubular member and a working channel that allows passage of an instrument along the tubular member from a proximal end of the elongate shaft through a distal end of the elongate shaft. The operative cannula further includes an entry port defining a first opening that leads to the interior pocket and a second opening that leads to the working channel.

Embodiments may include one or more of the following features.

In some embodiments, the elongate shaft includes a fabric.

In certain embodiments, the fabric is a medical grade yarn.

In some embodiments, the fabric is formed as a braided structure.

In certain embodiments, the elongate shaft is deformable such that the elongate shaft can assume a curvature of the tubular member as the tubular member is passed into the elongate shaft.

In some embodiments, the elongate shaft is sized to be inserted through a cervix of a patient.

In certain embodiments, the instrument is a surgical device.

In some embodiments, the operative cannula is a single-use device.

In certain embodiments, the operative cannula is configured to facilitate a medical intervention within a body cavity of a patient.

Embodiments may provide one or more of the following advantages.

Many of the operative cannulas described herein can be releasably secured to an endoscopic cannula. This arrangement allows an intervention (e.g., operative procedure or another procedure) to be performed on a patient (e.g., by passing one or more surgical instruments through a passage of the operative cannula) without having to substitute the endoscopic cannula with an endoscopic cannula that has an integral working channel for allowing the passage of surgical instruments. For example, in cases in which an endoscopic cannula is being used for a diagnostic procedure and a clinician determines that an intervention is required, the operative cannula can simply be secured to the endoscopic cannula and delivered to a desired site. Such an arrangement can reduce the overall time and cost needed to perform a procedure.

In some embodiments, a structure of an elongate shaft (e.g., an exterior opening) of an operative cannula, together with a material choice of the operative cannula, provide the elongate shaft of the operative cannula with a flexibility that allows wall portions of the elongate shaft to spread apart (e.g., to be forced, urged, or pulled apart) to allow passage of an endoscopic cannula through the exterior opening and into an interior pocket of the elongate shaft. In this manner, the operative cannula can be easily secured to (e.g., clipped onto) the endoscopic cannula. Furthermore, the elongate shaft can be short enough in length to allow the operative cannula to be clipped onto a proximal portion of the endoscopic cannula without having to remove the endoscopic cannula from a uterine cavity of a patient.

Due to the flexibility of the elongate shaft and due to a softness of the elongate shaft, in some embodiments, the elongate shaft is also able to elastically (e.g., reversibly) deform (e.g., bend) to follow a nominal shape (e.g., a nominal curvature) of the endoscopic cannula as the operative cannula is slid along the endoscopic cannula. Accordingly, the operative cannula can advantageously be used with endoscopic cannulas having a variety of curvature profiles.

In some embodiments, due to an increased flexibility imparted by slots within the elongate shaft, the elongate shaft is able to elastically (e.g., reversibly) deform (e.g., bend) to follow the nominal shape of the endoscopic cannula as the operative cannula is slid along the endoscopic cannula, even though the operative cannula may have a relatively hard and/or a relatively highly elastic material formulation. Accordingly, the operative cannula can advantageously be used with endoscopic cannulas having a variety of curvature profiles.

In certain embodiments, although the elongate shaft is flexible enough to be spread apart for clipping onto the endoscopic cannula, the elongate shaft is also rigid enough to maintain its shape and to deform (e.g., straighten) the shape of the endoscopic cannula as the operative cannula is slid along the endoscopic cannula. Accordingly, the operative cannula may be used to perform an intervention (e.g., an operation or another procedure) using a relatively rigid surgical instrument that cannot easily adapt to the nominal shape of the endoscopic cannula as the surgical instrument is slid within a working channel of the elongate shaft. Furthermore, the rigidity of the operative cannula can allow the operative cannula to be used to steer the endoscopic cannula within the uterine cavity.

In some embodiments, the elongate shaft includes an expandable working channel. A structure of the elongate shaft (e.g., including an elongate opening extending along the working channel), together with a material choice of the elongate shaft, provides the elongate shaft with a flexibility that allows wall portions of the working channel to spread apart (e.g., to expand) to accommodate a surgical instrument that has a width greater than a nominal internal diameter of the working channel as the surgical instrument is passed into the proximal opening and through the working channel.

In some embodiments, an elongate shaft includes a working channel with a fabric section that is radially collapsible and expandable. The fabric section of the working channel may be formed as a woven fabric, a knitted fabric, a braided fabric, or a fabric with another type or structure or pattern. The fabric section of the working channel is expandable from a nominal, collapsed state in which a surgical instrument is not disposed in the working channel to a working, expanded state in which a surgical instrument is disposed within the working channel. The fabric section of the working channel can have a reduced, collapsed width that minimizes patient discomfort during insertion of the operative cannula into the patient, while having the capability to expand to accommodate surgical instruments of various widths or diameters to perform an intervention within the body cavity of the patient.

In some embodiments, an operative cannula includes a fabric elongate shaft. For example, the elongate shaft can be formed of a braided fabric that radially expands to accommodate the endoscopic cannula and further radially expands to accommodate a surgical instrument as the surgical instrument is passed through the elongate shaft along the endoscopic cannula. Such an elongate shaft defines an interior channel. In a nominal state in which the elongate shaft is not attached to the endoscopic cannula and does not carry a surgical instrument, the interior channel is collapsed to a minimal diameter and has a substantially circular cross-sectional area. In a working state in which the elongate shaft is attached to the endoscopic cannula and carries a surgical instrument, the interior channel is expanded to form an interior pocket that accommodates the endoscopic cannula and a working channel that accommodates a surgical instrument. That is, the elongate shaft can expand and collapse to snuggly accommodate a surgical instrument according to a size (e.g., a width or a diameter) of the surgical instrument. A smoothness of the elongate shaft may also ease insertion of the operative cannula through a cervix of the patient, thereby minimizing patient discomfort during use of the operative cannula.

In some embodiments, the operative cannula includes an outer sheath that snuggly surrounds the elongate shaft along a portion of its length and can expand and collapse to accommodate the elongate shaft according to a size of a surgical instrument passed through the working channel. The sheath has a stiffness that is sufficient to limit the extent to which the wall portions of the working channel can expand, thereby maintaining a mechanical integrity of the working channel (e.g., to prevent the wall portions form fracturing, tearing, or otherwise failing). Furthermore, the sheath is sufficiently soft and flexible to deform to a shape of the elongate shaft (e.g., as determined by a structural profile of the elongate shaft and as guided by the shape of the endoscopic cannula). A smoothness of the sheath and coverage of edges of the wall portions along the elongate opening may also ease insertion of the operative cannula through the cervix of the patient, thereby minimizing patient discomfort during use of the operative cannula.

In some embodiments, the elongate shaft of the operative cannula includes a coiled wall that can surround the endoscopic cannula and that makes the operative cannula less likely to pop off of the endoscopic cannula as compared to other operative cannulas that do not have coiled walls.

In some embodiments, the elongate shaft is formed as a flexible wall that can spread apart (e.g., a clamshell) to accommodate the endoscopic cannula and a surgical instrument of a variable width or diameter. A structure of such an elongate shaft (e.g., including an elongate opening extending along a length of the elongate shaft), together with a material choice of the elongate shaft, provides the elongate shaft with a flexibility that allows the elongate shaft to spread apart (e.g., to expand) to accommodate a surgical instrument that has a width greater than a nominal internal width of a working channel defined by the flexible wall as the surgical instrument is passed into an opening at an end of the flexible wall.

In some embodiments, the elongate shaft is telescopically adjustable to place the operative cannula in a retracted length configuration or in an extended length configuration. In the retracted configuration, the operative cannula is short enough in length to allow the operative cannula to be clipped onto the proximal portion of the endoscopic cannula without having to remove (e.g., withdraw) the endoscopic cannula from the patient.

In some embodiments, the elongate shaft forms a closed tubular wall such that the operative cannula can be attached to the endoscopic cannula by sliding the distal end of the endoscopic cannula into the proximal opening of the tubular wall and then advancing the endoscopic cannula until the distal portion of the endoscopic cannula is positioned at the distal opening or advancing the endoscopic cannula through a distal opening of the tubular wall until the tubular wall surrounds the endoscopic cannula along a length of the tubular wall. In this manner, the operative cannula can be easily slid onto the endoscopic cannula.

The operative cannula provides a low-cost alternative to an endoscopic cannula with an integrated working channel, which can be relatively costly to manufacture. The operative cannula also provides a low-cost operative capability to an endoscopic cannula that does not have any operative features or operative capabilities. Given that the operative cannula is packaged as a sterile, single-use device, the operative cannula can also provide a safe (e.g., uncontaminated) alternative to an endoscopic cannula with an integrated working channel, which may be susceptible to contamination if not properly sterilized between procedures. Furthermore, the disposable nature of the operative cannula can enable procedures that would otherwise be performed in a hospital to be performed in a physician's office or in a clinic, which may not have decontamination capabilities that are typically available in a hospital. Accordingly, using the operative cannula can conserve time and treatment compounds (e.g., anesthesia) and can prevent logistical inconveniences to the patient that may otherwise be associated with a procedure that would be performed in a hospital. The operative cannula can be packaged individually, and both the operative cannula and the packaging will remain sterile for a shelf-life of the operative cannula.

Other aspects, features, and advantages will be apparent from the description, the drawings, and the claims.

DESCRIPTION OF DRAWINGS

FIG. 30 is a perspective view of an operative cannula that includes a fabric elongate shaft.

FIG. 31 is a perspective view of the operative cannula of FIG. 30, carrying a surgical instrument and mounted to an endoscopic cannula.

DETAILED DESCRIPTION

Figure 1:
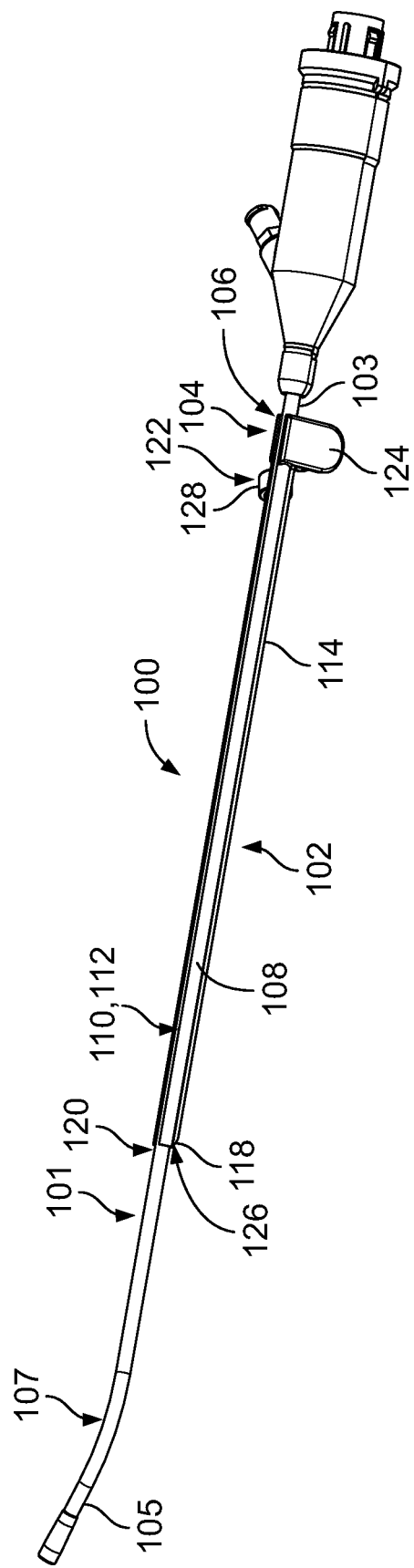
FIG. 1 is a perspective view of an operative cannula that includes bendable, separated shaft walls and that is positioned along a proximal portion of an endoscopic cannula.
Figure 2:
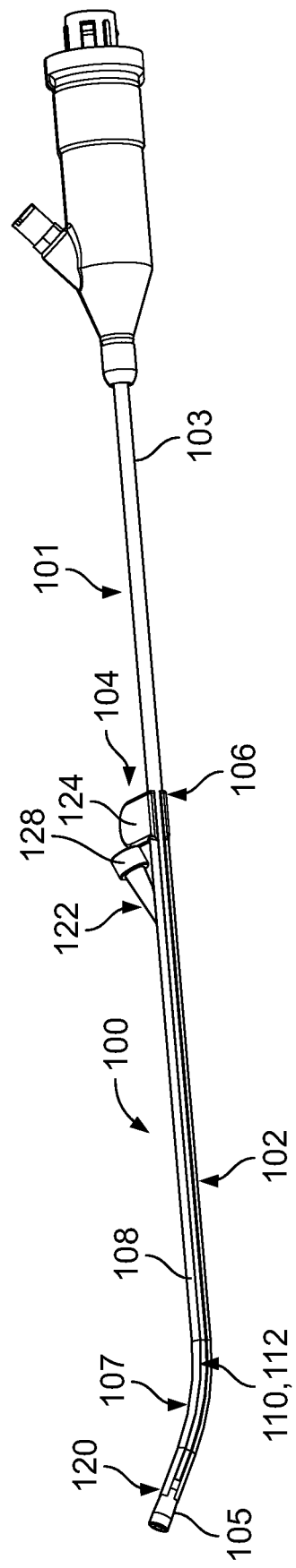
FIG. 2 is a perspective view of the operative cannula of FIG. 1 positioned along a distal portion of the endoscopic cannula of FIG. 1.

FIGS. 1 and 2 illustrate an operative cannula 100 adapted for attachment to an endoscopic cannula 101 (e.g., a cannula of a hysteroscope) that is used to view a body cavity (e.g., a uterine cavity) of a patient. The operative cannula 100 is a disposable device that is configured to be attached to (e.g., clipped onto) the endoscopic cannula 101 and can be slide between a proximal portion 103 of the endoscopic cannula 101 (refer to FIG. 1) and a distal portion 105 of the endoscopic cannula 101 (refer to FIG. 2). The operative cannula 100 is configured to allow passage of a variety of surgical instruments (e.g., surgical forceps, biopsy punches, surgical scissors, polyp snares, biopsy forceps, grasping forceps, bipolar electrodes, and cytology brushes) along the endoscopic cannula 101 and into the body cavity for performing an intervention within the body cavity. Example interventions that can be performed using the operative cannula 100 include device retrievals, operative procedures (e.g., surgical procedures), and other procedures.

Figure 3:
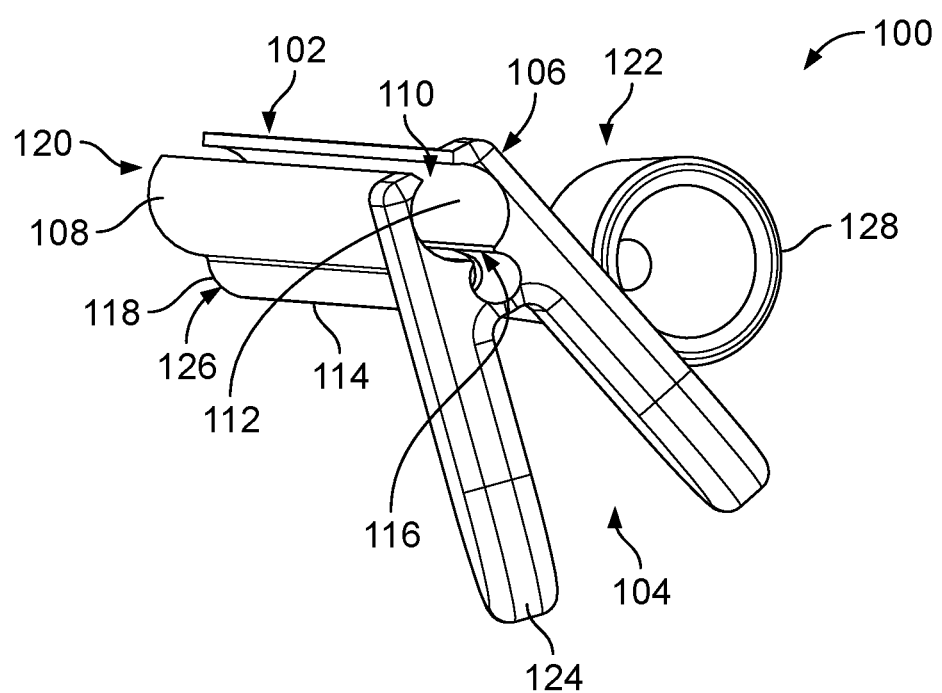
FIG. 3 is a perspective view of the operative cannula of FIG. 1 in a nominal state.
Figure 4:
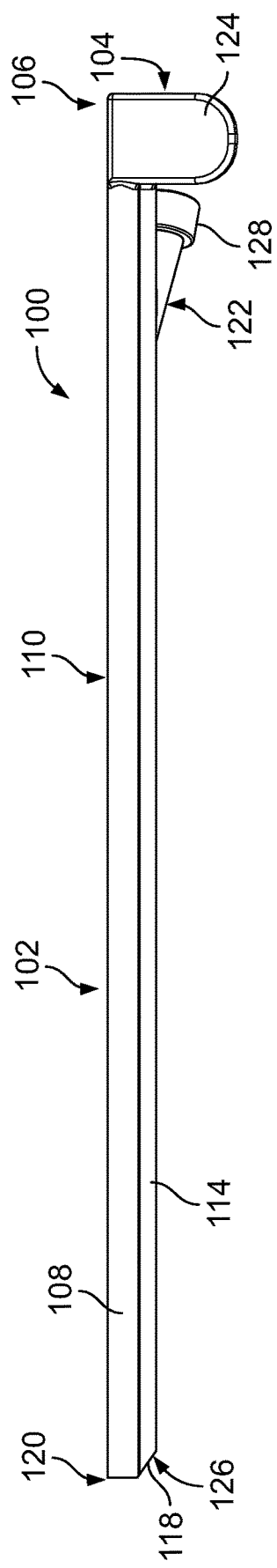
FIG. 4 is a side view of the operative cannula of FIG. 1 in a nominal state.

Referring to FIGS. 3 and 4, the operative cannula 100 includes an elongate shaft 102, a handle portion 104 (e.g., a gripping member) extending from a proximal end 106 of the elongate shaft 102, and an entry port 122 extending from the elongate shaft 102 near the proximal end 106. The elongate shaft 102 includes wall portions 108 that together form a generally cylindrical tubular structure. The wall portions 108 define an exterior opening 110 of the elongate shaft 102 that leads to an interior pocket 112 sized to receive the endoscopic cannula 101. The exterior opening 110 is an elongate opening that extends along the length of the elongate cannula 102. In a nominal state of the operative cannula 100, a width of the exterior opening 110 of the elongate shaft 102 is less than a diameter of the endoscopic cannula 101. The wall portions 108 also define an interior opening 116 that is positioned opposite the exterior opening 110. The interior opening 116 is an elongate opening that extends along the length of the elongate cannula 102.

A structure of the elongate shaft 102 (e.g., including the exterior opening 110), together with a material choice of the operative cannula 100, provides the elongate shaft 102 with a flexibility that allows the wall portions 108 to spread apart (e.g., to be forced or pulled apart) to allow passage of the endoscopic cannula 101 through the exterior opening 110 and into the interior pocket 112 of the elongate shaft 102. Therefore, the operative cannula 100 can be attached to (e.g., clipped onto) the endoscopic cannula 101 by aligning the endoscopic cannula 101 parallel to the elongate shaft 102 and pressing the endoscopic cannula 101 against the exterior opening 110 of the elongate shaft 102 until the endoscopic cannula 101 forces the wall portions 108 apart and snaps into the interior pocket 112 of the elongate shaft 102. In this manner, the operative cannula 100 can be easily clipped onto the endoscopic cannula 101. The elongate shaft 102 is short enough in length to allow the operative cannula 100 to be clipped onto the proximal portion 103 of the endoscopic cannula 101 without having to remove (e.g., withdraw) the endoscopic cannula 101 from the patient. In some examples, the operative cannula 100 may be attached to the endoscopic cannula 101 by sliding the distal portion 105 of the endoscopic cannula 101 into the interior pocket 112 of the elongate shaft 102 from the proximal end 106 of the elongate shaft 102.

Due to the flexibility of the elongate shaft 102 and to a softness of the elongate shaft 102, the elongate shaft 102 is able to elastically (e.g., reversibly) deform (e.g., bend) to follow a nominal shape (e.g., a nominal curvature) of the endoscopic cannula 101 as the operative cannula 100 is slid along the endoscopic cannula 101. For example, as the operative cannula 100 is slid distally from the proximal portion 103 of the endoscopic cannula 101, the elongate shaft 102 can deform to follow a curve 107 (e.g., that has a radius of about 25°) in the endoscopic cannula 101. As the operative cannula 100 is slid proximally from the distal portion 105 of the endoscopic cannula 101, the elongate shaft 102 can regain its nominal, straight shape. Accordingly, the operative cannula 100 can advantageously be used with endoscopic cannulas having a variety of curvature profiles. Still referring to FIGS. 3 and 4, the elongate shaft 102 further includes a working channel 114 located along the interior opening 116 of elongate shaft 102. The working channel 114 has a generally circular cross-sectional shape and extends from the proximal end 106 of the elongate shaft 102 to a beveled edge 118 (e.g., an angled edge) aligned along one side with a distal end 120 of the elongate shaft 102. The working channel 114 is sized to allow passage of surgical instruments (e.g., surgical forceps, biopsy punches, surgical scissors, polyp snares, biopsy forceps, grasping forceps, bipolar electrodes, and cytology brushes) for carrying out an intervention (e.g., operation or another procedure) within the body cavity of the patient. The beveled edge 118 forms a tapered tip that can ease insertion of the distal end 120 of the elongate shaft 102 of the operative cannula 100 into the cervix. The beveled edge 118 forms a distal opening 126 that has an elliptical shape, which provides the distal opening 126 with an area that is larger than the circular cross-sectional area of the working channel 114. The larger area of the distal opening 126 facilitates exit of a distal end of the surgical instrument from the operative cannula 100 as the surgical instrument is slid distally within the working channel 114. The larger area of the distal opening 126 also facilitates withdrawal of the distal end of the surgical instrument through the distal opening 126.

Surgical instruments used with the operative cannula 100 are flexible enough to deform according to the shape of the working channel 114 as the surgical instruments are slid within the working channel 114 (e.g., as guided by the shape of the endoscopic cannula 101). The entry port 122 extends from a side of the working channel 114 and provides an entry point for introducing the surgical instrument into the working channel 114. The entry port 122 includes an exterior rim 128 and has a generally conical shape that guides the surgical instrument into the working channel 114 as the surgical instrument is inserted into the working channel 114. In some examples, the exterior rim 128 of the entry port 122 may serve as a back-stop that locates an external orifice of the cervix if the exterior rim 122 abuts the cervix as the elongate shaft 102 is inserted into the cervix. In some examples, the interior opening 116 of the elongate shaft 102 can provide an alternative entryway for introducing the surgical instrument into the working channel 114 (e.g., by first introducing the surgical instrument into the interior pocket 112 via the exterior opening 110). In some examples, a proximal opening 130 of the working channel 114 provides an entry point for introducing the surgical instrument into the working channel 114.

The handle portion 104 includes two tabs 124 that together form a clip attached to the elongate shaft 102. The tabs 124 are sized to be grasped by a user (e.g., a clinician) of the operative cannula 100 to slide the operative cannula 100 proximally and distally along the endoscopic cannula 101. The tabs 124 can be urged (e.g., squeezed or pinched) together to pull the wall portions 108 apart to widen the opening 110 of the elongate shaft 102 to facilitate entry of the endoscopic cannula 101 into the interior pocket 112 of the operative cannula or to facilitate exit of endoscopic cannula 101 from the interior pocket 112 of the operative cannula 100. For example, the user can urge the tabs 124 together to widen the operative cannula 100 near the proximal end 106 of the elongate shaft 102 and then place the widened, proximal portion of the operative cannula 100 around the endoscopic cannula 101. From an urged position, the tabs 124 can be released to allow the wall portions 108 to approach each other around the endoscopic cannula 101 to facilitate attachment of the operative cannula 100 to the endoscopic cannula 101. With the proximal portion of the operative cannula 100 attached to the endoscopic cannula 101, the user can use his or her fingers to guide a remaining portion of the operative cannula 100 onto the endoscopic cannula 101.

The elongate shaft 102 (e.g., including the wall portions 108 and the working channel 114) of the operative cannula 100 typically has a length of about 101.6 mm to about 304.8 mm (e.g., about 177.8 mm). The cylindrical tube provided by the wall portions 108 typically has a nominal internal diameter (e.g., defining a diameter of the interior pocket 112) of about 2.0 mm to about 30.0 mm (e.g., about 3.6 mm) and a wall thickness of about 0.13 mm to about 2.00 mm (e.g., about 0.36 mm) such that the interior pocket 112 can surround the endoscopic cannula 101. The exterior opening 110 of the elongate shaft 102 typically has a nominal width of about 0.13 mm to about 15.0 mm (e.g., about 1.30 mm). The working channel 114 typically has an internal diameter of about 0.50 mm to about 20.00 mm (e.g., about 1.85 mm) and a wall thickness of about 0.13 mm to about 2.00 mm (e.g., about 0.36 mm). The beveled edge 118 of the working channel 114 is typically oriented at an angle of about 5° to about 80° (e.g., about 35°) from a central axis of the elongate shaft 102.

The tabs 124 typically have a width of about 6.4 mm to about 25.4 mm (e.g., about 11.4 mm), a thickness of about 1.0 mm to about 13.0 mm (e.g., about 2.5 mm), and a length (measured from the exterior opening 110 to ends of the tabs 124) of about 6.4 mm to about 38.1 mm (e.g., about 16.5 mm). The tabs 124 extend from the elongate shaft 102 at an angle of about 5° to about 90° (e.g., about 13°) with respect to the central axis of the elongate shaft 102. The entry port 122 extends from the side of the working channel 114 at an angle of about 0° to about 60° (e.g., about 21°) and has a maximum internal diameter of about 0.5 mm to about 20.0 mm (e.g., about 1.9 mm).

In some embodiments, the operative cannula 100 includes a locking feature (e.g., provided by one or more detents, recesses, or other physical stops) positioned near the distal end 120 of the elongate shaft 102 that can mate with a corresponding locking feature positioned along the distal portion 105 of the endoscopic cannula 101 to secure the operative cannula 100 in place along the distal portion 105 of the endoscopic cannula 101 (e.g., to prevent the operative cannula 100 from sliding distally off of the endoscopic cannula 101).

The operative cannula 100 may be manufactured via one or more techniques including injection molding, extrusion, casting, machining, stereolithography (SLA), and fused deposition molding (FDM). The operative cannula 100 is typically made of one or materials that are relatively soft and/or that have a relatively high elasticity, such as polypropylene, nylon, polytetrafluoroethylene (PTFE), silicone, latex rubber, acrylonitrile butadiene styrene (ABS), polycarbonate, polystyrene, and polyether block amide (PEBA). Such materials typically have a hardness in a range of about 0 Shore A to about 100 Shore A. The elongate shaft 102, the handle portion 104, and the entry port 122 may be made of the same one or more materials or made of different, respective materials.

Figure 5:
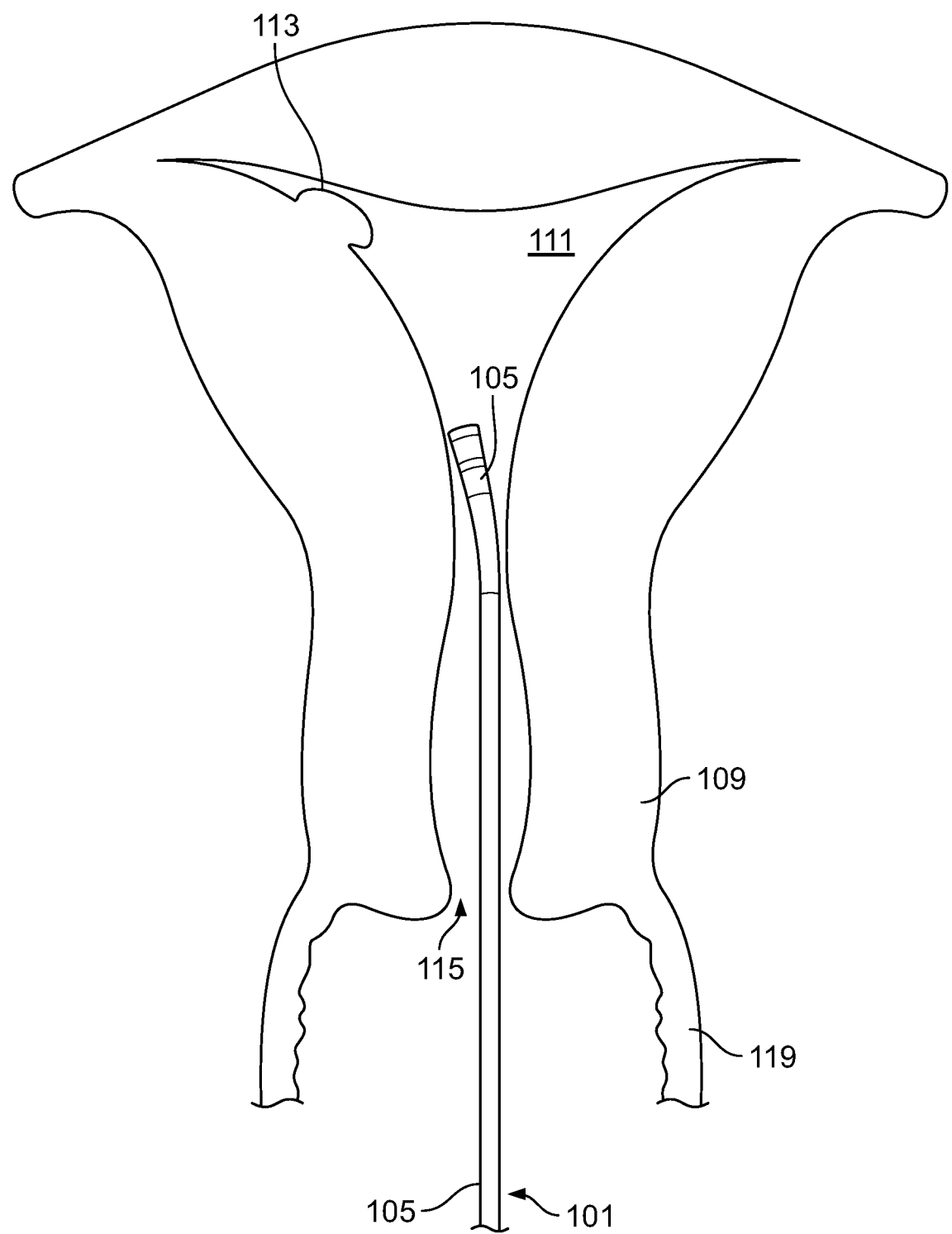
FIGS. 5-10 illustrate a method of using the operative cannula of FIG. 1 during an endoscopic procedure.

FIGS. 5-10 illustrate a method of using the operative cannula 100 during an endoscopic procedure (e.g. a hysteroscopic procedure). Referring to FIG. 5, a clinician uses a handset (not shown) attached to the endoscopic cannula 101 to insert the endoscopic cannula 101 into a cervix 109 of a patient. The clinician advances the endoscopic cannula 101 distally until the distal portion 105 of the endoscopic cannula 101 is positioned at a desired location and at a desired orientation within a uterine cavity 111 of the patient. In some cases (as in the example of FIGS. 5-10), the clinician views an abnormality 113, such as an endometrial lesion, a uterine fibroid (e.g., a myoma), a uterine polyp, a cancerous tumor, an adhesion, a hyperplastic growth (or, in some cases, another anatomical feature of interest, such as a healthy-appearing tissue disposed near a region of interest) within the uterine cavity 111 via a video stream or via one or more images captured by the endoscopic cannula 101 and displayed on a monitor of the handset. Upon viewing the abnormality 113, the clinician may decide to perform an operation (e.g., a biopsy procedure, a polypectomy, an excision, or a cautery) within the uterine cavity 111 to further examine or to treat the abnormality 113.

Figure 6:
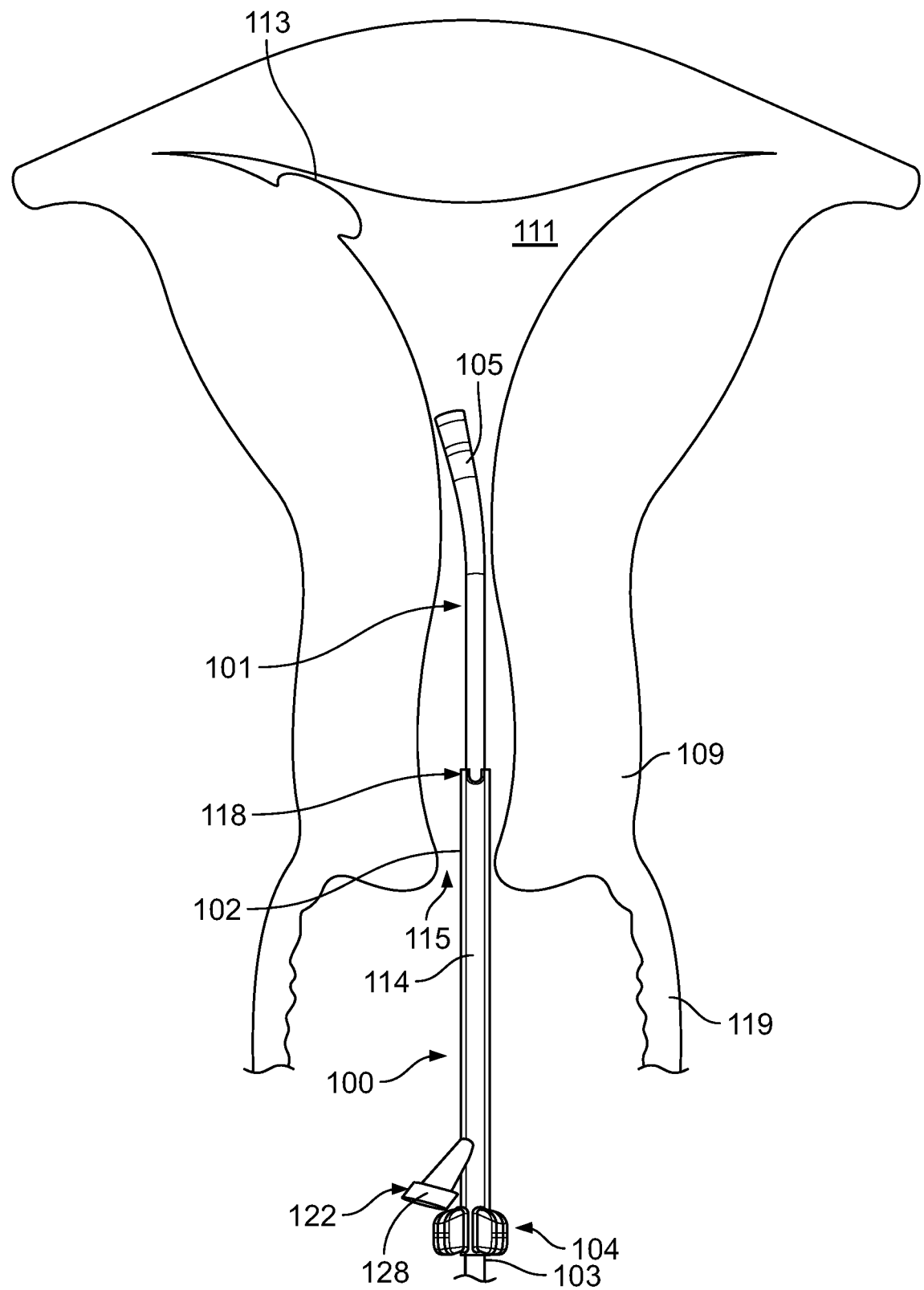

Referring to FIG. 6, the clinician attaches (e.g., clips) the operative cannula 100 to the proximal portion 103 of the endoscopic cannula 101 that is disposed within the vaginal canal 119 or disposed external to the patient.

Figure 7:
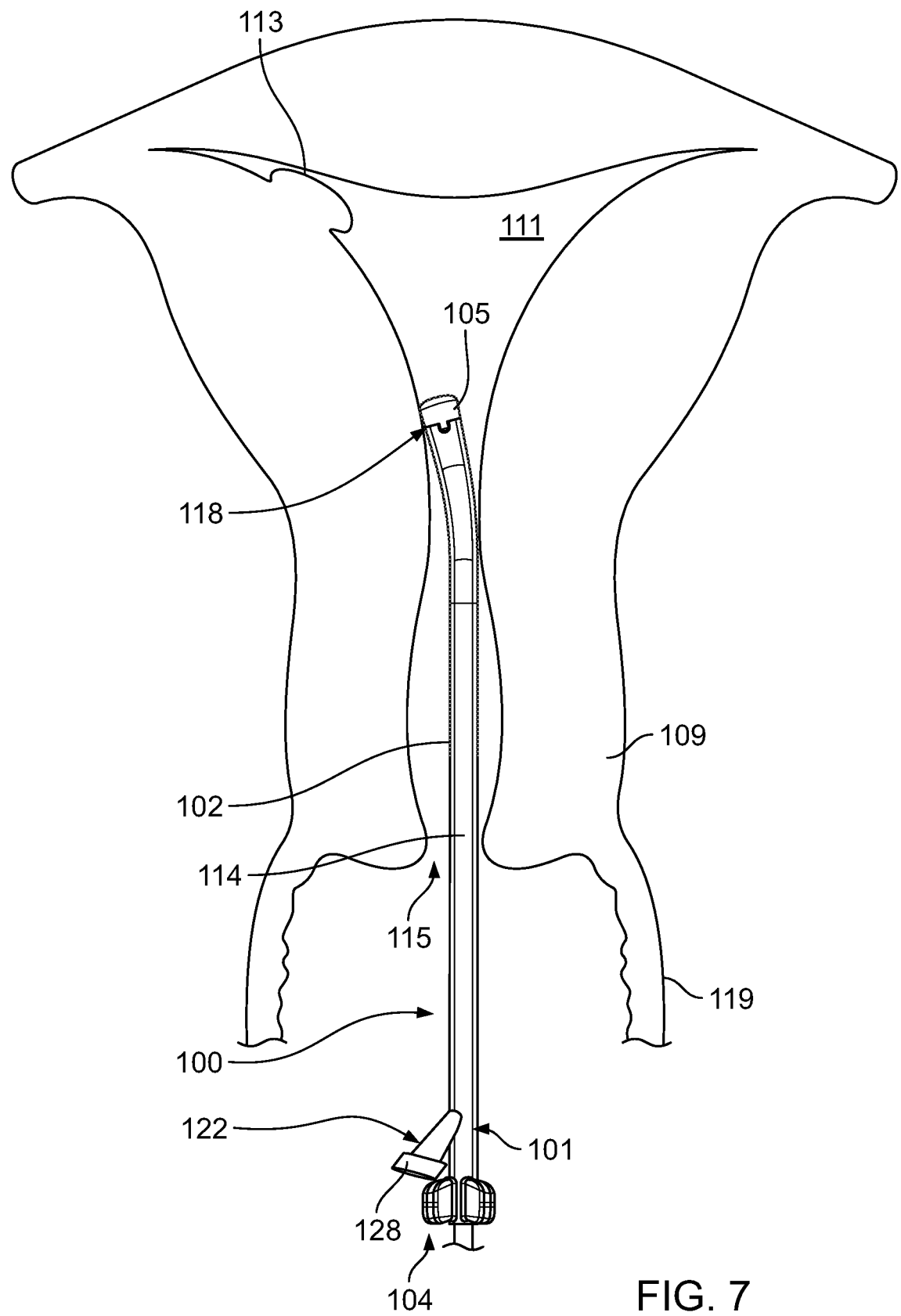

Referring to FIG. 7, the clinician then grasps the handset attached to the endoscopic cannula 101 with one hand to hold the endoscopic cannula 101 in place within the uterine cavity 111, while sliding the handle portion 104 of the operative cannula 100 distally along the endoscopic cannula 101 until the operative cannula 100 passes through the cervix 109 and into the uterine cavity 111. In some examples, the operative cannula 100 can be slid distally along the endoscopic cannula 101 until a locking feature positioned near the distal end 120 of the elongate shaft 102 mates with a corresponding locking feature positioned along the distal portion 105 of the endoscopic cannula 101. In some examples, the operative cannula 100 can be slid distally along the endoscopic cannula 101 until the proximal end 106 of the elongate shaft 102 of the operative cannula 100 is aligned with a desired depth marking of a scale that may be marked along the endoscopic cannula 101. Such a scale along the endoscopic cannula 101 can indicate a depth to which the operative cannula 100 is inserted into an opening 115 of cervix 109.

Figure 8:
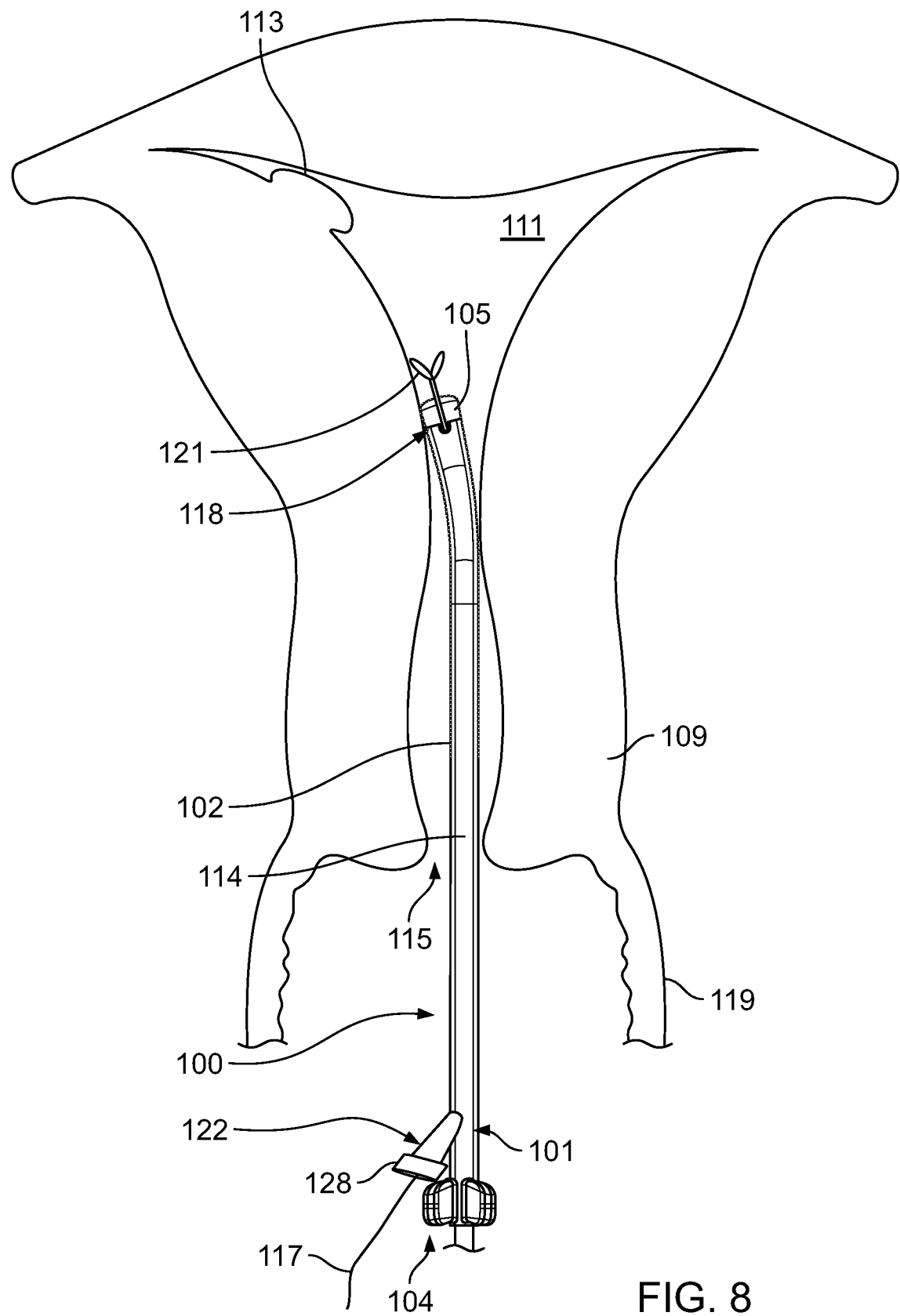

Referring to FIG. 8, the clinician then inserts a surgical instrument 117 into the entry port 122 and slides the surgical instrument 117 distally within the working channel 114 until the surgical instrument 117 exits the beveled edge 118 of the working channel 114 and is delivered into the uterine cavity 111. In the example of FIG. 8, the surgical instrument 117 has a distal end 121 that can be collapsed for insertion into the working channel 114 and that can expand upon exiting the working channel 114. Once in the uterine cavity 111, the clinician manipulates the surgical instrument 117 to perform the operation.

Figure 9:
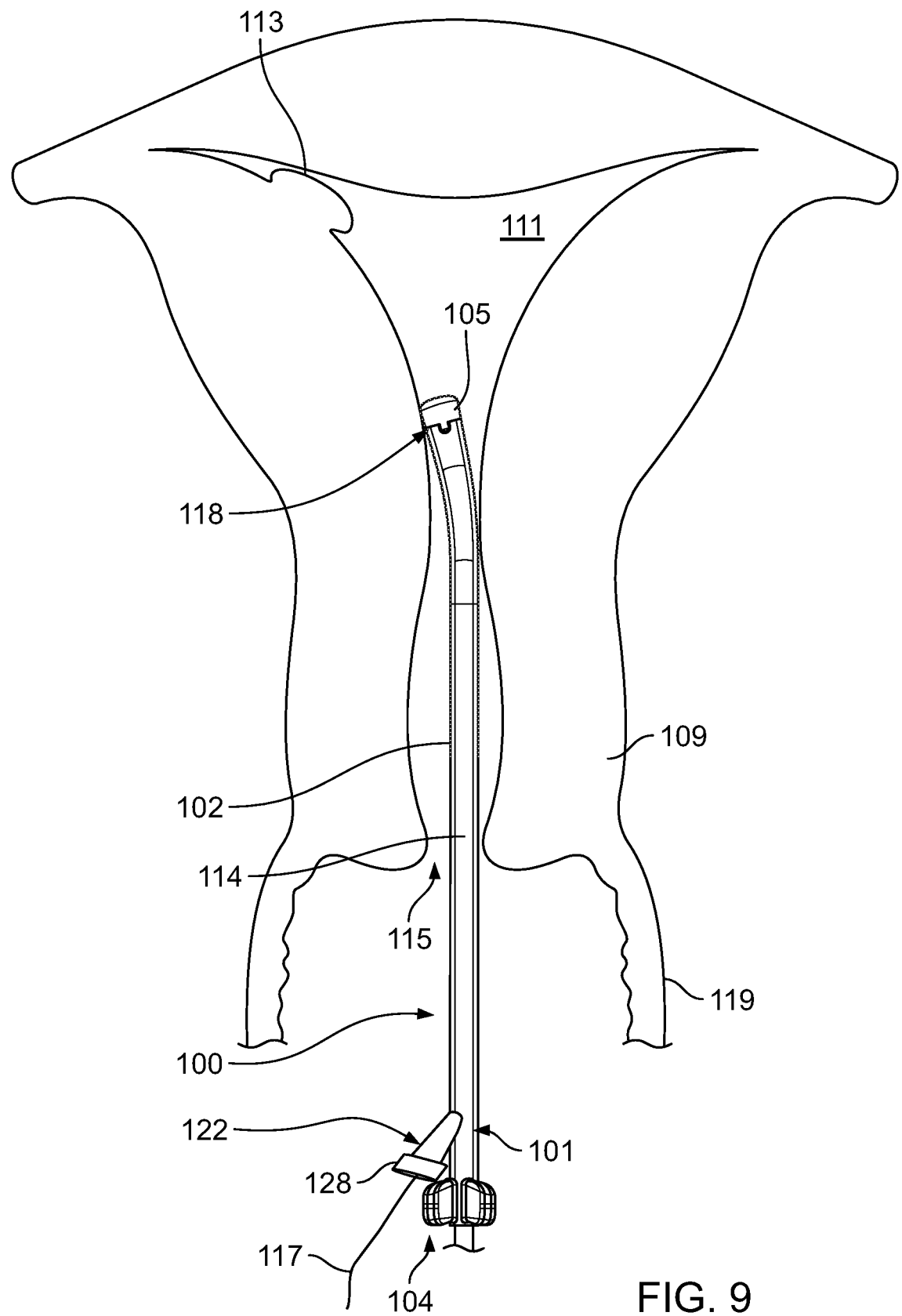

Referring to FIG. 9, the clinician withdraws the surgical instrument 117 from the working channel 114 through the entry port 122 upon completion of the operation. In some instances, depending upon the operation performed (e.g., a biopsy procedure), a uterine tissue sample may be carried by the surgical instrument 117 as the surgical instrument 117 is withdrawn through the working channel 114.

Figure 10:
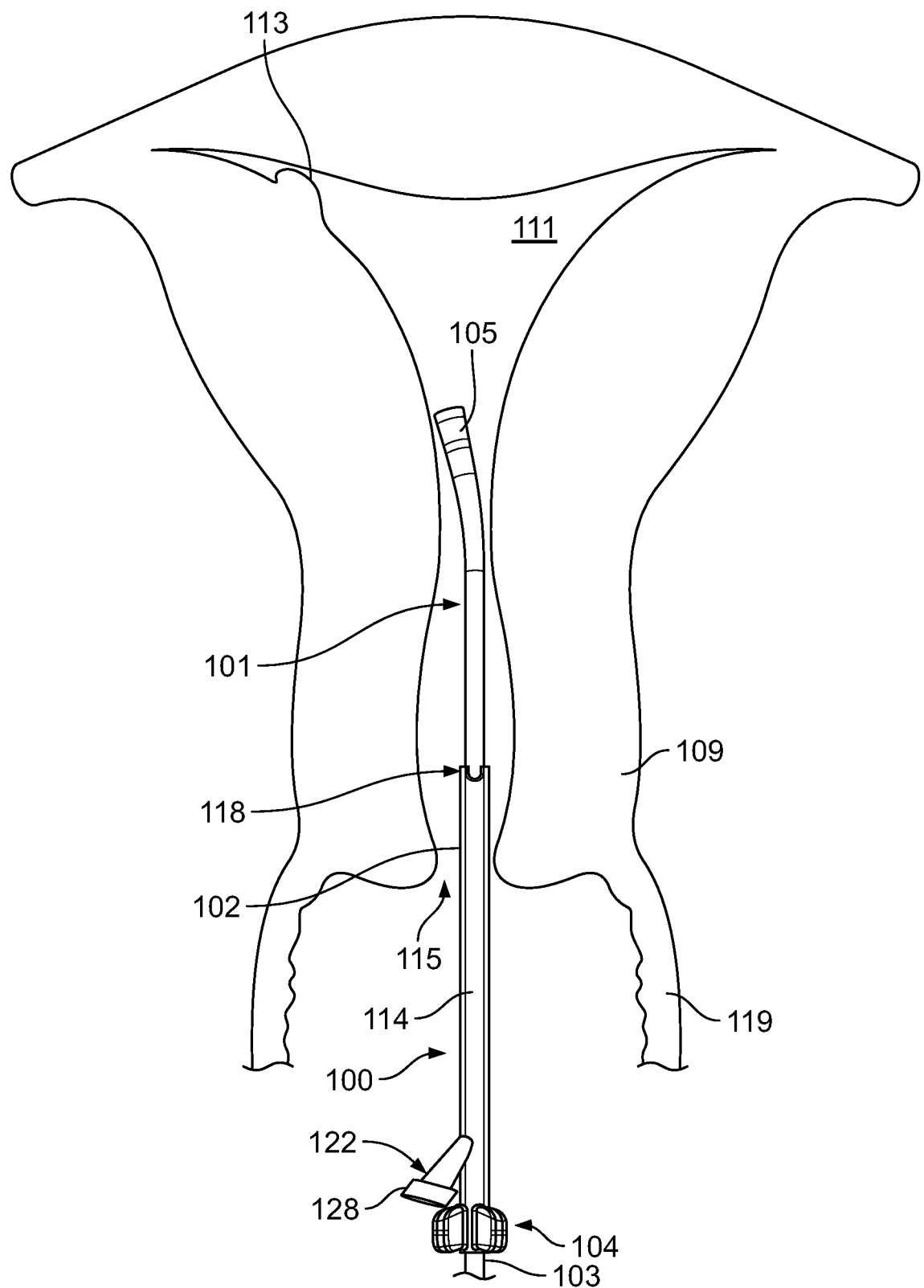

Referring to FIG. 10, the clinician may then grasp the handset attached to the endoscopic cannula 101 with one hand to hold the endoscopic cannula 101 in place within the uterine cavity 111, while pulling the handle portion 104 of the operative cannula 100 proximally with the other hand until the operative cannula 100 is positioned along the proximal portion 103 of the endoscopic cannula 101. The clinician then removes (e.g., pulls) the operative cannula 100 from the endoscopic cannula 101 so that the endoscopic cannula 101 can be used to make additional observations of the uterine cavity 111. Following the operation, the operative cannula 100 can be disposed of according to standard protocols.

In some instances, upon performing the operation and withdrawing the surgical instrument 117 from the working channel 114 through the entry port 122, the clinician withdraws the operative cannula 100 and the endoscopic cannula 101 from the cervix 109 while the operative cannula 100 is still attached to the endoscopic cannula 101. In other instances, upon performing the operation, the clinician withdraws the operative cannula 100, the endoscopic cannula 101, and the surgical instrument 117 from the cervix 109 while the operative cannula 100 is still attached to the endoscopic cannula 101 and while the surgical instrument 117 is still disposed within the working channel 114. For example, in some cases (e.g., with respect to a biopsy procedure), a tissue sample may be larger than the internal diameter of the working channel 114, such that the distal end 121 of the surgical instrument 117, carrying the tissue sample, is not withdrawn distally through the working channel 114 prior to removing the operative cannula 101 and the endoscopic cannula 101.

In some cases, the clinician may view a foreign body or a misplaced device (e.g., a migrated intrauterine device (IUD)) within the uterine cavity 111 via the video stream or via the one or more images displayed on the monitor of the handset. In such cases, the operative cannula 100 may be used in a procedure for removing the foreign body or for retrieving the misplaced device (e.g., for passing an instrument within the working channel 114 that can be used to remove the foreign body or to retrieve the device) from the uterine cavity 111.

The operative cannula 100 provides a low-cost alternative to an endoscopic cannula with an integrated working channel, which can be relatively costly to manufacture. The operative cannula 100 also provides a low-cost operative capability to an endoscopic cannula that does not have any operative features or operative capabilities. Given that the operative cannula 100 is packaged as a sterile, single-use device, the operative cannula 100 can also provide a safe (e.g., uncontaminated) alternative to an endoscopic cannula with an integrated working channel, which may be susceptible to contamination if not properly sterilized between procedures. Furthermore, the disposable nature of the operative cannula 100 can enable procedures that would otherwise be performed in a hospital to be performed in a physician's office or in a clinic, which may not have decontamination capabilities that are typically available in a hospital. Accordingly, using the operative cannula 100 can conserve time and treatment compounds (e.g., anesthesia) and can prevent logistical inconveniences to the patient that may otherwise be associated with a procedure that would be performed in a hospital. The operative cannula 100 can be packaged individually, and both the operative cannula 100 and the packaging will remain sterile for a shelf-life of the operative cannula 100.

Figure 11:
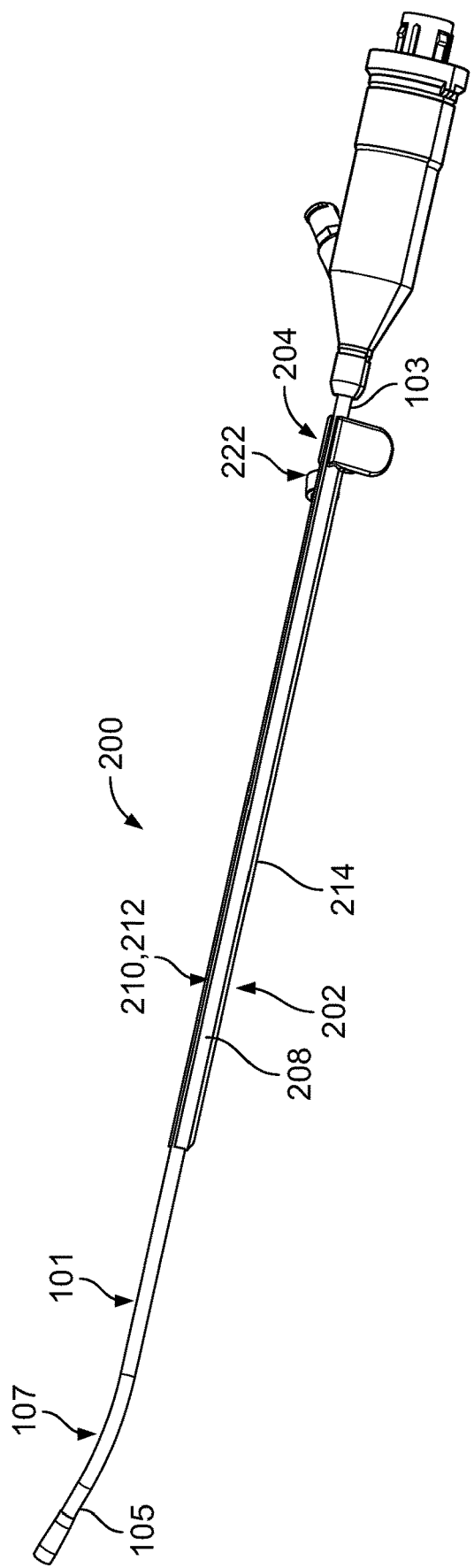
FIG. 11 is a perspective view of an operative cannula that includes rigid, separated shaft walls and that is positioned along the proximal portion of the endoscopic cannula of FIG. 1.
Figure 12:
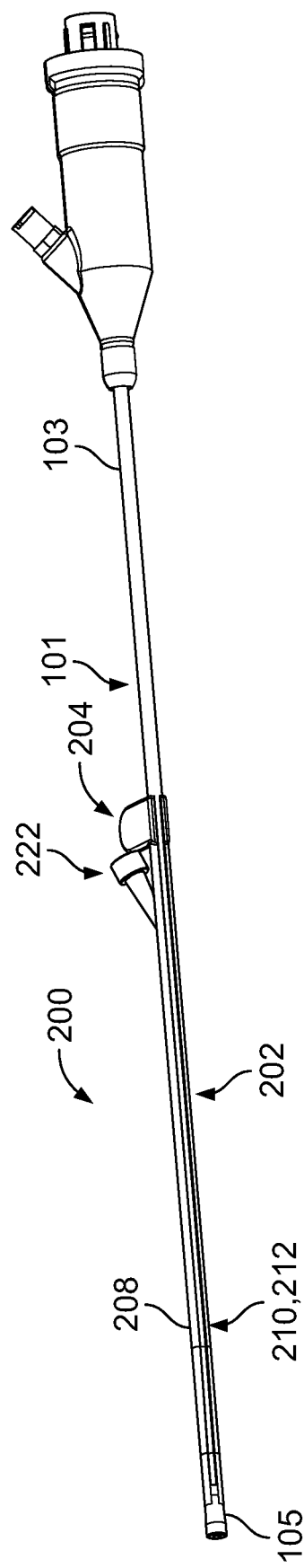
FIG. 12 is a perspective view of the operative cannula of FIG. 11 positioned along the distal portion of the endoscopic cannula of FIG. 1.

While certain embodiments have been described above, other embodiments are possible. For example, while the operative cannula 100 has been described as being made of one or materials that are relatively soft and/or that have a relatively high elasticity, other embodiments of an operative cannula may be made of one or materials that are relatively hard and/or that have a relatively low elasticity. FIGS. 11 and 12 illustrate an operative cannula 200 that is substantially similar in structure to the operative cannula 100 in the nominal state, except that the operative cannula 200 is made of a material formulation that is different from the material formulation of the operative cannula 100. Accordingly, the operative cannula 200 is a disposable device that is configured to be attached to (e.g., clipped onto) the endoscopic cannula 101 and can be slide between the proximal portion 103 of the endoscopic cannula 101 (refer to FIG. 11) and the distal portion 105 of the endoscopic cannula 101 (refer to FIG. 12). The operative cannula 200 is designed to allow passage of a surgical instrument along the endoscopic cannula 101 and into a body cavity (e.g., a uterine cavity) for performing an intervention within the body cavity.

The operative cannula 200 includes an elongate shaft 202 that is substantially similar in structure and similar in function to the elongate shaft 202 of the operative cannula 100. The operative cannula 200 further includes a handle portion 204 and an entry port 222 that are substantially similar in structure and function to the handle portion 104 and the entry port 122, respectively, of the operative cannula 100. Accordingly, the elongate shaft 202 has a flexibility that allows wall portions 208 of the elongate shaft 202 to spread apart (e.g., to be forced or pulled apart) to allow passage of the endoscopic cannula 101 through an exterior opening 210 and into an interior pocket 212 of the elongate shaft 202. Therefore, the operative cannula 200 can be attached to (e.g., clipped onto) the endoscopic cannula 101 by aligning the endoscopic cannula 101 parallel to the elongate shaft 202 and pressing the endoscopic cannula 101 against the exterior opening 210 of the elongate shaft 202 until the endoscopic cannula 101 forces the wall portions 208 apart and snaps into the interior pocket 212 of the elongate shaft 202. In this manner, the operative cannula 100 can be easily clipped onto the endoscopic cannula 101.

Although the elongate shaft 202 is flexible enough to be spread apart for clipping onto the endoscopic cannula 101, the elongate shaft 202 is rigid enough to maintain its shape and to deform (e.g., straighten) the shape of the endoscopic cannula 101 as the operative cannula 200 is slid along the endoscopic cannula 101. For example, the elongate shaft 202 remains substantially straight and substantially straightens the curve 107 in the endoscopic cannula 101 as the operative cannula 200 is slid towards the distal portion 105 of the endoscopic cannula 101. Accordingly, the operative cannula 200 may be used to perform an operation using a relatively rigid surgical instrument that cannot easily adapt to the nominal shape of the endoscopic cannula 101 as the surgical instrument is slid within a working channel 214 of the elongate shaft 202. Furthermore, the rigidity of the operative cannula 200 can also facilitate steering of the endoscopic cannula 101 within the uterine cavity.

In some embodiments, the operative cannula 200 includes a locking feature (e.g., provided by one or more detents, recesses, or other physical stops) positioned near a distal end 220 of the elongate shaft 202 that can mate with a corresponding locking feature positioned along the distal portion 105 of the endoscopic cannula 101 to secure the operative cannula 200 in place along the distal portion 105 of the endoscopic cannula 101 (e.g., to prevent the operative cannula 200 from sliding distally off of the endoscopic cannula 101).

The operative cannula 200 may be manufactured via the one or more techniques indicated above with respect to the operative cannula 100. The operative cannula 200 is typically made of one or materials that are relatively hard and/or that have a relatively low elasticity, such as polypropylene, nylon, PTFE, silicone, latex rubber, ABS, polycarbonate, polystyrene, PEBA, and metals (e.g., aluminum, spring steel, or various soft metals). Such materials typically have a hardness in a range of about 5 Shore D to about 95 Shore D.

A clinician can use the operative cannula 200 to perform an intervention within a uterine cavity of a patient to further examine, treat, remove, or manipulate an abnormality, an anatomical feature of interest, a healthy tissue, a foreign body, or a misplaced device according to the steps described above with respect to the operative cannula 100 and with respect to FIGS. 5-10. The operative cannula 200 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 200 can enable procedures that would otherwise be performed in a hospital to be performed in a physician's office or in a clinic, as discussed above with respect to the operative cannula 100.

Figure 13:
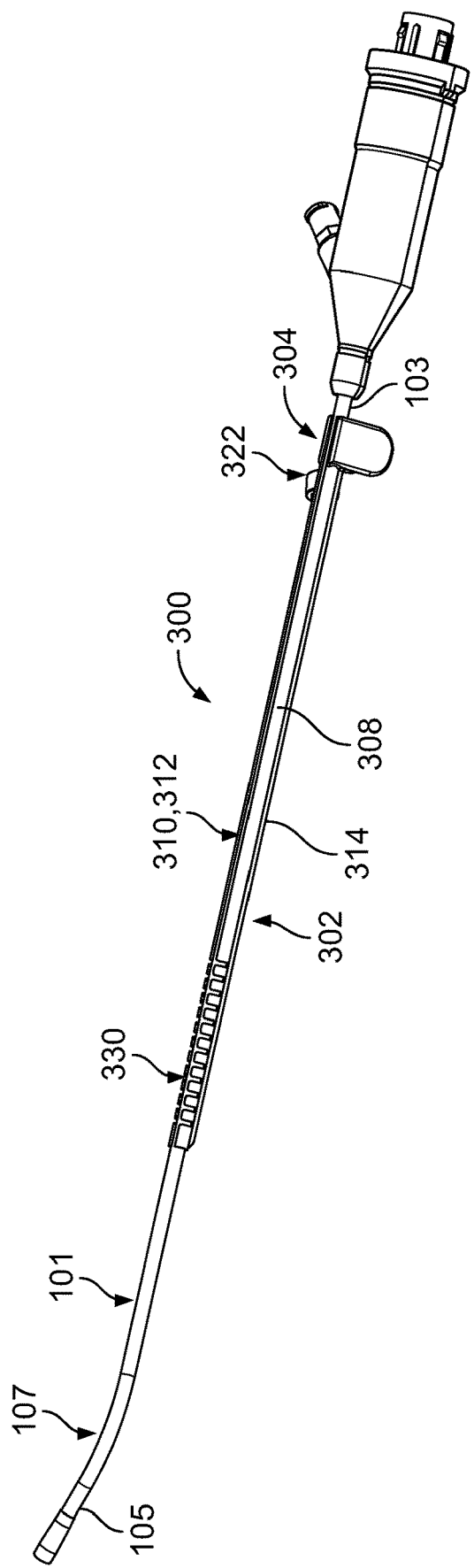
FIG. 13 is a perspective view of an operative cannula that includes bendable, slotted, separated shaft walls and that is positioned along the proximal portion of the endoscopic cannula of FIG. 1.
Figure 14:
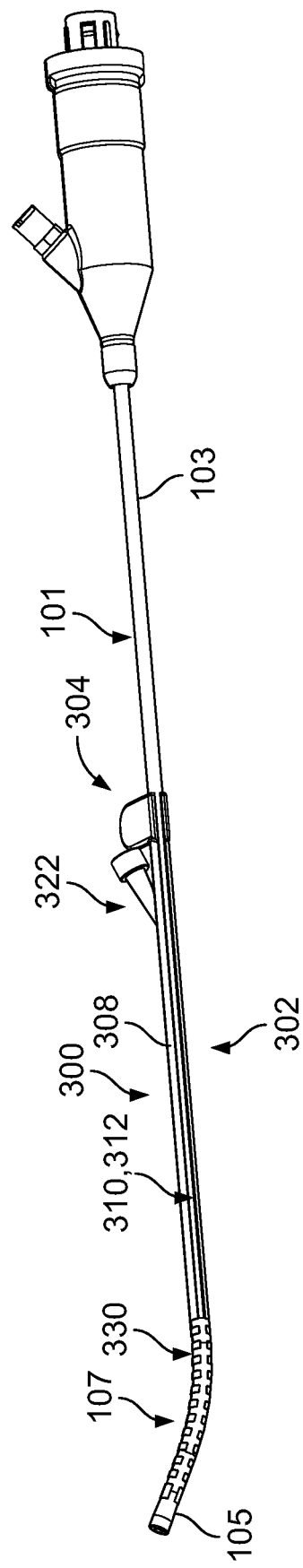
FIG. 14 is a perspective view of the operative cannula of FIG. 13 positioned along the distal portion of the endoscopic cannula of FIG. 1.

In some embodiments, an operative cannula may include an elongate shaft that has a slotted distal portion. For example, FIGS. 13 and 14 illustrate an operative cannula 300 that is substantially similar in structure and function to the operative cannula 100, except that the operative cannula 300 has a material formulation that is different from that of the operative cannula 100 and the operative cannula 300 includes an elongate shaft 302 that has a slotted distal portion. Accordingly, the operative cannula 300 is a disposable device that is configured to be attached to (e.g., clipped onto) the endoscopic cannula 101 and can be slide between the proximal portion 103 of the endoscopic cannula 101 (refer to FIG. 13) and the distal portion 105 of the endoscopic cannula 101 (refer to FIG. 14). The operative cannula 300 is designed to allow passage of a surgical instrument along the endoscopic cannula 101 and into a body cavity (e.g., a uterine cavity) for performing an intervention within the body cavity.

The operative cannula 300 includes a handle portion 304 and an entry port 322 that are substantially similar in structure and function to the handle portion 104 and the entry port 122, respectively, of the operative cannula 100. The elongate shaft 302 of the operative cannula 300 is substantially similar in structure to the elongate shaft 102 of the operative cannula 100, except that wall portions 308 of the elongate shaft 302 include multiple slots 330 (e.g., rectangular spaces) that extend from an exterior opening 310 of the elongate shaft 302 to a working channel 314 of the elongate shaft 302. A structure of the elongate shaft 302 (e.g., including the slots 330 and the exterior opening 310), together with a material choice of the operative cannula 300, provide the elongate shaft 302 with a flexibility that allows the wall portions 308 to spread apart (e.g., to be forced or pulled apart) to allow passage of the endoscopic cannula 101 through the exterior opening 310 and into the interior pocket 312 of the elongate shaft 302. Therefore, the operative cannula 300 can be attached to (e.g., clipped onto) the endoscopic cannula 101 by aligning the endoscopic cannula 101 parallel to the elongate shaft 302 and pressing the endoscopic cannula 101 against the exterior opening 310 of the elongate shaft 302 until the endoscopic cannula 101 forces the wall portions 308 apart and snaps into the interior pocket 312 of the elongate shaft 302. In this manner, the operative cannula 300 can be easily clipped onto the endoscopic cannula 101. The slots 330 typically have a width of about 0.5 mm to about 10.0 mm (e.g., about 2.0 mm).

Due to an increased flexibility imparted by the slots 330 (e.g., as compared to a flexibility of an operative cannula that is identical to the operative cannula 300 in material formulation and in structure, but that excludes the slots 330), the elongate shaft 302 is also able to elastically (e.g., reversibly) deform (e.g., bend) to follow the nominal shape of the endoscopic cannula 101 as the operative cannula 300 is slid along the endoscopic cannula 101. For example, as the operative cannula 300 is slid distally from the proximal portion 303 of the endoscopic cannula 101, the elongate shaft 302 can deform to follow the curve 107 in the endoscopic cannula 101. As the operative cannula 300 is slid proximally from the distal portion 105 of the endoscopic cannula 101, the elongate shaft 302 can regain its nominal, straight shape. Accordingly, the operative cannula 300 can advantageously be used with endoscopic cannulas having a variety of curvature profiles. Surgical instruments used with the operative cannula 300 are flexible enough to deform according to the shape of the working channel 314 of the elongate shaft 302 as the surgical instruments are slid within the working channel 314 (e.g., as guided by the shape of the endoscopic cannula 101).

In some embodiments, the operative cannula 300 includes a locking feature (e.g., provided by one or more detents, recesses, or other physical stops) positioned near a distal end 320 of the elongate shaft 302 that can mate with a corresponding locking feature positioned along the distal portion 105 of the endoscopic cannula 101 to secure the operative cannula 300 in place along the distal portion 105 of the endoscopic cannula 101 (e.g., to prevent the operative cannula 300 from sliding distally off of the endoscopic cannula 101).

The operative cannula 300 may be manufactured via the one or more techniques indicated above with respect to the operative cannula 100. The operative cannula 300 is typically made of one or materials that are relatively hard and/or that have a relatively low elasticity, such as polypropylene, nylon, PTFE, silicone, latex rubber, ABS, polycarbonate, polystyrene, and PEBA. Such materials typically have a hardness in a range of about 5 Shore D to about 95 Shore D. Owing to additional flexibility imparted by the slots 330, the operative cannula 300 is able to deform to follow the nominal shape of the endoscopic cannula 101 even though the operative cannula 300 has a relatively hard and/or a material formulation of relatively low elasticity.

A clinician can use the operative cannula 300 to perform an intervention within a uterine cavity of a patient to further examine, treat, remove, or manipulate an abnormality, an anatomical feature of interest, a healthy tissue, a foreign body, or a misplaced device according to the steps described above with respect to the operative cannula 100 and with respect to FIGS. 5-10. The operative cannula 300 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 300 can enable procedures that would otherwise be performed in a hospital to be performed in a physician's office or in a clinic, as discussed above with respect to the operative cannula 100.

Figure 15:
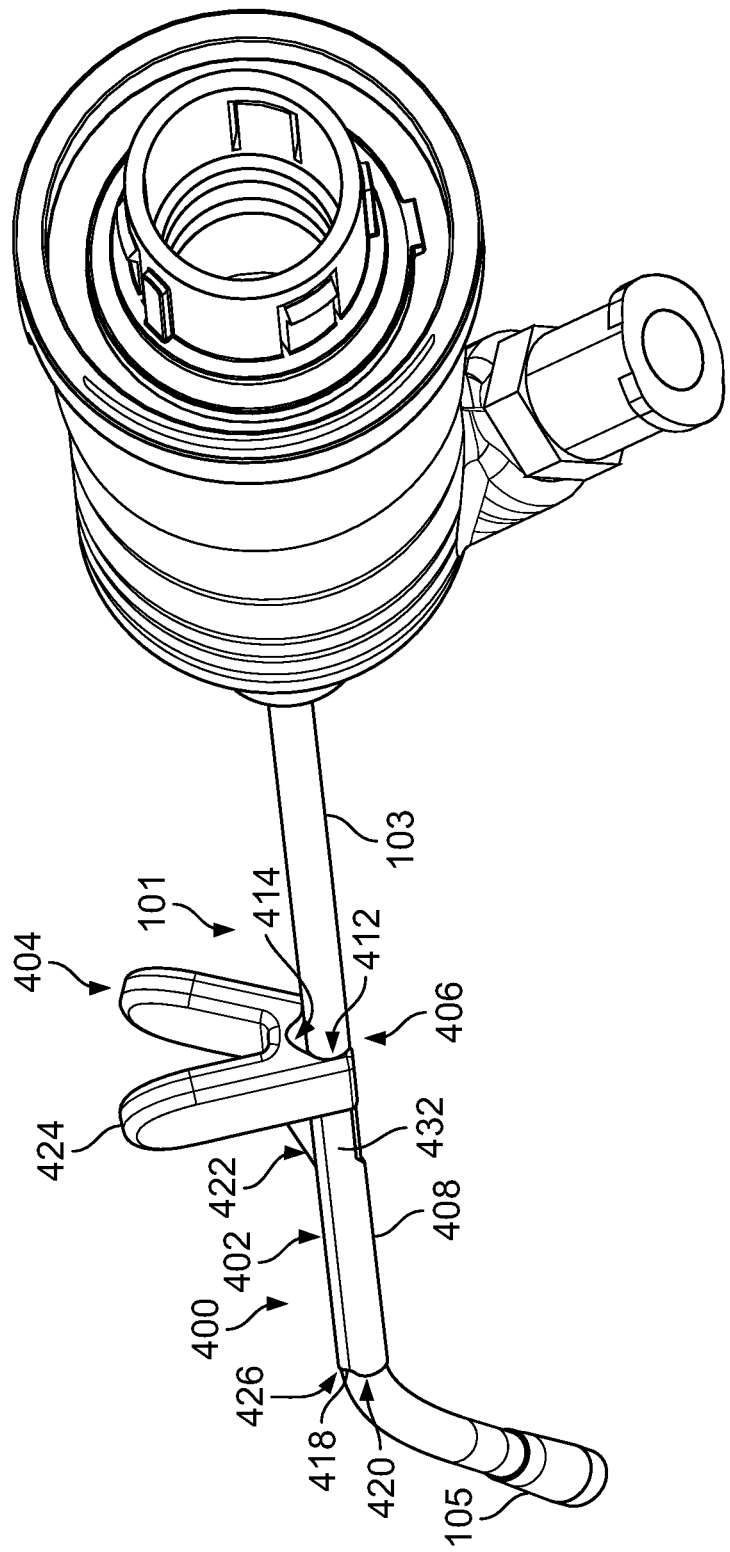
FIG. 15 is a perspective view of an operative cannula that includes a bendable, coiled shaft wall and that is positioned along the proximal portion of the endoscopic cannula of FIG. 1.
Figure 16:
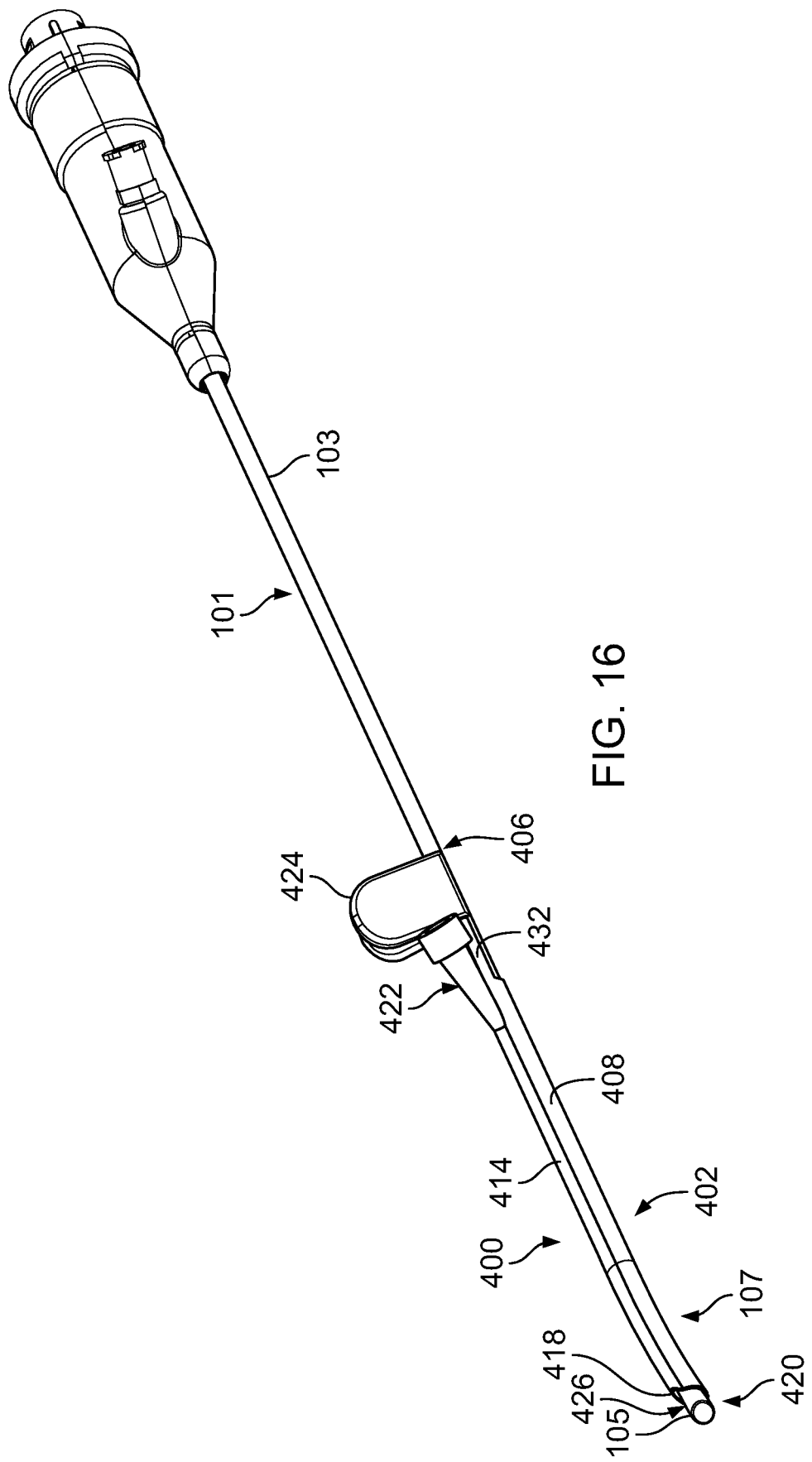
FIG. 16 is a perspective view of the operative cannula of FIG. 15 positioned along the distal portion of the endoscopic cannula of FIG. 1.

While the operative cannulas 100, 200, 300 have been described as including separated wall portions 108, 208, 308, in some embodiments, an operative cannula includes an elongate shaft formed of a single wall. For example, FIGS. 15 and 16 illustrate an operative cannula 400 that includes an elongate shaft 402 with a coiled wall 408. Accordingly, the operative cannula 400 is a disposable device that is configured to be attached to (e.g., clipped onto) the endoscopic cannula 101 and can be slide between the proximal portion 103 of the endoscopic cannula 101 (refer to FIG. 15) and the distal portion 105 of the endoscopic cannula 101 (refer to FIG. 16). The operative cannula 400 is designed to allow passage of a surgical instrument along the endoscopic cannula 101 and into the uterine cavity for performing an operation within the uterine cavity. The operative cannula 400 includes a handle portion 404 and an entry port 422 that are substantially similar in structure and function to the handle portion 104 and the entry port 122, respectively, of the operative cannula 100.

Figure 17:
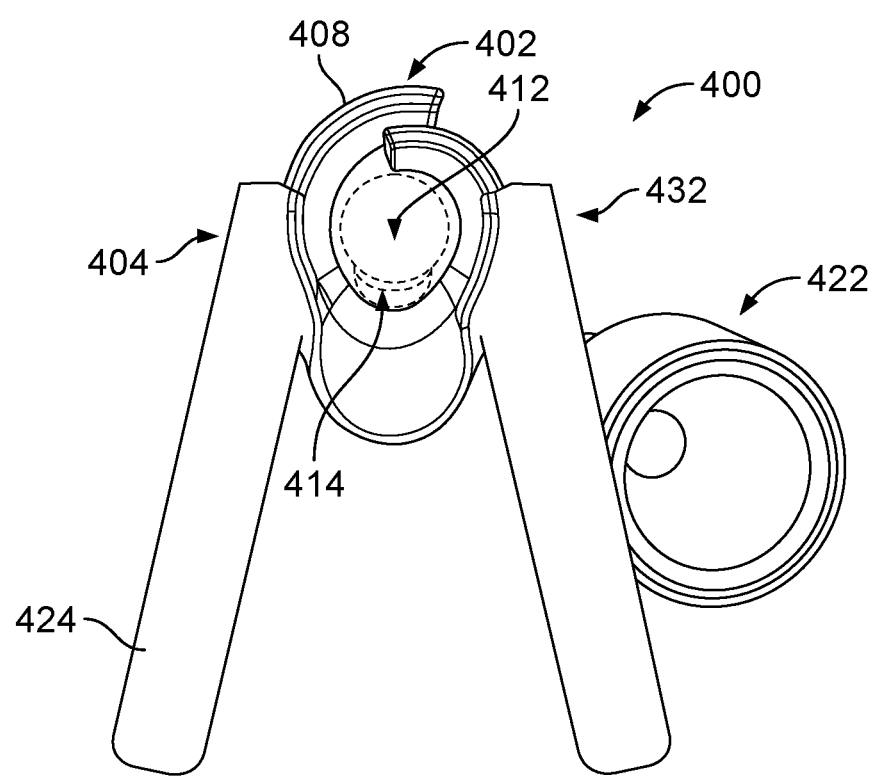
FIG. 17 is a perspective view of the operative cannula of FIG. 15 in a nominal state.
Figure 18:
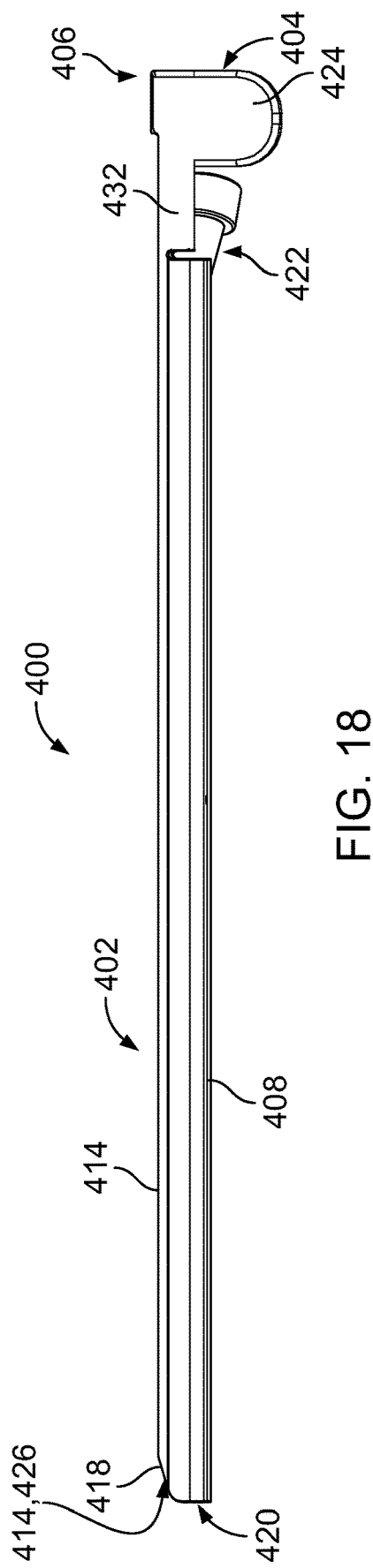
FIG. 18 is a side view of the operative cannula of FIG. 15 in a nominal state.

Referring to FIGS. 17 and 18, the elongate shaft 402 includes the coiled wall 408, which wraps around itself in a nominal state. The coiled wall 408 defines an interior pocket 412 that has a generally circular cross-sectional shape and that is sized to receive (e.g., surround) the endoscopic cannula 101. The elongate shaft 402 has a flexibility that allows the coiled wall 408 to be spread (e.g., pulled) apart to allow the endoscopic cannula 101 to be placed (e.g., snapped or clipped) into the interior pocket 412 of the elongate shaft 402 for attaching the operative cannula 400 to the endoscopic cannula 101. The coiled wall 408 also defines a portion of a working channel 414 that extends along the interior pocket 412. The elongate shaft 402 further includes an extension piece 432 that provides a remaining portion of the working channel 414 and from which the handle portion 404 extends. The elongate shaft 402 is short enough in length to allow the operative cannula 400 to be attached to the proximal portion 103 of the endoscopic cannula 101 without having to remove the endoscopic cannula 101 from of the cervix. In some examples, the operative cannula 400 may be attached to the endoscopic cannula 101 by sliding the distal portion 105 of the endoscopic cannula 101 into the interior pocket 412 of the elongate shaft 402 from the proximal end 406 of the elongate shaft 402.

Due to the flexibility of the elongate shaft 402 and due to a softness of the elongate shaft 402, the elongate shaft 402 is able to elastically (e.g., reversibly) deform (e.g., bend) to follow the nominal shape of the endoscopic cannula 101 as the operative cannula 400 is slid along the endoscopic cannula 101. For example, the elongate shaft 402 can deform to follow the curve 107 in the endoscopic cannula 101 as the operative cannula 400 is slid towards the distal portion 105 of the endoscopic cannula 101.

The working channel 414 has a generally semi-circular or crescent-shaped cross-sectional area and extends from a proximal end 406 of the elongate shaft 402 to a beveled edge 418 (e.g., an angled edge) aligned with a distal end 420 of the elongate shaft 402. The working channel 414 is sized to allow passage of surgical instruments (e.g., surgical forceps, biopsy punches, surgical scissors, polyp snares, biopsy forceps, grasping forceps, bipolar electrodes, and cytology brushes) for carrying out an intervention within the uterine cavity of the patient. The beveled edge 418 forms a tapered tip that can ease insertion of the distal end 420 of the elongate shaft 402 of the operative cannula 400 into the cervix. The beveled edge 418 forms a distal opening 426 that has an elliptical shape, which provides the distal opening 426 with an area that is larger than the circular cross-sectional area of the working channel 414. The larger area of the distal opening 426 facilitates exit of a distal end of the surgical instrument from the operative cannula 400 as the surgical instrument is slid distally within the working channel 414. The larger area of the distal opening 426 also facilitates withdrawal of the distal end of the surgical instrument through the distal opening 426.

Surgical instruments used with the operative cannula 400 are flexible enough to deform according to the shape of the working channel 414 as the surgical instruments are slid within the working channel 414 (e.g., as guided by the shape of the endoscopic cannula 101). As described above with respect to the entry port 122 of the operative cannula 100, the entry port 422 extends from a side of the working channel 414 and provides an entry point for introducing a surgical instrument into the working channel 414. In some examples, a proximal opening 430 of the working channel 414 provides an entry point for introducing the surgical instrument into the working channel 414. The handle portion 404 includes two tabs 424 that together form a clip attached to the extension piece 432 elongate shaft 402. The tabs 424 can be squeezed together to widen the extension piece 432 and thereby pull the coiled wall 408 apart to facilitate attachment of the operative cannula 400 to or removal of the operative cannula 400 from the endoscopic cannula 101.

The elongate shaft 402 (e.g., including the coiled wall 408 and the extension piece 432) of the operative cannula 400 has a length that is about equal to the length of the elongate shaft 102 of the operative cannula 100. The interior pocket 412 of the elongate shaft 402 typically has a nominal diameter that is about equal to the nominal diameter of the interior pocket 112 of the operative cannula 100 such that the interior pocket 412 can surround the endoscopic cannula 101. The working channel 414 typically has a diameter of about 0.5 mm to about 20.0 mm (e.g., about 2.5 mm). The entry port 422 extends from the side of the working channel 414 at an angle of about 5° to about 80° (e.g., about) 35°.

In some embodiments, the operative cannula 400 includes a locking feature (e.g., provided by one or more detents, recesses, or other physical stops) positioned near the distal end 420 of the elongate shaft 402 that can mate with a corresponding locking feature positioned along the distal portion 105 of the endoscopic cannula 101 to secure the operative cannula 400 in place along the distal portion 105 of the endoscopic cannula 101 (e.g., to prevent the operative cannula 400 from sliding distally off of the endoscopic cannula 101).

The operative cannula 400 may be manufactured via one or more techniques including injection molding, extrusion, casting, machining, SLA, and FDM. The operative cannula 400 is typically made of one or materials that are relatively soft and/or that have a relatively high elasticity, such as polypropylene, nylon, PTFE, silicone, latex rubber, ABS, polycarbonate, polystyrene, and PEBA. Such materials typically have a hardness in a range of about 0 Shore A to about 100 Shore A The elongate shaft 402, the handle portion 404, and the entry port 422 may be made of the same one or more materials or made of different, respective materials. In some examples, the coiled wall 408 of the operative cannula 400 makes the operative cannula 400 less likely to pop off of the endoscopic cannula 101 as compared to other operative cannulas that do not have coiled walls.

A clinician can use the operative cannula 400 to perform an intervention within a uterine cavity of a patient to further examine, treat, remove, or manipulate an abnormality, an anatomical feature of interest, a healthy tissue, a foreign body, or a misplaced device according to the steps described above with respect to the operative cannula 100 and with respect to FIGS. 5-10. The operative cannula 400 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 400 can enable procedures that would otherwise be performed in a hospital to be performed in a physician's office or in a clinic, as discussed above with respect to the operative cannula 100.

Figure 19:
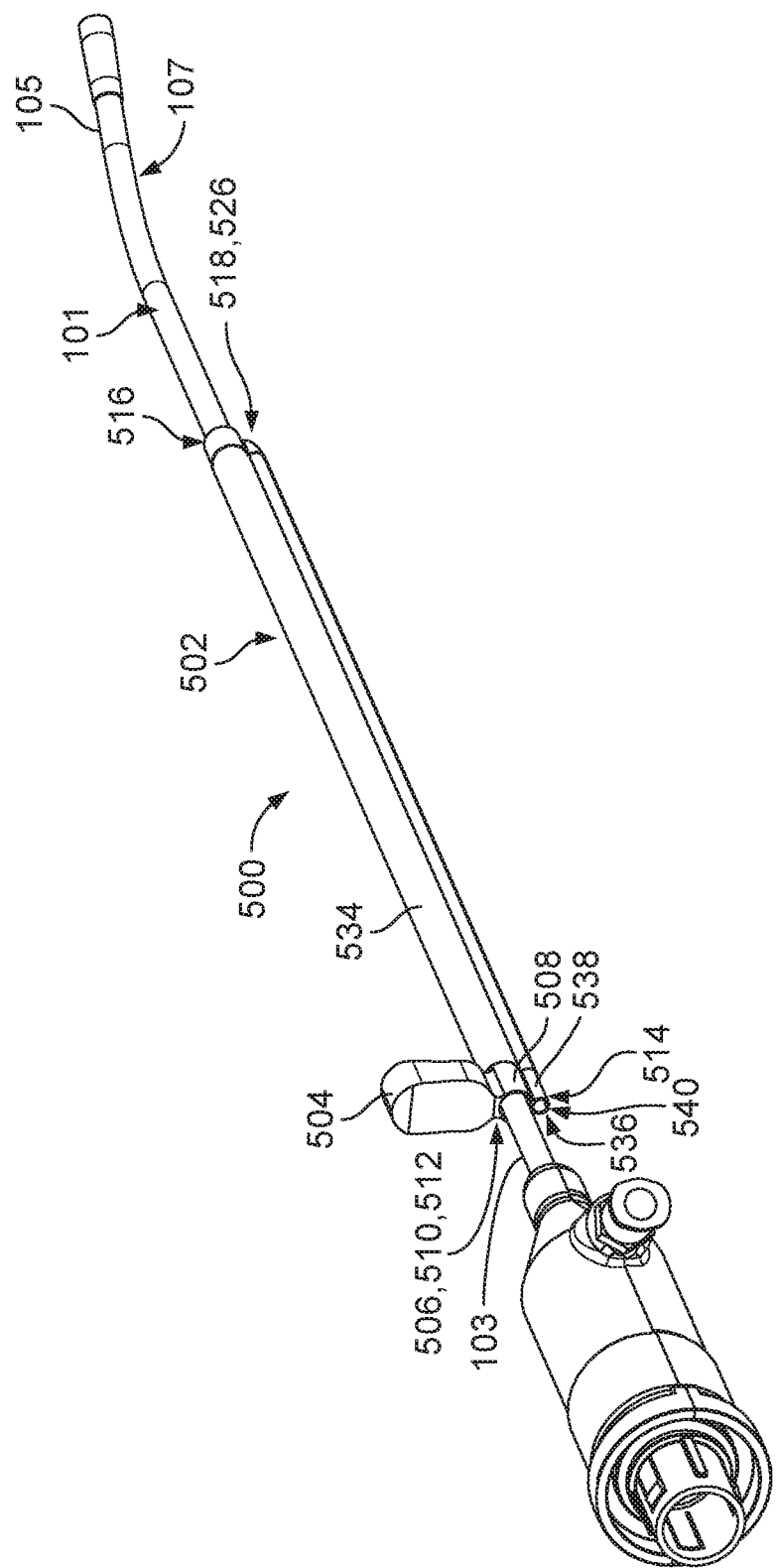
FIG. 19 is a perspective view of an operative cannula that includes a closed tubular wall and an expandable working channel, positioned along the proximal portion of the endoscopic cannula of FIG. 1.

While the operative cannulas 100, 200, 300, 400 have been described and illustrated as including the fixed-diameter working channels 114, 214, 314, 414 and the one or more wall portions 108, 208, 308, 408 that can be spread apart to clip the operative cannulas 100, 200, 300, 400 onto the endoscopic cannula 101, in some embodiments, an operative cannula includes an expandable working channel and a closed wall that can be slid onto the distal end 121 of the endoscopic cannula 101. For example, FIG. 19 illustrates an operative cannula 500 that includes such features. Like the operative cannulas 100, 200, 300, 400, the operative cannula 500 is a disposable device that is configured to allow passage of a surgical instrument along the endoscopic cannula 101 and into a uterine cavity for performing an intervention within the uterine cavity. The operative cannula 500 is configured to be slid onto the distal end 121 of the endoscopic cannula 101 and subsequently slid between the distal portion 105 of the endoscopic cannula 101 and the proximal portion 103 of the endoscopic cannula (as shown in FIG. 19). Example interventions that can be performed using the operative cannula 500 include device retrievals, operative procedures (e.g., surgical procedures), and other procedures.

Figure 20:
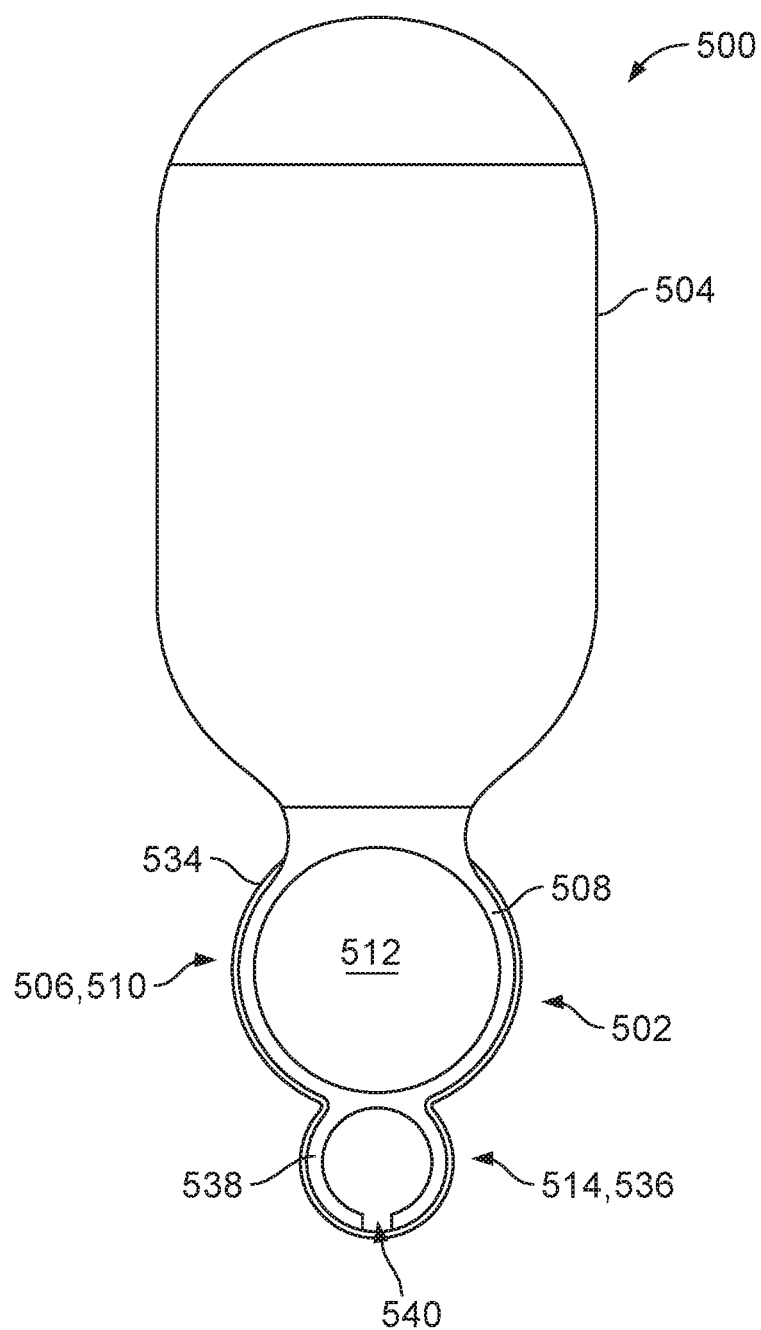
FIG. 20 is an end view of the operative cannula of FIG. 19.

Referring to FIGS. 19 and 20, the operative cannula 500 includes an elongate shaft 502, a handle portion 504 (e.g., a gripping member) extending from a proximal end 506 of the elongate shaft 502, and a sheath 534 (e.g., an outer, external sheath) that surrounds the elongate shaft 502. The elongate shaft 502 includes a tubular wall 508 that defines a proximal opening 510, a distal opening 516, and an interior pocket 512 that are sized to allow passage of the endoscopic cannula 101. Accordingly, the operative cannula 500 can be attached to the endoscopic cannula 101 by sliding the distal end 121 of the endoscopic cannula 101 into the proximal opening 510 of the tubular wall 508 and then advancing the endoscopic cannula 101 until the distal portion 105 of the endoscopic cannula 101 is positioned at the distal opening 516 or advancing the endoscopic cannula 101 through the distal opening 516 of the tubular wall 508 until the tubular wall 508 surrounds the endoscopic cannula 101 along a length of the tubular wall 508. In this manner, the operative cannula 500 can be easily slid onto the endoscopic cannula 101.

The elongate shaft 502 further includes a working channel 514 that extends along the tubular wall 508. The working channel 514 is formed from two wall portions 538 that together define a generally cylindrical tubular structure (i.e., with a generally circular cross-sectional shape) with an elongate opening 540. The working channel 514 extends from a proximal opening 536 to a distal opening 526 defined by a beveled edge 518 (e.g., an angled edge) aligned along one side with a distal end 520 of the elongate shaft 502. The working channel 514 is sized and flexible to allow passage of surgical instruments (e.g., surgical forceps, biopsy punches, surgical scissors, polyp snares, biopsy forceps, grasping forceps, bipolar electrodes, and cytology brushes) into the proximal opening 536 and out of the distal opening 526 for carrying out an intervention (e.g., operation or another procedure) within the uterine cavity of the patient. The beveled edge 518 of the working channel 514 is substantially similar in structure and function to the beveled edge 118 of the working channel 114 of the operative cannula 100, except that the beveled edge 518 is in part defined by the elongate opening 540 of the working channel 514.

A structure of the elongate shaft 502 (e.g., including the elongate opening 540), together with a material choice of the elongate shaft 502, provides the elongate shaft 502 with a flexibility that allows the wall portions 538 of the working channel 514 to spread apart (e.g., to expand) to accommodate a surgical instrument that has a width greater than a nominal internal diameter of the working channel 514 as the surgical instrument is passed into the proximal opening 536 and through the working channel 514. A nominal (e.g., collapsed) structure of the working channel 514 can accommodate a surgical instrument that has a width smaller than the nominal internal diameter of the working channel 514 as the surgical instrument is passed into the proximal opening 536 and through the working channel 514.

Due to the flexibility of the elongate shaft 502 and to a softness of the elongate shaft 102, the elongate shaft 502 is able to elastically (e.g., reversibly) deform (e.g., bend) to follow the nominal shape of the endoscopic cannula 101 as the operative cannula 500 is slid along the endoscopic cannula 101. For example, as the operative cannula 500 is slid onto the distal end 121 of the endoscopic cannula 101 or slid distally from the proximal portion 103 of the endoscopic cannula 101, the elongate shaft 502 can deform to follow the curve 107 of the endoscopic cannula 101. As the operative cannula 500 is slid proximally from the distal portion 105 of the endoscopic cannula 101, the elongate shaft 502 can regain its nominal, straight shape. Accordingly, the operative cannula 500 can advantageously be used with endoscopic cannulas having a variety of curvature profiles. Surgical instruments used with the operative cannula 500 are flexible enough to deform according to the shape of the working channel 514 as the surgical instruments are slid within the working channel 514 (e.g., as guided by the shape of the endoscopic cannula 101).

The sheath 534 snuggly surrounds the elongate shaft 502 along a portion of its length and can expand and collapse to accommodate the elongate shaft 502 according to a size of a surgical instrument passed through the working channel 514. The sheath 534 has a stiffness that is sufficient to limit the extent to which the wall portions 538 of the working channel 514 can expand, thereby maintaining a mechanical integrity of the working channel 514 (e.g., to prevent the wall portions 538 from fracturing, tearing, or otherwise failing). Furthermore, the sheath 534 is sufficiently soft and flexible to deform to a shape of the elongate shaft 502 (e.g., as determined by a structural profile of the elongate shaft 502 and as guided by the shape of the endoscopic cannula 101). A smoothness of the sheath 534 and coverage of edges of the wall portions 538 along the elongate opening 540 may also ease insertion of the operative cannula 500 through the cervix of the patient, thereby minimizing patient discomfort during use of the operative cannula 500. The handle portion 504 is formed as a tab that is sized to be grasped by a user (e.g., a clinician) of the operative cannula 500 to slide the operative cannula 500 proximally and distally along the endoscopic cannula 101.

In some embodiments, the operative cannula 500 includes a locking feature (e.g., provided by one or more detents, recesses, or other physical stops) positioned near the distal end 520 of the elongate shaft 502 that can mate with a corresponding locking feature positioned along the distal portion 105 of the endoscopic cannula 101 to secure the operative cannula 500 in place along the distal portion 105 of the endoscopic cannula 101 (e.g., to prevent the operative cannula 500 from sliding distally off of the endoscopic cannula 101). In some embodiments, the locking feature may be located along a central or other portion of the elongate shaft 502 to mate with a corresponding locking feature positioned along a central or other portion of the endoscopic cannula 101.

The elongate shaft 502 (e.g., including the tubular wall 508 and the working channel 514) of the operative cannula 500 typically has a length of about 101.6 mm to about 304.8 mm (e.g., about 177.8 mm) and a wall thickness of about 0.13 mm to about 2.00 mm (e.g., about 0.36 mm). The interior pocket 512 typically has a diameter of about 2.0 mm to about 30.0 mm (e.g., about 3.6 mm). The working channel 514 typically has an internal diameter of about 0.50 mm to about 20.00 mm (e.g., about 1.85 mm) and a wall thickness of about 0.13 mm to about 2.00 mm (e.g., about 0.36 mm). The elongate opening 540 of the working channel 514 typically has a nominal width of about 0.025 mm to about 0.770 mm (e.g., about 0.510 mm). The beveled edge 518 of the working channel 514 is typically oriented at an angle of about 5° to about 80° (e.g., about 35°) from a central axis of the elongate shaft 502. The gripping member 504 typically has a width of about 5.0 mm to about 11.4 mm (e.g., about 7.6 mm), a thickness of about 5.0 mm to about 9.5 mm (e.g., about 6.4 mm), and a length of about 10.0 mm to about 20.6 mm (e.g., about 13.7 mm). The sheath 534 typically has a thickness of about 0.04 mm to about 0.20 mm (e.g., about 0.13 mm), and a length of about 101.6 mm to about 243.8 mm (e.g., about 162.5 mm).

A body of the operative cannula 500 (e.g., including the elongate shaft 502 and the handle portion 504) may be manufactured via one or more techniques including injection molding, extrusion, casting, machining, SLA, and FDM. The body of the operative cannula 500 is typically made of one or materials that are relatively soft and/or that have a relatively high elasticity, such as polypropylene, nylon, PTFE, silicone, latex rubber, ABS, polycarbonate, polystyrene, and PEBA. Such materials typically have a hardness in a range of about 0 Shore A to about 100 Shore A. The elongate shaft 502 and the handle portion 504 may be made of the same one or more materials or made of different, respective materials. The sheath 534 of the operative cannula 500 is typically made of one or materials that are relatively soft and/or that have a relatively high elasticity, such as urethane, braided fiber, woven fiber, silicone, or polypropylene.

A clinician can use the operative cannula 500 to perform an intervention within a uterine cavity of a patient to further examine, treat, remove, or manipulate an abnormality, an anatomical feature of interest, a healthy tissue, a foreign body, or a misplaced device. For example, as described above with respect to the operative cannula 100 and with respect to FIG. 5, a clinician uses a handset attached to the endoscopic cannula 101 to insert the endoscopic cannula 101 into a cervix 109 of the patient. The clinician advances the endoscopic cannula 101 distally until the distal portion 105 of the endoscopic cannula 101 is positioned at a desired location and at a desired orientation within a uterine cavity 111 of the patient.

Upon viewing an abnormality 113 via a video stream or via one or more images captured by the endoscopic cannula 101 (displayed on a monitor of the handset) and deciding to perform an operation (e.g., a biopsy procedure, a polypectomy, an excision, or a cautery) within the uterine cavity 111 to further examine or to treat the abnormality 113, the clinician withdraws the endoscopic cannula 101 from the patient. The clinician slides the operative cannula 500 onto the endoscopic cannula 101 and positions the operative cannula 500 along the proximal portion 103 of the endoscopic cannula 101. With the operative cannula 500 positioned along the proximal portion 105 of the endoscopic cannula 101, the clinician reinserts the endoscopic cannula 101 into the cervix 109 of the patient and advances the endoscopic cannula 101 distally until the distal portion 105 of the endoscopic cannula 101 is positioned at a desired location and at a desired orientation within the uterine cavity 111 according to a location of the abnormality 113.

The clinician moves the operative cannula 500 distally along the endoscopic cannula 101 and positions the operative cannula 500 within the uterine cavity 111, as described above with respect to the operative cannula 100 and with respect to FIG. 7. The clinician then inserts a surgical instrument 117 into the proximal opening 536 of the working channel 514 and slides the surgical instrument 117 distally within the working channel 514 until the surgical instrument 117 exits the beveled edge 518 of the working channel 514 and is delivered into the uterine cavity 111, as described above with respect to the operative cannula 100 and with respect to FIG. 8. The clinician manipulates the surgical instrument 117 to perform the operation within the uterine cavity 111. Upon completion of the operation, the clinician withdraws the surgical instrument 117 from the working channel 514 through the proximal opening 536 of the working channel 514, as described above with respect to the operative cannula 100 and with respect to FIG. 9. Once the surgical instrument 117 has been removed from the working channel 514, the clinician may then make additional observations of the uterine cavity 111 with the operative cannula 500 positioned along the distal portion 105 of the endoscopic cannula 101 or with the operative cannula 500 withdrawn to the proximal portion 103 of the endoscopic cannula 101 (as described above with respect to the operative cannula 100 and with respect to FIG. 10).

Upon completion of the operation and with the operative cannula 500 attached to the endoscopic cannula 101, the clinician withdraws the endoscopic cannula 101 from the cervix 109 of the patient. The operative cannula 500 is then slid off of the endoscopic cannula 101 and disposed of according to standard protocols. In some instances, upon performing the operation, the clinician withdraws the endoscopic cannula 101 (e.g., carrying the operative cannula 500) and the surgical instrument 117 while the surgical instrument 117 is still disposed within the working channel 514, as described above with respect to the operative cannula 100.

In some cases, the operative cannula 500 may be used in a procedure for removing a foreign body or for retrieving a misplaced device (e.g., for passing an instrument within the working channel 514 that can be used to remove the foreign body or to retrieve the device) from the uterine cavity 111, as described above with respect to the operative cannula 100.

The operative cannula 500 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 500 can enable procedures that would otherwise be performed in a hospital to be performed in a physician's office or in a clinic, as discussed above with respect to the operative cannula 100. The operative cannula 500 can be packaged individually, and both the operative cannula 500 and the packaging will remain sterile for a shelf-life of the operative cannula 500.

Figure 21:
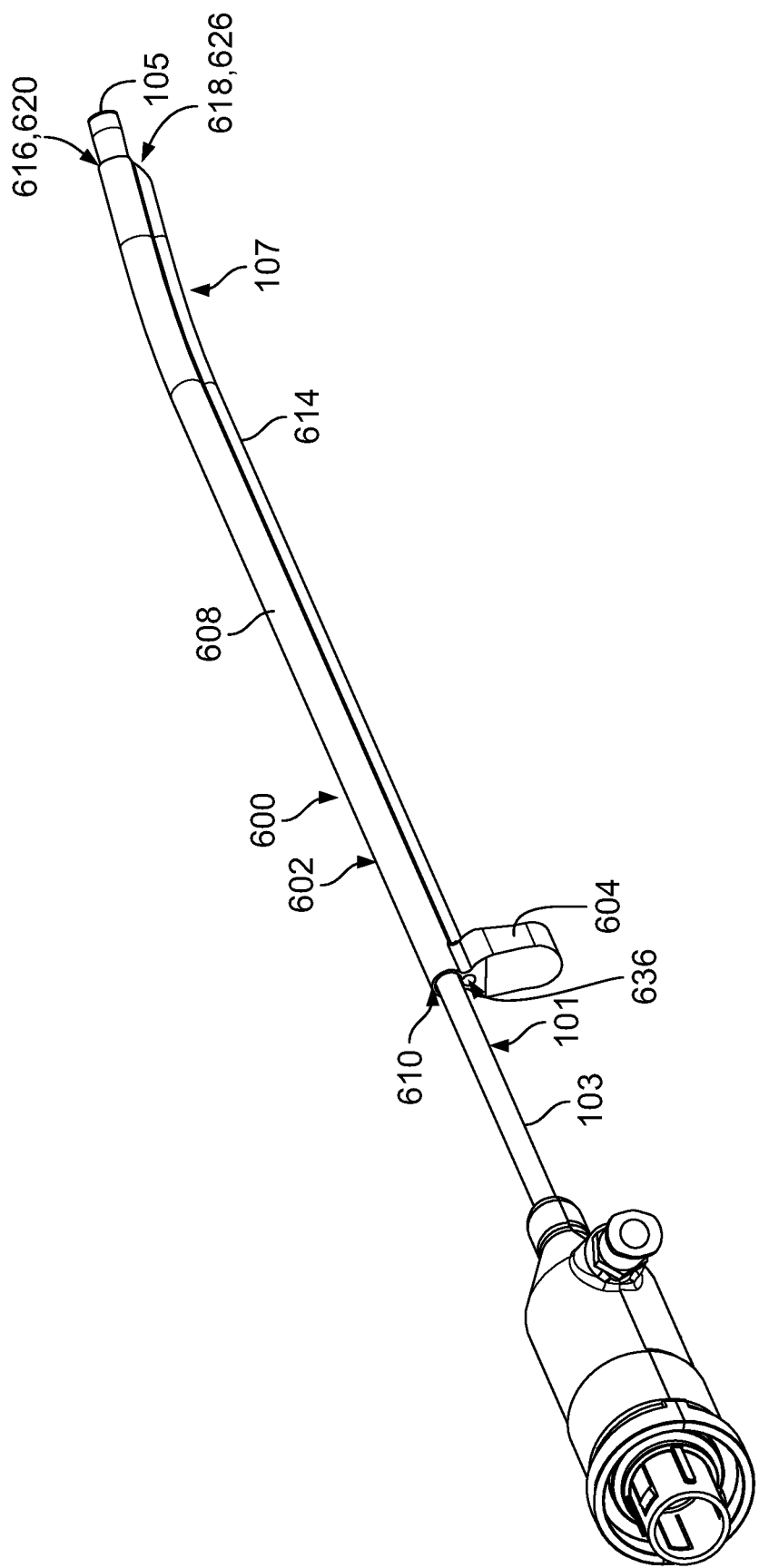
FIG. 21 is a perspective view of an operative cannula that includes a closed tubular wall and a fixed-diameter working channel, positioned along the distal portion of the endoscopic cannula of FIG. 1.

While the operative cannula 500 has been described as including the expandable working channel 514 and the closed wall 508 that can be slid onto the distal end 121 of the endoscopic cannula 101, in some embodiments, an operative cannula includes a closed wall that can be slid onto the distal end 121 of the endoscopic cannula 101 and a fixed-diameter working channel. For example, FIG. 21 illustrates an operative cannula 600 that includes such features. Like the operative cannulas 100, 200, 300, 400, 500, the operative cannula 600 is a disposable device that is configured to allow passage of a surgical instrument along the endoscopic cannula 101 and into a uterine cavity for performing an intervention within the uterine cavity. The operative cannula 600 is configured to be slid onto the distal end 121 of the endoscopic cannula 101 and subsequently slid between the distal portion 105 of the endoscopic cannula 101 (as shown in FIG. 21) and the proximal portion 103 of the endoscopic cannula. Example interventions that can be performed using the operative cannula 600 include device retrievals, operative procedures (e.g., surgical procedures), and other procedures.

Figure 22:
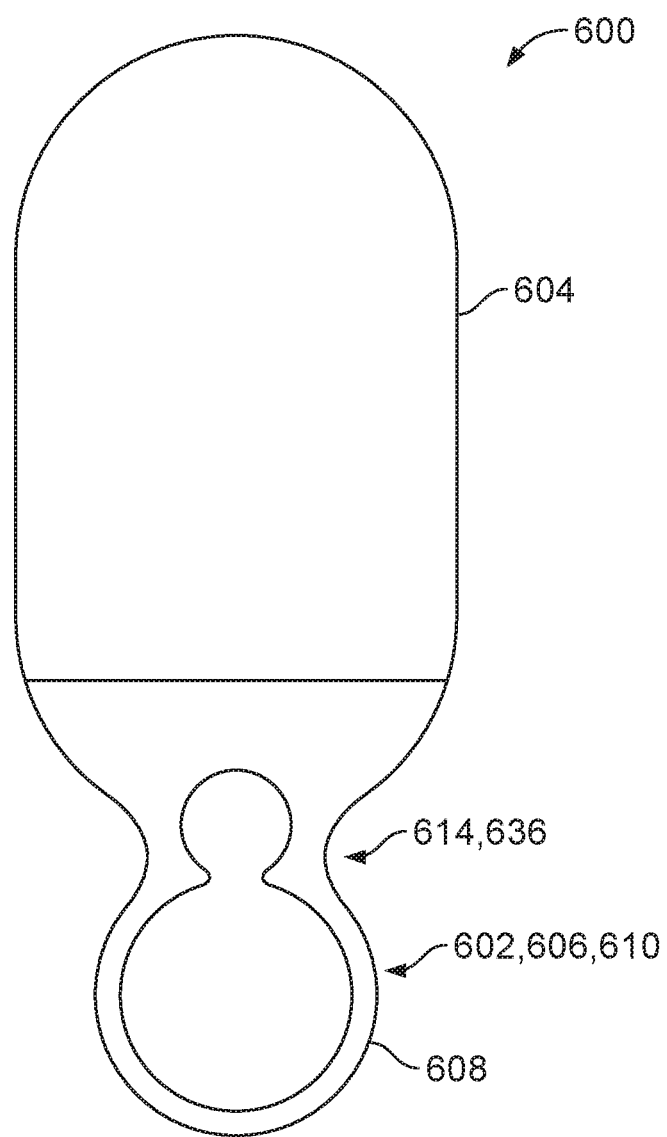
FIG. 22 is an end view of the operative cannula of FIG. 21.

Referring to FIGS. 21 and 22, the operative cannula 600 includes an elongate shaft 602 that is substantially similar in structure and function to the elongate shaft 502 of the operative cannula 500, except that a working channel 614 of the elongate shaft 602 is formed as a fixed-diameter channel that does not define an elongate opening. As described above with respect to the operative cannula 500, the operative cannula 600 can be attached to the endoscopic cannula 101 by sliding the distal end 121 of the endoscopic cannula 101 into a proximal opening 610 of a tubular wall 608 of the elongate shaft 602 and then advancing the endoscopic cannula 101 through a distal opening 616 of the tubular wall 608 until the tubular wall 608 surrounds the endoscopic cannula 101 along a length of the tubular wall 608. In this manner, the operative cannula 600 can be easily slid onto the endoscopic cannula 101.

The working channel 614 of the elongate shaft 602 extends from a proximal opening 636 to a distal opening 626 defined by a beveled edge 618 (e.g., an angled edge) aligned along one side with a distal end 620 of the elongate shaft 602. The working channel 614 is sized to allow passage of surgical instruments (e.g., surgical forceps, biopsy punches, surgical scissors, polyp snares, biopsy forceps, grasping forceps, bipolar electrodes, and cytology brushes) into the proximal opening 636 and out of the distal opening 626 for carrying out an intervention (e.g., operation or another procedure) within the uterine cavity of the patient. The beveled edge 618 of the working channel 614 is substantially similar in structure and function to the beveled edge 118 of the working channel 114 of the operative cannula 100.

Due to a flexibility of the elongate shaft 602 and to a softness of the elongate shaft 602, the elongate shaft 602 is able to elastically (e.g., reversibly) deform (e.g., bend) to follow the nominal shape of the endoscopic cannula 101 as the operative cannula 600 is slid along the endoscopic cannula 101, as discussed above with respect to the operative cannula 500. Accordingly, the operative cannula 600 can advantageously be used with endoscopic cannulas having a variety of curvature profiles. Surgical instruments used with the operative cannula 600 are flexible enough to deform according to the shape of the working channel 614 as the surgical instruments are slid within the working channel 514 (e.g., as guided by the shape of the endoscopic cannula 101).

The operative cannula 600 also includes a handle portion 604 (e.g., a gripping member) extending from a proximal end 606 of the elongate shaft 602. The handle portion 604 of the operative cannula 600 is substantially similar in structure and function to the handle portion 504 of the operative cannula 500.

In some embodiments, the operative cannula 600 includes a locking feature (e.g., provided by one or more detents, recesses, or other physical stops) positioned near the distal end 620 of the elongate shaft 602 that can mate with a corresponding locking feature positioned along the distal portion 105 of the endoscopic cannula 101 to secure the operative cannula 600 in place along the distal portion 105 of the endoscopic cannula 101 (e.g., to prevent the operative cannula 600 from sliding distally off of the endoscopic cannula 101). In some embodiments, the locking feature may be located along a central or other portion of the elongate shaft 602 to mate with a corresponding locking feature positioned along a central or other portion of the endoscopic cannula 101.

The operative cannula 600 may be manufactured via the one or more techniques indicated above with respect to the operative cannula 500. The operative cannula 600 may have a material formulation as described above with respect to a material formulation of the body of the operative cannula 500. Such materials typically have a hardness in a range of about 0 Shore A to about 100 Shore A.

A clinician can use the operative cannula 600 to perform an intervention within a uterine cavity of a patient to further examine, treat, remove, or manipulate an abnormality, an anatomical feature of interest, a healthy tissue, a foreign body, or a misplaced device according to the steps described above with respect to the operative cannula 500 and with respect to FIGS. 5 and 7-10. The operative cannula 600 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 600 can enable procedures that would otherwise be performed in a hospital to be performed in a physician's office or in a clinic, as discussed above with respect to the operative cannula 100. The operative cannula 600 can be packaged individually, and both the operative cannula 600 and the packaging will remain sterile for a shelf-life of the operative cannula 600.

Figure 23:
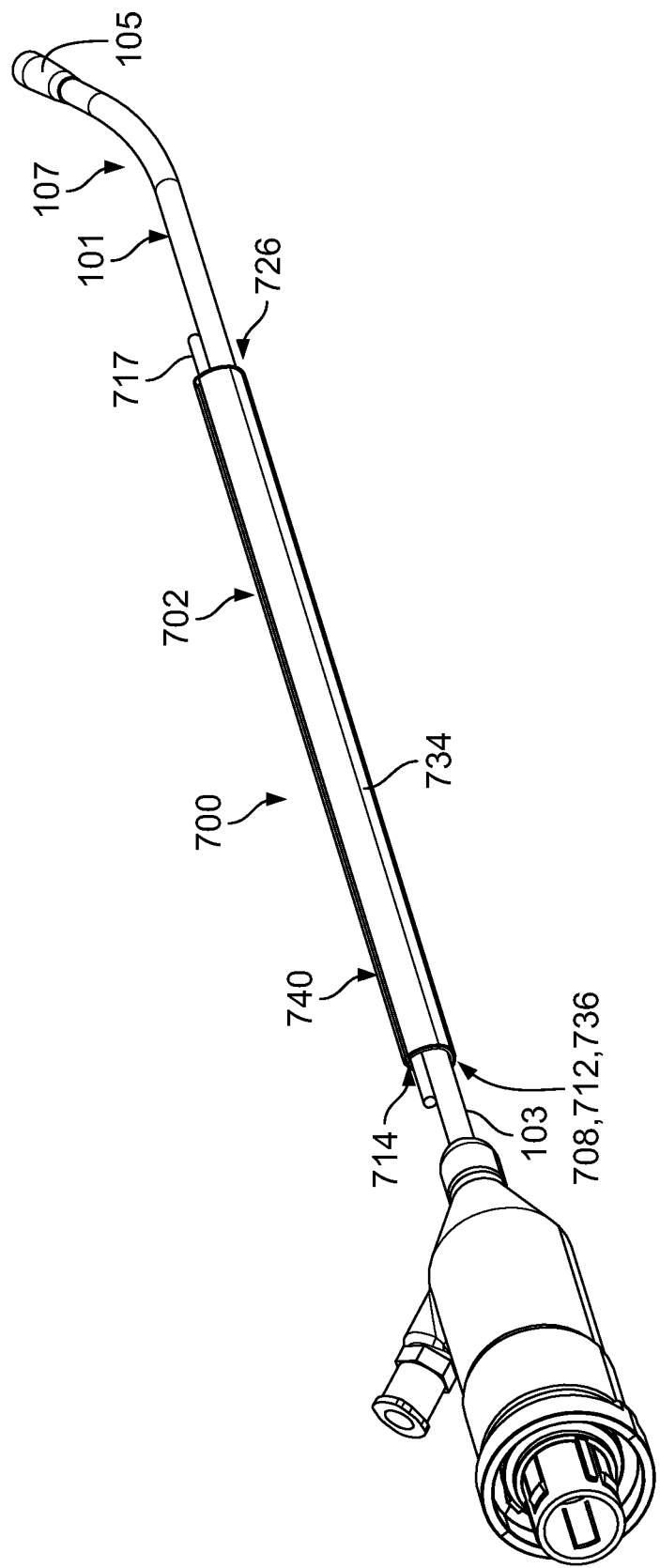
FIG. 23 is a perspective view of an operative cannula that includes a single, expandable wall that accommodates both a surgical instrument and an endoscopic cannula, positioned along the proximal portion of the endoscopic cannula of FIG. 1.

While the operative cannula 500 has been described and illustrated as including the expandable working channel 514 and the closed wall 508 that provide separate spaces, in some embodiments, an operative cannula includes a single, expandable wall that accommodates both a surgical instrument and the endoscopic cannula 101. For example, FIG. 23 illustrates an operative cannula 700 that includes such features. Like the operative cannulas 100, 200, 300, 400, 500, 600 the operative cannula 700 is a disposable device that is configured to allow passage of a surgical instrument along the endoscopic cannula 101 and into a uterine cavity for performing an intervention within the uterine cavity. The operative cannula 700 is configured to be slid onto the distal end 121 of the endoscopic cannula 101 and subsequently slid between the distal portion 105 of the endoscopic cannula 101 and the proximal portion 103 of the endoscopic cannula (as shown in FIG. 23). Example interventions that can be performed using the operative cannula 700 include device retrievals, operative procedures (e.g., surgical procedures), and other procedures.

Figure 24:
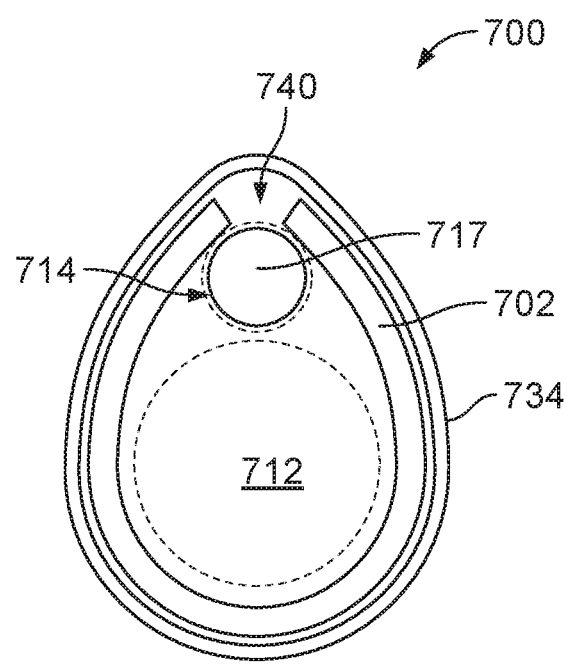
FIG. 24 is an end view of the operative cannula of FIG. 23.

Referring to FIGS. 23 and 24, the operative cannula 700 includes an elongate shaft 702 and a sheath 734 that is substantially similar in structure and function to the sheath 534 of the operative cannula 500. As described above with respect to the operative cannula 500, the operative cannula 700 can be attached to the endoscopic cannula 101 by sliding the distal end 121 of the endoscopic cannula 101 into a proximal opening 710 of the elongate shaft 702 and then advancing the endoscopic cannula 101 through a distal opening 726 of the elongate shaft 702 until the elongate shaft 702 surrounds the endoscopic cannula 101 along a length of the elongate shaft 702. In this manner, the operative cannula 700 can be easily slid onto the endoscopic cannula 101.

The elongate shaft 702 is formed as a flexible wall that can spread apart (e.g., a clamshell) to accommodate the endoscopic cannula 101 and a surgical instrument of a variable width or diameter. The elongate shaft 702 defines an interior channel 708 that has a generally teardrop shaped cross-sectional area. The interior channel 608 extends from a first opening 736 and to a second opening 726 of the elongate shaft 702. The openings 726, 736 are substantially similar in structure and can each therefore serve as a proximal opening or a distal opening. A first portion of the interior channel 708 forms an interior pocket 712 and is sized to allow passage of the endoscopic cannula 101. A second portion of the interior channel 708 forms a working channel 714 and is sized to allow passage of a surgical instrument 717. The elongate shaft 702 further defines an elongate opening 740 at which the elongate shaft 702 can spread apart or collapse to accommodate the surgical instrument 717. The working channel 714 is sized and flexible to allow passage of surgical instruments (e.g., surgical forceps, biopsy punches, surgical scissors, polyp snares, biopsy forceps, grasping forceps, bipolar electrodes, and cytology brushes) of a variable width or diameter into one of the openings 726, 736 and out of the other of the openings 726, 736 for carrying out an intervention (e.g., operation or another procedure) within the uterine cavity of the patient.

A structure of the elongate shaft 702 (e.g., including the elongate opening 740), together with a material choice of the elongate shaft 702, provides the elongate shaft 702 with a flexibility that allows the elongate shaft 702 to spread apart (e.g., to expand) to accommodate a surgical instrument 717 that has a width greater than a nominal internal width of the working channel 714 as the surgical instrument 717 is passed into one of the openings 726, 736. A nominal (e.g., collapsed) structure of the elongate shaft 702 can accommodate a surgical instrument 717 that has a width smaller than the nominal internal width of the working channel 714 as the surgical instrument 717 is passed into one of the openings 726, 736.

Due to the flexibility of the elongate shaft 702 and to a softness of the elongate shaft 702, the elongate shaft 702 is able to elastically (e.g., reversibly) deform (e.g., bend) to follow the nominal shape of the endoscopic cannula 101 as the operative cannula 700 is slid along the endoscopic cannula 101. Accordingly, the operative cannula 700 can advantageously be used with endoscopic cannulas having a variety of curvature profiles. A surgical instrument 717 used with the operative cannula 700 is flexible enough to deform according to the shape of the working channel 714 as the surgical instrument 717 is slid within the working channel 714 (e.g., as guided by the shape of the endoscopic cannula 101).

The sheath 734 surrounds the elongate shaft 702 along its length and can expand and collapse to snuggly accommodate the elongate shaft 702 according to a size of a surgical instrument 717 passed through the working channel 714. The sheath 734 has a stiffness that is sufficient to limit the extent to which the elongate shaft 702 can spread apart, thereby maintaining a mechanical integrity of the elongate shaft 702 (e.g., to prevent the elongate shaft 702 form fracturing, tearing, or otherwise failing). Furthermore, the sheath 734 is sufficiently soft and flexible to deform to a shape of the elongate shaft 702 (e.g., as determined by a structural profile of the elongate shaft 702 and as guided by the shape of the endoscopic cannula 101). A smoothness of the sheath 734 and coverage of edges of the elongate shaft 702 along the elongate opening 740 may also ease insertion of the operative cannula 700 through a cervix of the patient, thereby minimizing patient discomfort during use of the operative cannula 700.

In some embodiments, the operative cannula 700 includes a locking feature (e.g., provided by one or more detents, recesses, or other physical stops) positioned near one of the openings 726, 736 of the elongate shaft 702 that can mate with a corresponding locking feature positioned along the distal portion 105 of the endoscopic cannula 101 to secure the operative cannula 700 in place along the distal portion 105 of the endoscopic cannula 101 (e.g., to prevent the operative cannula 700 from sliding distally off of the endoscopic cannula 101). In some embodiments, the locking feature may be located along a central or other portion of the elongate shaft 702 to mate with a corresponding locking feature positioned along a central or other portion of the endoscopic cannula 101.

The elongate shaft 702 of the operative cannula 700 typically has a length of about 101.6 mm to about 304.8 mm (e.g., about 177.8 mm) and a wall thickness of about 0.13 mm to about 2.00 mm (e.g., about 0.36 mm). The interior channel 708 typically has a maximum width (e.g., defining a diameter of the interior pocket 712) of about 0.5 mm to about 20.0 mm (e.g., about 3.5 mm). The interior channel 708 typically has a minimum width (e.g., defining a nominal width of the elongate opening 740) of about 0.07 mm to about 1.00 mm (e.g., about 0.25 mm). The sheath 734 typically has a thickness of about 0.020 mm to about 2.000 mm (e.g., about 0.178 mm), and a length that is about equal to the length of the elongate shaft 702.

The elongate shaft 702 of the operative cannula 700 may be manufactured via the one or more techniques indicated above with respect to the elongate shaft 502 of the operative cannula 500. The elongate shaft 702 may a have material formulation as described above with respect to a material formulation of the elongate shaft 502. Such materials typically have a hardness in a range of about 0 Shore A to about 100 Shore A. The sheath 734 may a have material formulation as described above with respect to a material formulation of the sheath 534.

A clinician can use the operative cannula 700 to perform an intervention within a uterine cavity of a patient to further examine, treat, remove, or manipulate an abnormality, an anatomical feature of interest, a healthy tissue, a foreign body, or a misplaced device. For example, as described above with respect to the operative cannula 100 and with respect to FIG. 5, a clinician uses a handset attached to the endoscopic cannula 101 to insert the endoscopic cannula 101 into a cervix 109 of the patient. The clinician advances the endoscopic cannula 101 distally until the distal portion 105 of the endoscopic cannula 101 is positioned at a desired location and at a desired orientation within a uterine cavity 111 of the patient.

Upon viewing an abnormality 113 via a video stream or via one or more images captured by the endoscopic cannula 101 (displayed on a monitor of the handset) and deciding to perform an operation (e.g., a biopsy procedure, a polypectomy, an excision, or a cautery) within the uterine cavity 111 to further examine or to treat the abnormality 113, the clinician withdraws the endoscopic cannula 101 from the patient. The clinician slides the operative cannula 700 onto the endoscopic cannula 101 and positions the operative cannula 700 within the interior pocket 712 of the elongate shaft 702 along the proximal portion 103 of the endoscopic cannula 101. With the operative cannula 700 positioned along the proximal portion 105 of the endoscopic cannula 101, the clinician reinserts the endoscopic cannula 101 into the cervix 109 of the patient and advances the endoscopic cannula 101 distally until the distal portion 105 of the endoscopic cannula 101 is positioned at a desired location and at a desired orientation within the uterine cavity 111 according to a location of the abnormality 113.

The clinician moves the operative cannula 700 distally along the endoscopic cannula 101 and positions the operative cannula 700 within the uterine cavity 111, as described above with respect to the operative cannula 100 and with respect to FIG. 7. The clinician then inserts a surgical instrument 117 into the opening 726, 736 of the elongate shaft 702 that is proximal to the clinician and within the working channel 714 and slides the surgical instrument 117 distally within the working channel 714 until the surgical instrument 117 exits the other opening 726, 736 of the elongate shaft, as described above with respect to the operative cannula 100 and with respect to FIG. 8. The clinician manipulates the surgical instrument 117 to perform the operation within the uterine cavity 111. Upon completion of the operation, the clinician withdraws the surgical instrument 117 from the working channel 714 through the opening 726, 736 of the elongate shaft 702 that is proximal to the clinician, as described above with respect to the operative cannula 100 and with respect to FIG. 9. The clinician may then make additional observations of the uterine cavity 111 with the operative cannula 700 positioned along the distal portion 105 of the endoscopic cannula 101 or with the operative cannula 700 withdrawn to the proximal portion 103 of the endoscopic cannula 101 (as described above with respect to the operative cannula 100 and with respect to FIG. 10).

Upon completion of the operation and with the operative cannula 700 attached to the endoscopic cannula 101, the clinician withdraws the endoscopic cannula 101 from the cervix 109 of the patient. The operative cannula 700 is then slid off of the endoscopic cannula 101 and disposed of according to standard protocols. In some instances, upon performing the operation, the clinician withdraws the endoscopic cannula 101 (e.g., carrying the operative cannula 700) and the surgical instrument 117 from the cervix 109 while the surgical instrument 117 is still disposed within the working channel 714, as described above with respect to the operative cannula 100.

In some cases, the operative cannula 700 may be used in a procedure for removing a foreign body or for retrieving a misplaced device (e.g., for passing an instrument within the working channel 714 that can be used to remove the foreign body or to retrieve the device) from the uterine cavity 111, as described above with respect to the operative cannula 100.

The operative cannula 700 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 700 can enable procedures that would otherwise be performed in a hospital to be performed in a physician's office or in a clinic, as discussed above with respect to the operative cannula 100. The operative cannula 700 can be packaged individually, and both the operative cannula 700 and the packaging will remain sterile for a shelf-life of the operative cannula 700.

Figure 25:
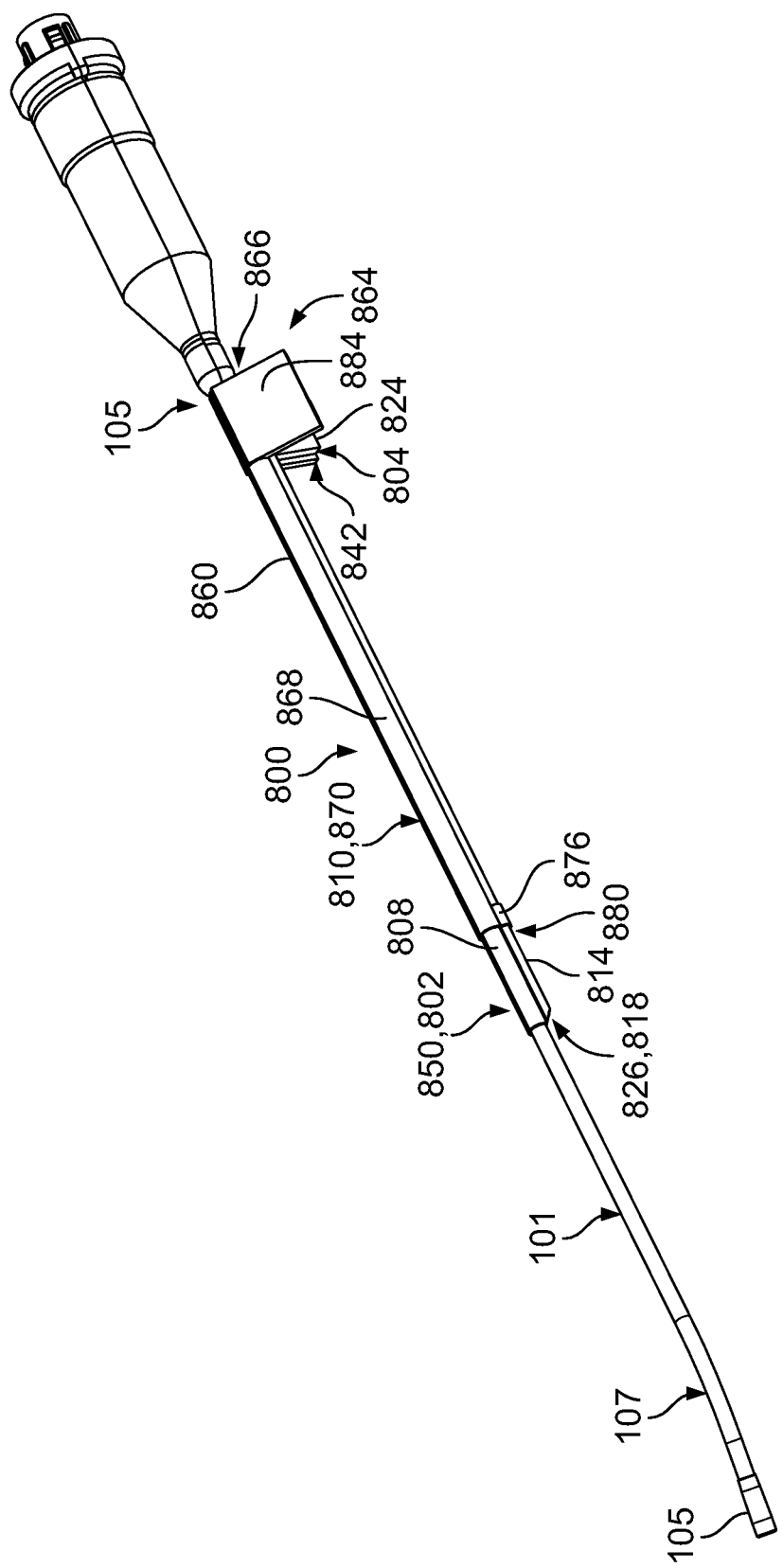
FIG. 25 is a perspective view of an operative cannula that includes a telescopic shaft in a retracted configuration along the endoscopic cannula of FIG. 1.
Figure 26:
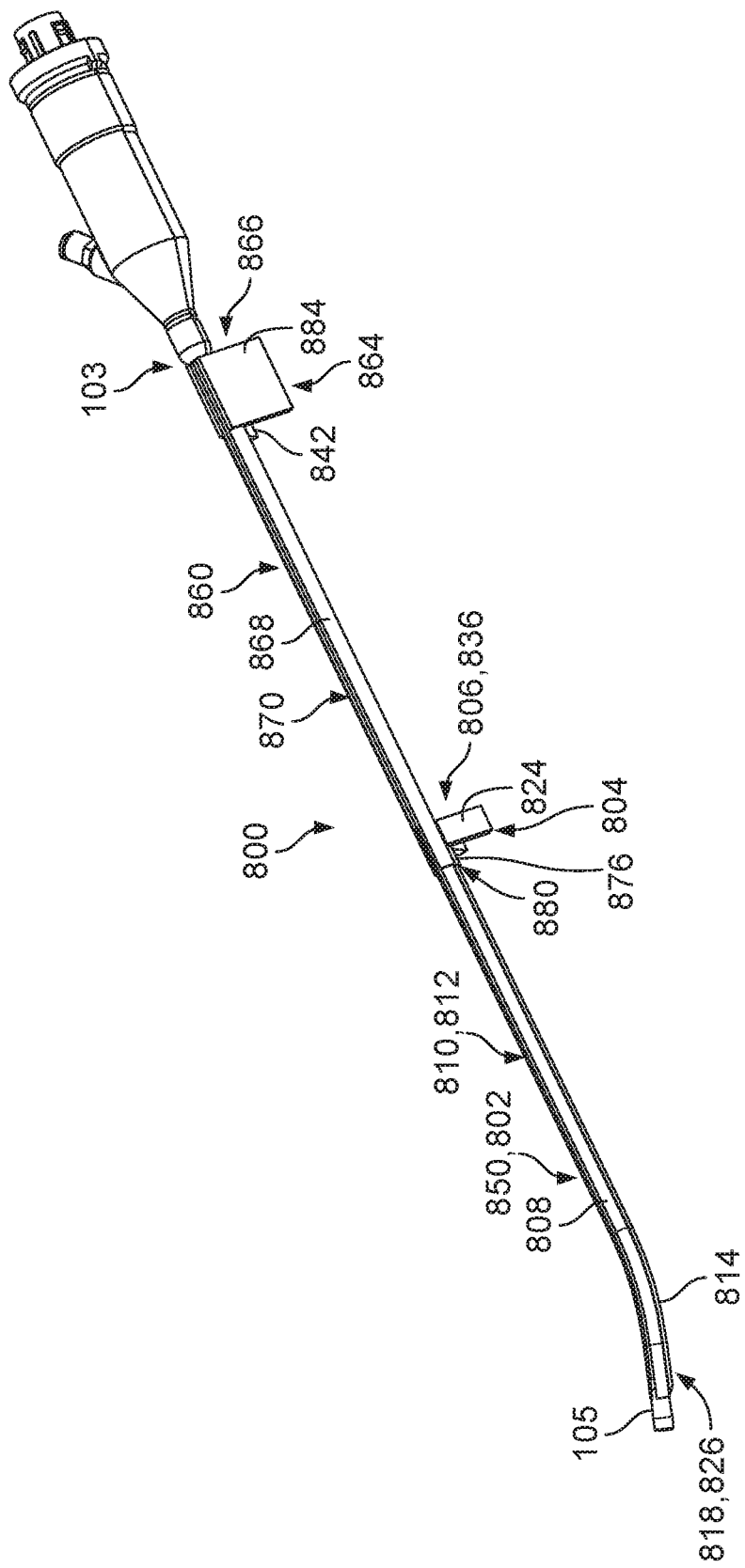
FIG. 26 is a perspective view of the operative cannula of FIG. 25 in an extended configuration along the endoscopic cannula of FIG. 1.

While the operative cannulas 100, 200, 300, 400, 500, 600, 700 have been described and illustrated as fixed-length cannulas, in some embodiments, an operative cannula has an adjustable length. For example, FIGS. 25 and 26 illustrate an operative cannula 800 that includes a telescopic shaft. Like the operative cannulas 100, 200, 300, 400, 500, 600, 700, the operative cannula 800 is a disposable device that is configured to allow passage of a surgical instrument along the endoscopic cannula 101 and into a uterine cavity for performing an intervention within the uterine cavity. Like the operative cannulas 100, 200, 300, 400, the operative cannula 800 is configured to be attached to (e.g., clipped onto) the endoscopic cannula 101. The operative cannula 800 be telescopically adjusted to place the operative cannula 800 in a retracted configuration (refer to FIG. 25) or in an extended configuration (refer to FIG. 26). In the retracted configuration, the operative cannula 800 is short enough in length to allow the operative cannula 800 to be clipped onto the proximal portion 103 of the endoscopic cannula 101 without having to remove (e.g., withdraw) the endoscopic cannula 101 from the patient. Example interventions that can be performed using the operative cannula 800 include device retrievals, operative procedures (e.g., surgical procedures), and other procedures.

Figure 27:
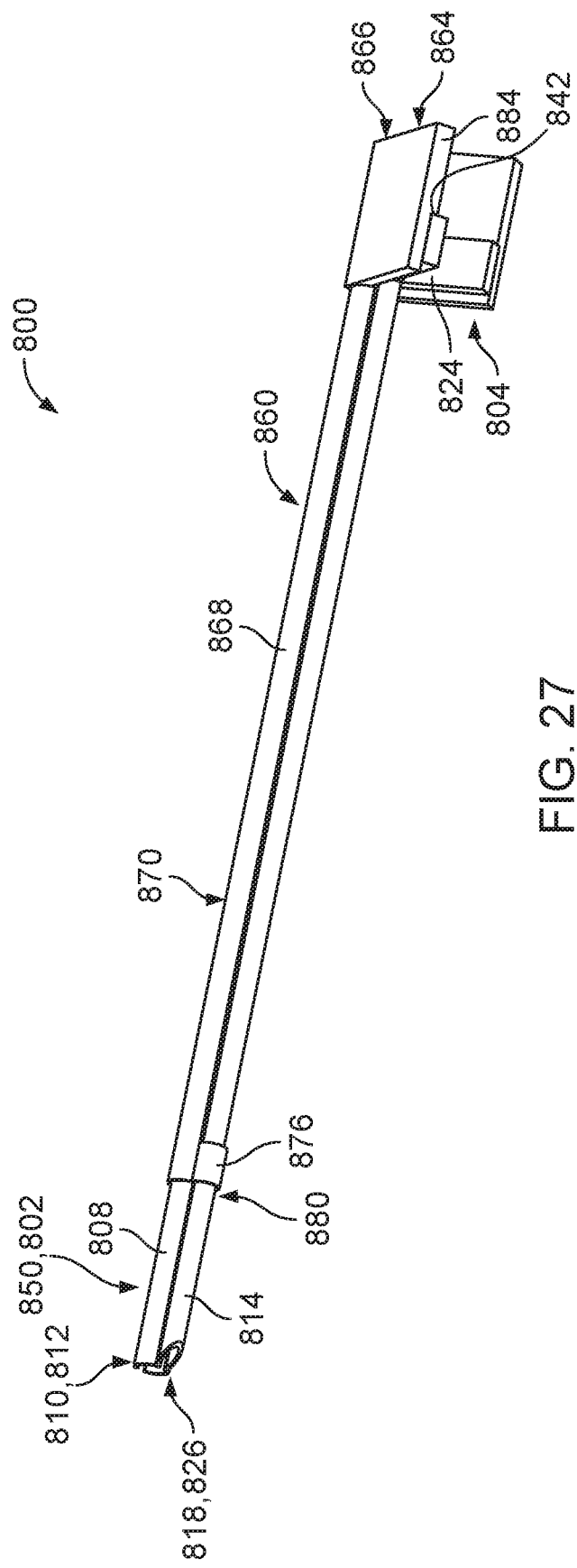
FIG. 27 is a perspective view of the operative cannula of FIG. 25.

Referring to FIG. 27, the operative cannula 800 includes an inner cannula 850 and an outer guide 860 that surrounds the inner cannula 850. The inner cannula 850 is substantially similar in structure and function to the operative cannula 100, except that the inner guide 850 does not include a lateral entry port. Accordingly, the inner guide 850 includes an elongate shaft 802 that is substantially similar in structure and function to the elongate shaft 102 of the operative cannula 100. The inner guide 850 also includes a handle portion 804 extending from a proximal end 806 of the elongate shaft 802 that is similar in structure and function to the handle portion 104 of the operative cannula 100. The inner cannula 850 is slidable axially with respect to the outer guide 860.

The outer guide 860 includes wall portions 868 that together form a generally cylindrical tubular structure that surrounds wall portions 808 of the elongate shaft 802. The wall portions 868 define an exterior opening 870 that is aligned with an exterior opening 810 defined by the wall portions 808 of the elongate shaft 802. The outer guide 860 also includes an arc-shaped support 876 that extends from a distal end 880 of the outer guide 860. The support 876 surrounds a working channel 814 of the elongate shaft 802 and ensures that the outer guide 860 remains secured to the elongate shaft 802 as the inner cannula 850 is moved axially with respect to the outer guide 860. The outer guide 860 further includes a handle portion 864 that is similar in structure and function to the handle portion 104 of the operative cannula 100. Accordingly, the handle portion 864 includes two tabs 884 that together form a clip attached to the wall portions 868 of the outer guide 860. The tabs 884 includes recesses 842 in which the handle portion 804 can be seated. Accordingly, the recesses 842 have a profile (e.g., a rectangular profile) that is complimentary to a profile of the handle portion 804 and serve as a stop that limits proximal movement of the inner cannula 850 with respect to the outer guide 860.

The outer guide 860 also includes a locking feature (e.g., provided by one or more detents, recesses, or other physical stops) positioned near a proximal end 866 of the outer guide 860 that can mate with a corresponding locking feature positioned along the proximal portion 103 of the endoscopic cannula 101 to secure the operative cannula 800 in place along the proximal portion 103 of the endoscopic cannula 101. Such a locking feature positioned along the proximal portion 103 of the endoscopic cannula 101 may, in some cases, be easier to manufacture than a locking features positioned along the distal portion 105 of the endoscopic cannula 101 for use with operative cannulas that do not have a telescopic capability.

Referring to FIG. 25, the operative cannula 800 can be placed in the retracted configuration (e.g., a retracted length configuration) in which the handle portion 804 of the inner cannula 850 is seated within the recesses 842 of the handle portion 864 of the outer guide 860 such that the inner cannula 850 is located at a proximal position. Referring to FIG. 26, the operative cannula 800 can also be placed in the extended configuration (e.g., an extended length configuration) in which the handle portion 804 of the inner cannula 850 is abutted against the support 876 of the outer guide 860 such that the inner cannula 850 is located at a distal position. With the outer guide 860 attached (e.g., fixed) to the proximal portion 103 of the endoscopic cannula, the inner cannula 850 can be slid axially between the proximal position and the distal position to place the operative cannula 800 in the retracted configuration or the extended configuration, respectively. In this regard, the operative cannula 800 is configured as a one-stage (e.g., single-stage) telescopic device that includes one defined extended configuration that results from an abutment of the handle portion 804 of the inner guide 850 with the support 876 of the outer guide 860.

The inner cannula 850 and the outer guide 860 have a flexibility that allows the wall portions 808, 860 to spread apart (e.g., to be forced or pulled apart) to allow passage of the endoscopic cannula 101 through the exterior openings 810, 870 and into an interior pocket 812 of the elongate shaft 802. Therefore, the operative cannula 800 can be attached to (e.g., clipped onto) the endoscopic cannula 101 by aligning the endoscopic cannula 101 parallel to the operative cannula 800 and pressing the endoscopic cannula 101 against the exterior openings 810, 870 until the endoscopic cannula 101 forces the wall portions 808, 868 apart and snaps into the interior pocket 812 of the elongate shaft 802.

For example, the tabs 824, 884 can be urged (e.g., squeezed or pinched) together to pull the wall portions 808, 868 apart to widen the openings 810, 870 of the elongate shaft 802 and the outer guide 860 to facilitate entry of the endoscopic cannula 101 into the interior pocket 812 of the operative cannula 800 or to facilitate exit of endoscopic cannula 101 from the interior pocket 812 of the operative cannula 800. The user can urge the tabs 824, 884 together to widen the operative cannula 800 near the proximal ends 806, 866 of the elongate shaft 802 and the outer guide 860 and then place the widened, proximal portion of the operative cannula 800 around the endoscopic cannula 101. From an urged position, the tabs 824, 884 can be released to allow the wall portions 808, 868 to approach each other around the endoscopic cannula 101 to facilitate attachment of the operative cannula 800 to the endoscopic cannula 101. With the proximal portion of the operative cannula 800 attached to the endoscopic cannula 101, the user can use his or her fingers to guide a remaining portion of the operative cannula 800 onto the endoscopic cannula 101. In this manner, the operative cannula 800 can be easily clipped onto the endoscopic cannula 101.

Due to a flexibility of the elongate shaft 802 and to a softness of the elongate shaft 802, the elongate shaft 802 is able to elastically (e.g., reversibly) deform (e.g., bend) to follow the nominal shape of the endoscopic cannula 101 as the inner cannula 850 is slid along the endoscopic cannula 101, as discussed above with respect to the operative cannula 100. Accordingly, the operative cannula 800 can advantageously be used with endoscopic cannulas having a variety of curvature profiles. Surgical instruments used with the operative cannula 800 are flexible enough to deform according to the shape of the working channel 814 as the surgical instruments are slid within the working channel 814 (e.g., as guided by the shape of the endoscopic cannula 101).

The elongate shaft 802 (e.g., including the wall portions 808 and the working channel 814) of the inner cannula 850 typically has a length of about 101.6 mm to about 304.8 mm (e.g., about 177.8 mm). The cylindrical tube provided by the wall portions 808 typically has a nominal internal diameter (e.g., defining a diameter of the interior pocket 812) of about 2.0 mm to about 30.0 mm (e.g., about 3.6 mm) and a wall thickness of about 0.13 mm to about 2.00 mm (e.g., about 0.36 mm) such that the interior pocket 812 can surround the endoscopic cannula 101. The exterior opening 810 of the elongate shaft 802 typically has a nominal width of about 0.13 mm to about 15.0 mm (e.g., about 1.30 mm). The working channel 814 typically has an internal diameter of about 0.50 mm to about 20.00 mm (e.g., about 1.85 mm) and a wall thickness of about 0.13 mm to about 2.00 mm (e.g., about 0.36 mm). A beveled edge 818 of the working channel 814 is typically oriented at an angle of about 5° to about 80° (e.g., about 35°) from a central axis of the elongate shaft 802.

Tabs 824 of the handle portion 804 typically have a width of about 5.0 mm to about 9.5 mm (e.g., about 6.4 mm), a thickness of about 1.0 mm to about 3.4 mm (e.g., about 2.3 mm), and a length (measured from the exterior opening 810 to ends of the tabs 824) of about 5.0 mm to about 17.1 mm (e.g., about 11.4 mm). The tabs 824 extend from the elongate shaft 802 at an angle of about 5° to about 90° (e.g., about 13°) with respect to the central axis of the elongate shaft 802.

The wall portions 808 of the outer guide 860 typically have a length of about 50.0 mm to about 177.2 mm (e.g., about 118.1 mm) and a wall thickness of about 0.12 mm to about 0.76 mm (e.g., about 0.38 mm). The support 876 typically has a length of about 2.00 mm to about 7.62 mm (e.g., about 5.08 mm), a wall thickness of about 0.12 mm to about 0.57 mm (e.g., about 0.38 mm), and an internal radius of about 0.5 mm to about 4.5 mm (e.g., about 3.0 mm). The exterior opening 870 of outer guide 860 typically has a nominal width that is about equal to the nominal width of the exterior opening 810 of the inner cannula 850. The tabs 884 of the handle portion 864 typically have a width of about 5.0 mm to about 28.6 mm (e.g., about 19.1 mm), a thickness of about 1.0 mm to about 3.8 mm (e.g., about 2.5 mm), and a length (measured from the exterior opening 870 to ends of the tabs 864) of about 5.0 mm to about 15.3 mm (e.g., about 10.2 mm). The tabs 864 are oriented at an angle that is about equal to the angle at which the tabs 824 are oriented with respect to the central axis of the elongate shaft 802. The recesses 842 of the tabs 864 typically have a length of about 0.5 mm to about 18.8 mm (e.g., about 12.5 mm), a depth of about 0.05 mm to about 2.60 mm (e.g., about 1.73 mm), and a width of about 3.0 mm to about 11.4 mm (e.g., about 7.6 mm).

The inner cannula 850 and the outer guide 860 of the operative cannula 800 may be manufactured via the one or more techniques indicated above with respect to the elongate shaft 102 of the operative cannula 100 and may have a material formulation as described above with respect to a material formulation of the operative cannula 100. Such materials typically have a hardness in a range of about 0 Shore A to about 100 Shore A.

A clinician can use the operative cannula 800 to perform an intervention within a uterine cavity of a patient to further examine, treat, remove, or manipulate an abnormality, an anatomical feature of interest, a healthy tissue, a foreign body, or a misplaced device. For example, as described above with respect to the operative cannula 100 and with respect to FIG. 5, a clinician uses a handset attached to the endoscopic cannula 101 to insert the endoscopic cannula 101 into a cervix 109 of the patient. The clinician advances the endoscopic cannula 101 distally until the distal portion 105 of the endoscopic cannula 101 is positioned at a desired location and at a desired orientation within a uterine cavity 111 of the patient.

Upon viewing an abnormality 113 via a video stream or via one or more images captured by the endoscopic cannula 101 (displayed on a monitor of the handset) and deciding to perform an operation (e.g., a biopsy procedure, a polypectomy, an excision, or a cautery) within the uterine cavity 111 to further examine or to treat the abnormality 113, the clinician attaches (e.g., clips) the operative cannula 800 to the proximal portion 103 of the endoscopic cannula 101 that is disposed within the vaginal canal 119 or disposed external to the patient, as described above with respect to the operative cannula 100 and with respect to FIG. 6. With the outer guide 860 of the operative cannula 800 attached to the proximal portion 103 of the endoscopic cannula 101, the clinician slides the inner cannula 850 distally until the handle portion 804 of the inner cannula 850 abuts the channel support 876 of the outer guide 860 to position the inner cannula 850 within the uterine cavity 111, as described above with respect to the operative cannula 100 and with respect to FIG. 7.

The clinician then inserts a surgical instrument 117 into a proximal opening 836 of the working channel 814 and slides the surgical instrument 117 distally within the working channel 814 until the surgical instrument 117 exits a distal opening 836 of the working channel 814, as described above with respect to the operative cannula 100 and with respect to FIG. 8. The clinician manipulates the surgical instrument 117 to perform the operation within the uterine cavity 111. Upon completion of the operation, the clinician withdraws the surgical instrument 117 from the working channel 814 through the proximal opening 836 of the working channel 814, as described above with respect to the operative cannula 100 and with respect to FIG. 9. Once the surgical instrument 117 has been removed from the working channel 814, the clinician retracts the inner cannula 850 and then removes (e.g., pulls) the operative cannula 800 from the endoscopic cannula 101 so that the endoscopic cannula 101 can be used to make additional observations of the uterine cavity 111 (as described above with respect to the operative cannula 100 and with respect to FIG. 10). Following the operation, the operative cannula 800 can be disposed of according to standard protocols.

In some instances, upon performing the operation and withdrawing the surgical instrument 117 from the working channel 814, the clinician withdraws the operative cannula 800 and endoscopic cannula 101 from the cervix 109 while the operative cannula 800 is still attached to the endoscopic cannula 101. In other instances, upon performing the operation, the clinician withdraws the operative cannula 800, the endoscopic cannula 101 (e.g., carrying the operative cannula 800), and the surgical instrument 117 from the cervix 109 while the surgical instrument 117 is still disposed within the working channel 814, as described above with respect to the operative cannula 100.

In some cases, the operative cannula 800 may be used in a procedure for removing a foreign body or for retrieving a misplaced device (e.g., for passing an instrument within the working channel 814 that can be used to remove the foreign body or to retrieve the device) from the uterine cavity 111, as described above with respect to the operative cannula 100.

The operative cannula 800 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 800 can enable procedures that would otherwise be performed in a hospital to be performed in a physician's office or in a clinic, as discussed above with respect to the operative cannula 100. The operative cannula 800 can be packaged individually, and both the operative cannula 800 and the packaging will remain sterile for a shelf-life of the operative cannula 800.

Figure 28:
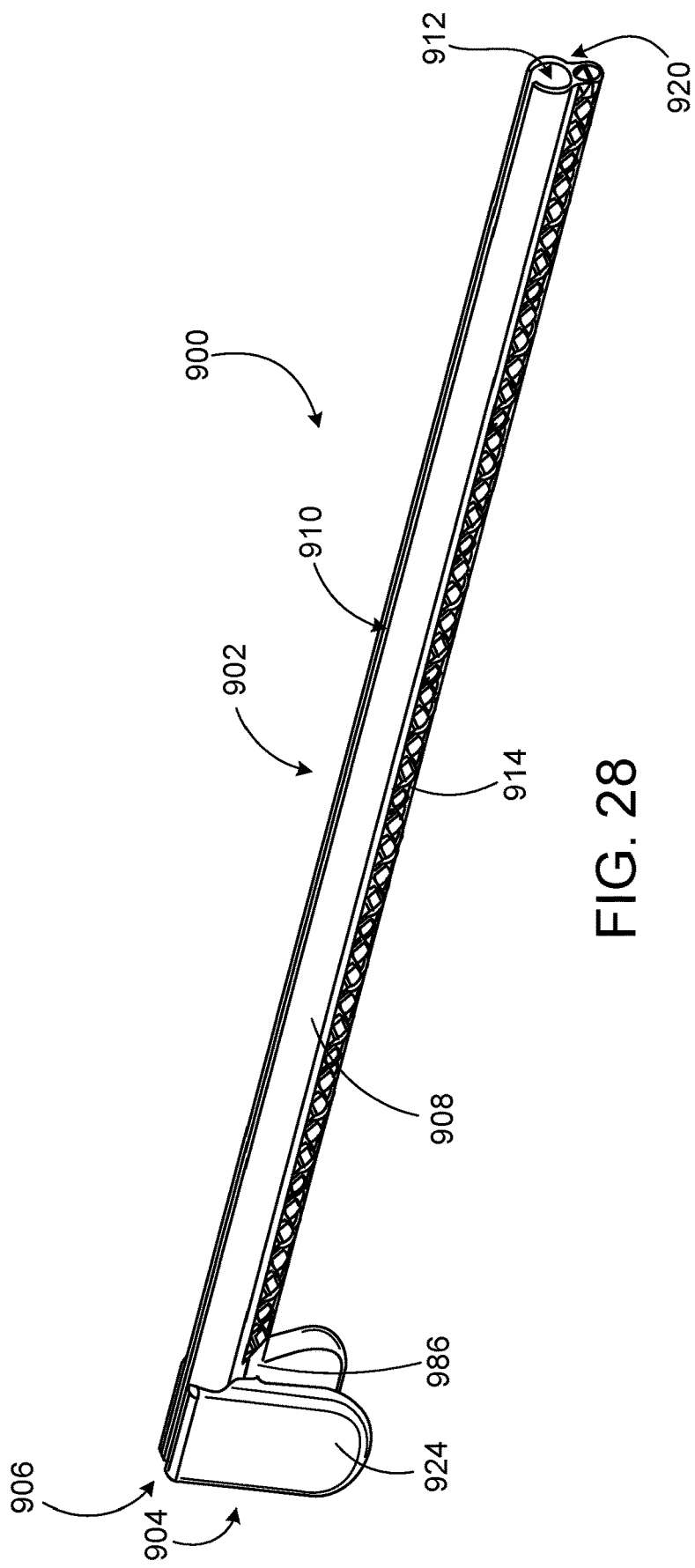
FIG. 28 is a perspective view of an operative cannula that includes a fabric working channel.
Figure 29:
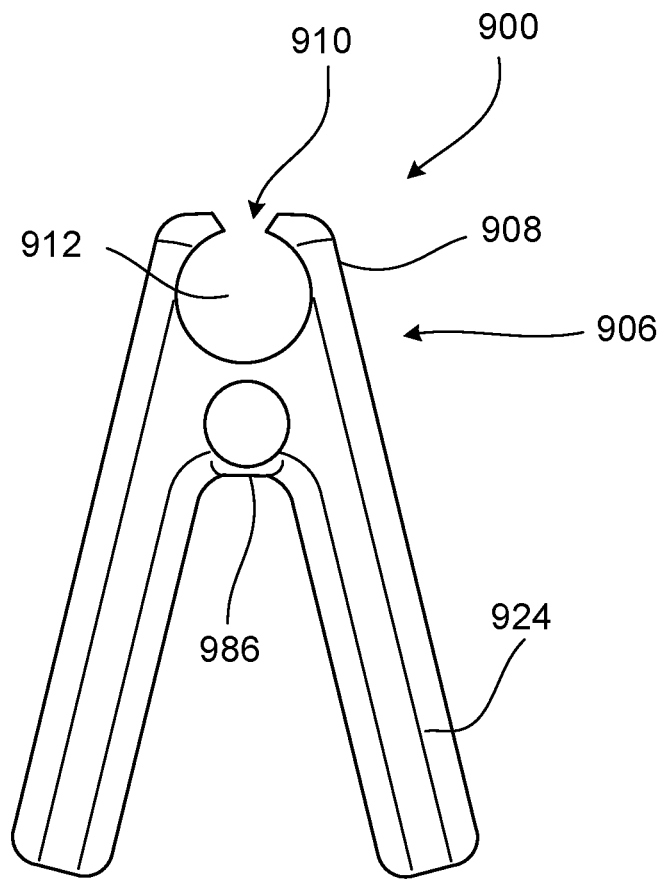
FIG. 29 is an end view of the operative cannula of FIG. 28.

While the operative cannulas 100, 200, 300, 400, 500, 600, 700, 800 have been described and illustrated as including plastic or molded (e.g., rigid) working channels 114, 214, 314, 414, 514, 614, 714, 814, in some embodiments, an operative cannula includes a fabric working channel that is radially collapsible and expandable. For example, FIGS. 28 and 29 illustrate an operative cannula 900 that includes such a working channel. Like the operative cannulas 100, 200, 300, 400, 500, 600, 700, 800, the operative cannula 900 is a disposable device that is configured to allow passage of a surgical instrument along the endoscopic cannula 101 (shown in FIG. 1) and into a uterine cavity for performing an intervention within the uterine cavity. The operative cannula 900 is configured to be attached to (e.g., clipped onto) the endoscopic cannula 101 and can be slid between the proximal portion 103 of the endoscopic cannula 101 and the distal portion 105 of the endoscopic cannula 101. Example interventions that can be performed using the operative cannula 900 include device retrievals, operative procedures (e.g., surgical procedures), and other procedures.

The operative cannula 900 includes an elongate shaft 902 that is substantially similar in construction and function to the elongate shaft 102 of the operative cannula 100, except that the elongate shaft 902 does not include an elongate interior opening (such as the interior opening 116). Accordingly, a structure and material choice of the elongate shaft 902 provide the elongate shaft 902 with a flexibility that allows wall portions 908 of the elongate shaft 902 to spread apart (e.g., to be forced or pulled apart) to allow passage of the endoscopic cannula 101 through an exterior opening 910 and into an interior pocket 912 of the elongate shaft 902. Therefore, the operative cannula 900 can be attached to (e.g., clipped onto) the endoscopic cannula 101 by aligning the endoscopic cannula 101 parallel to the elongate shaft 902 and pressing the endoscopic cannula 101 against the exterior opening 910 of the elongate shaft 902 until the endoscopic cannula 101 forces the wall portions 908 apart and snaps into the interior pocket 912 of the elongate shaft 902. In this manner, the operative cannula 900 can be easily clipped onto the endoscopic cannula 101.

The elongate shaft 902 is short enough in length to allow the operative cannula 900 to be clipped onto the proximal portion 103 of the endoscopic cannula 101 without having to remove (e.g., withdraw) the endoscopic cannula 101 from the patient during a procedure. In some examples, the operative cannula 900 may be attached to the endoscopic cannula 101 by sliding the distal portion 105 of the endoscopic cannula 101 into the interior pocket 912 of the elongate shaft 902 from a proximal end 906 of the elongate shaft 102.

Due to the flexibility and a softness of the elongate shaft 902, the elongate shaft 902 is able to elastically (e.g., reversibly) deform (e.g., bend) to follow a nominal shape (e.g., a nominal curvature) of the endoscopic cannula 101 as the operative cannula 900 is slid along the endoscopic cannula 101. For example, as the operative cannula 900 is slid distally from the proximal portion 103 of the endoscopic cannula 101, the elongate shaft 902 can deform to follow the curve 107 in the endoscopic cannula 101. As the operative cannula 900 is slid proximally from the distal portion 105 of the endoscopic cannula 101, the elongate shaft 902 can regain its nominal, straight shape. Accordingly, the operative cannula 900 can advantageously be used with endoscopic cannulas having a variety of curvature profiles.

The operative cannula 900 also includes a handle portion 904 (e.g., a gripping member) that extends from the proximal end 906 of the elongate shaft 902 and that is substantially similar in construction and function to the handle portion 104 of the operative cannula 100. Accordingly, tabs 924 of the handle portion 904 can be urged (e.g., squeezed or pinched) together to pull the wall portions 908 apart to widen the opening 910 of the elongate shaft 902 to facilitate entry of the endoscopic cannula 101 into the interior pocket 912 of the operative cannula 900 or to facilitate exit of endoscopic cannula 101 from the interior pocket 912 of the operative cannula 900. A user can urge the tabs 924 together to widen the operative cannula 900 near the proximal end 906 of the elongate shaft 902 and then place the widened, proximal portion of the operative cannula 900 around the endoscopic cannula 101. From an urged position, the tabs 924 can be released to allow the wall portions 908 to approach each other around the endoscopic cannula 101 to facilitate attachment of the operative cannula 900 to the endoscopic cannula 101. With the proximal portion of the operative cannula 900 attached to the endoscopic cannula 101, the user can use his or her fingers to guide a remaining portion of the operative cannula 900 onto the endoscopic cannula 101.

Still referring to FIGS. 28 and 29, the elongate shaft 902 further includes a working channel 914 extending along the wall portions 908. The working channel 914 includes a rigid section 986 (e.g., a plastic or molded section) that is positioned at the proximal end 106 of the elongate shaft 902 and that extends between the tabs 924 of the handle portion 904. The working channel 914 also includes a fabric section 988 that extends from the rigid section 986 to a distal end 920 of the elongate shaft 902. The working channel 914 is sized to allow passage of surgical instruments (e.g., surgical forceps, biopsy punches, surgical scissors, polyp snares, biopsy forceps, grasping forceps, bipolar electrodes, and cytology brushes) for carrying out an intervention (e.g., operation or another procedure) within a body cavity of the patient.

A user can introduce a surgical instrument into the rigid section 986 of the working channel 914, which guides the surgical instrument into the fabric section 988 of the working channel 914 as the user moves the surgical instrument distally within the working channel 914. The fabric section 988 of the working channel 914 may be formed as a mesh of woven fabric, knitted fabric, braided fabric, or fabric with another type or structure or pattern.

The fabric section 988 of the working channel 914 is expandable from a collapsed (e.g., nominal) state in which a surgical instrument is not disposed in the working channel 914 to an expanded (e.g., working) state in which a surgical instrument is disposed within the working channel 914. That is, as a surgical instrument is passed into the working channel 914, the fabric section 988 of the working channel 914 expands radially around the surgical instrument. The fabric section 988 of the working channel 914 can have a reduced, collapsed width that minimizes patient discomfort during insertion of the operative cannula 900 into the patient, while having the capability to expand to accommodate surgical instruments of various widths or diameters to perform an intervention within the body cavity of the patient.

In some embodiments, the operative cannula 900 includes a locking feature (e.g., provided by one or more detents, recesses, or other physical stops) positioned near the distal end 920 of the elongate shaft 902 that can mate with a corresponding locking feature positioned along the distal portion 105 of the endoscopic cannula 101 to secure the operative cannula 900 in place along the distal portion 105 of the endoscopic cannula 101 (e.g., to prevent the operative cannula 900 from sliding distally off of the endoscopic cannula 101). In some embodiments, the locking feature may be located along a central or other portion of the elongate shaft 902 to mate with a corresponding locking feature positioned along a central or other portion of the endoscopic cannula 101.

The elongate shaft 902 of the operative cannula 900 typically has a length and a wall thickness that are about equal to the length and the wall thickness of the elongate shaft 102 of the operative cannula 100. The interior pocket 912 typically has a diameter that is about equal to the diameter of the interior pocket 112 of the operative cannula 100. The working channel 914 typically has a wall thickness of about 0.025 mm to about 2.030 mm (e.g., about 0.130 mm). In an expanded state, the working channel 914 typically has an internal diameter of about 0.5 mm to about 5.0 mm (e.g., about 1.8 mm). The tabs 924 typically have a width, a length, and a thickness that are about equal to the width, the length, and the thickness of the tabs 124 of the operative cannula 100. The tabs 924 extend from the elongate shaft 902 at an angle of about 5° to about 90° (e.g., about 13°) with respect to a central axis of the elongate shaft 902.

A body of the operative cannula 900 (e.g., including the wall portions 908, the handle portion 904, and the rigid section 986 of the working channel 914) may be manufactured via one or more techniques including injection molding, extrusion, casting, machining, SLA, and FDM. The body of the operative cannula 900 is typically made of one or materials that are relatively soft and/or that have a relatively high elasticity, such as polypropylene, nylon, PTFE, silicone, latex rubber, ABS, polycarbonate, polystyrene, and PEBA. Such materials typically have a hardness in a range of about 0 Shore A to about 100 Shore A. The wall portions 908, the handle portion 904, and the rigid section 986 of the working channel 914 may be made of the same one or more materials or made of different, respective materials. The fabric section 988 of the working channel 914 is typically made of a medical grade yarn formed of one or more materials such as flashspun high-density polyethylene fibers, PTFE membranes, polyethylene terephthalate (PET), polypropylene/polyglycolic acid (PGA), polypropylene/polylactic acid (PLA), polyester/nitinol, or other multifilament or monofilament polyester fibers.

A clinician can use the operative cannula 900 to perform an intervention within a uterine cavity of a patient to further examine, treat, remove, or manipulate an abnormality, an anatomical feature of interest, a healthy tissue, a foreign body, or a misplaced device according to the steps described above with respect to the operative cannula 100 and with respect to FIGS. 5-10, except that a surgical instrument is inserted directly into the working channel 914 instead of being inserted into an entry port (such as the entry port 122). The operative cannula 900 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 900 can enable procedures that would otherwise be performed in a hospital to be performed in a physician's office or in a clinic, as discussed above with respect to the operative cannula 100.

Figure 32:
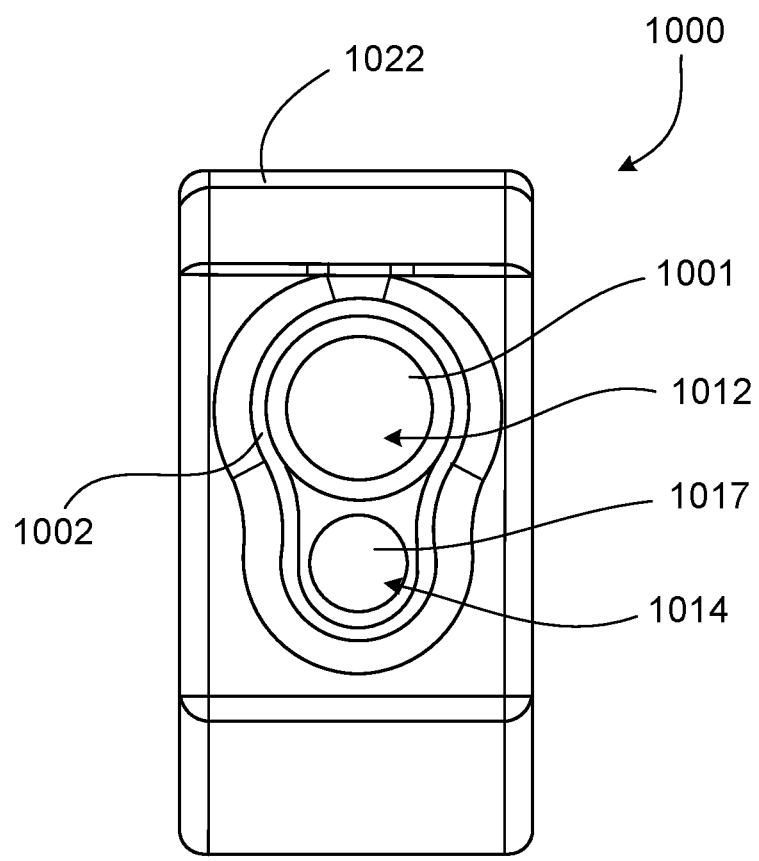
FIG. 32 is a cross-sectional view of a proximal portion of the operative cannula of FIGS. 30 and 31, mounted to the endoscopic cannula of FIG. 31.

While the operative cannulas 100, 200, 300, 400, 500, 600, 700, 800, 900 have been described and illustrated as including elongate shafts 102, 202, 302, 402, 502, 602, 702, 802, 902 with rigid portions, in some embodiments, an operative cannula includes a fabric elongate shaft that is radially collapsible and expandable. For example, FIGS. 30-32 illustrate an operative cannula 1000 that includes such an elongate shaft. Like the operative cannulas 100, 200, 300, 400, 500, 600, 700, 800, 900, the operative cannula 1000 is a disposable device that is configured to allow passage of a surgical instrument along the endoscopic cannula 101 and into a uterine cavity for performing an intervention within the uterine cavity. The operative cannula 1000 is configured to be slid onto a distal end of an endoscopic cannula, such as an endoscopic cannula 1001. Example interventions that can be performed using the operative cannula 1000 include device retrievals, operative procedures (e.g., surgical procedures), and other procedures.

Referring to FIG. 30, the operative cannula 1000 includes an entry port 1022 and an elongate shaft 1002 that extends distally from the entry port 1002. The elongate shaft 1002 is formed of a braided fabric or woven mesh that radially expands to accommodate the endoscopic cannula 1001 and a surgical instrument as the endoscopic cannula 1001 and the surgical instrument are passed through the elongate shaft 1002. The elongate shaft 1002 defines an interior channel 1008. In a nominal state in which the elongate shaft 1002 is not attached to the endoscopic cannula 1001 and does not carry a surgical instrument, the interior channel 1008 is collapsed to a minimal diameter and has a substantially circular cross-sectional area.

Referring to FIGS. 31 and 32, in a working state in which the elongate shaft 1002 is attached to the endoscopic cannula 1001 and carries a surgical instrument, the interior channel 1008 is expanded to form an interior pocket 1012 that accommodates the endoscopic cannula 1001 and a working channel 1014 that accommodates a surgical instrument 1017. That is, the elongate shaft 1002 can expand to allow passage of surgical instruments (e.g., surgical forceps, biopsy punches, surgical scissors, polyp snares, biopsy forceps, grasping forceps, bipolar electrodes, and cytology brushes) for carrying out an intervention (e.g., a biopsy or another procedure) within the body cavity of the patient. The elongate shaft 1002 can expand and collapse to snuggly accommodate a surgical instrument 1017 according to a size (e.g., a width or a diameter) of a surgical instrument 1017. While the operative cannula 1000 is shown mounted to the straight endoscopic cannula 1001 in the example of FIG. 31, the elongate shaft 1002 of the operative cannula 1000 is sufficiently soft and flexible to elastically (e.g., reversibly) deform (e.g., bend) to follow a shape of a curved endoscopic cannula (e.g., the endoscopic cannula 101) as the operative cannula 1000 is slid onto the endoscopic cannula. A smoothness of the elongate shaft 1002 can also ease insertion of the operative cannula 1000 through a cervix of the patient, thereby minimizing patient discomfort during use of the operative cannula 1000.

The entry port 1022 of the operative cannula 1000 includes a primary opening 1026 that is parallel to and leads to the interior channel 1008 of the elongate shaft 1022 and a secondary opening 1036 that is orientated at an angle to and leads to the interior channel 1008 of the elongate shaft 1022. As the distal end of the endoscopic cannula 1001 is inserted into the primary opening 1026 of the entry port 1022 and slid distally, the elongate shaft 1002 expands radially to form the interior pocket 1012 around the endoscopic cannula 101. Once the operative cannula 1000 is mounted to the endoscopic cannula 1001, and as the surgical instrument 1017 is inserted into the secondary opening 1036 of the entry port 1022 and slid distally, the elongate shaft 1002 expands radially to form the working channel 1014 around the surgical instrument 1017. The elongate shaft 1002 can have a minimized width that minimizes patient discomfort during insertion of the operative cannula 1000 (e.g., mounted to the endoscopic cannula 1001) into the patient, while having the capability to expand to accommodate a surgical instrument 1017 that is passed into the elongate shaft 1002 to perform an intervention within a body cavity of the patient.

In some embodiments, the operative cannula 1000 includes a locking feature (e.g., provided by one or more detents, recesses, or other physical stops) positioned near a distal end 1020 of the elongate shaft 1002 that can mate with a corresponding locking feature positioned along a distal portion of an endoscopic cannula to secure the operative cannula 1000 in place along the distal portion of the endoscopic cannula (e.g., to prevent the operative cannula 1000 from sliding distally off of the endoscopic cannula). In some embodiments, the locking feature may be located along a central or other portion of the elongate shaft 1002 to mate with a corresponding locking feature positioned along a central or other portion of the endoscopic cannula.

The elongate shaft 1002 of the operative cannula 1000 has a length that can extend along a majority or all of the length of the endoscopic cannula 1001 and is typically about 127.0 mm to about 457.2 mm (e.g., about 304.8 mm). In some examples, the length of the elongate shaft 1002 is about equal to the length of an endoscopic cannula with which the operative cannula 1000 is used. The elongate shaft 1002 typically has a wall thickness of about 0.026 mm to about 2.030 mm (e.g., about 0.130 mm). In a nominal state, the interior channel 1008 typically has a diameter of about 1.3 mm to about 7.5 mm (e.g., about 2.5 mm). In a working state, the interior pocket 1012 typically has a diameter of about 2.5 mm to about 15.0 mm (e.g., about 5.0 mm), and the working channel 1014 typically has a diameter of about 0.5 mm to about 5.0 mm (e.g., about 1.8 mm). The primary opening 1026 of the entry port 1022 typically has a diameter of about 2.5 mm to about 15.0 mm (e.g., about 5.0 mm) and a length of about 6.35 mm to about 38.10 mm (e.g., about 12.70 mm). The secondary opening 1036 of the entry port 1022 typically has a diameter of about 1.5 mm to about 15.0 mm (e.g., about 5.0 mm) and a length of about 6.35 mm to about 38.10 mm (e.g., about 12.70 mm). The secondary opening 1036 typically extends at an angle of about 5° to about 170° (e.g., about 45°) from a central axis of the elongate shaft 1022.

The entry port 1022 of the operative cannula 1000 may be manufactured via one or more techniques including injection molding, extrusion, casting, machining, SLA, and FDM. Example materials from which the entry port 1022 is typically made include metals (e.g., aluminum or steel) and plastics (e.g., polycarbonate or polyethylene). The elongate shaft 1002 of the operative cannula 1000 is typically made of a medical grade yarn formed of one or more materials such as flashspun high-density polyethylene fibers, PTFE membranes, polyethylene terephthalate (PET), polypropylene/polyglycolic acid (PGA), polypropylene/polylactic acid (PLA), polyester/nitinol, and other multifilament or monofilament polyester fibers.

A clinician can use the operative cannula 1000 to perform an intervention within a uterine cavity of a patient to further examine, treat, remove, or manipulate an abnormality, an anatomical feature of interest, a healthy tissue, a foreign body, or a misplaced device. For example, as described above with respect to the operative cannula 100, the endoscopic cannula 101, and with respect to FIG. 5, a clinician uses a handset attached to an endoscopic cannula to insert the endoscopic cannula into a cervix 109 of the patient. The clinician advances the endoscopic cannula distally until a distal portion of the endoscopic cannula is positioned at a desired location and at a desired orientation within a uterine cavity 111 of the patient.

Upon viewing an abnormality 113 via a video stream or via one or more images captured by the endoscopic cannula (displayed on a monitor of the handset) and deciding to perform an operation (e.g., a biopsy procedure, a polypectomy, an excision, or a cautery) within the uterine cavity 111 to further examine or to treat the abnormality 113, the clinician withdraws the endoscopic cannula 101 from the patient. The clinician slides the operative cannula 1000 onto the endoscopic cannula. With the operative cannula 1000 mounted to the endoscopic cannula, the clinician reinserts the endoscopic cannula into the cervix 109 of the patient and advances the endoscopic cannula distally until the distal portion of the endoscopic cannula is positioned at a desired location and at a desired orientation within the uterine cavity 111 according to a location of the abnormality 113.

The clinician then inserts a surgical instrument 1017 into the secondary opening 1036 of the entry port 1022 and slides the surgical instrument 1017 distally (i.e., defining the working channel 1014 within the elongate shaft 1022) until the surgical instrument 1017 exits the distal end 1020 of the elongate shaft 1002, as described above with respect to the operative cannula 100 and with respect to FIG. 8. The clinician manipulates the surgical instrument 1017 to perform the operation within the uterine cavity 111. Upon completion of the operation, the clinician withdraws the surgical instrument 1017 from the elongate shaft 1002, as described above with respect to the operative cannula 100 and with respect to FIG. 9. The clinician may then make additional observations of the uterine cavity 111 with the operative cannula 1000 attached to the endoscopic cannula (as described above with respect to the operative cannula 100 and with respect to FIG. 10).

Upon completion of the operation and with the operative cannula 1000 attached to the endoscopic cannula, the clinician withdraws the endoscopic cannula from the cervix 109 of the patient. The operative cannula 1000 and the endoscopic cannula are then disposed of according to standard protocols. In some instances, upon performing the operation, the clinician withdraws the endoscopic cannula (e.g., carrying the operative cannula 1000) and the surgical instrument 1017 from the cervix 109 while the surgical instrument 1017 is still disposed within the working channel 1014 of the elongate shaft 1002, as described above with respect to the operative cannula 100.

In some cases, the operative cannula 1000 may be used in a procedure for removing a foreign body or for retrieving a misplaced device (e.g., for passing an instrument within the working channel 1014 that can be used to remove the foreign body or to retrieve the device) from the uterine cavity 111, as described above with respect to the operative cannula 100.

The operative cannula 1000 provides a low-cost, safe alternative to an endoscopic cannula with an integrated working channel and provides a low-cost, safe operative capability to an endoscope that does not have an operative capability, as discussed above with respect to the operative cannula 100. Furthermore, the operative cannula 1000 can enable procedures that would otherwise be performed in a hospital to be performed in a physician's office or in a clinic, as discussed above with respect to the operative cannula 900.

While the operative cannulas 100, 200, 300, 400, 800, 900 have been described as including the handle portions 104, 204, 304, 404, 804, 864, 904 that have tabs that can be squeezed together by a user to widen the exterior openings 110, 210, 310, 810, 807, 910 to the interior pockets 112, 212, 312, 812, 912 or to form an opening in the coiled wall 408 to provide access to the interior pocket 412, other mechanisms or techniques for widening or creating such openings can be used. For example, a tool spreading device (e.g., a device similar to a shoehorn or another type of tool spreading device) may be used to widen the exterior openings 110, 210, 310, 810, 870, 910 to the interior pockets 112, 212, 312, 812, 912 or to form an opening in the coiled wall 408 to provide access to the interior pocket 412.

While the operative cannulas 100, 200, 300, 400, 500, 600, 700, 800, 900, 1000 have been described as being used with hysteroscopes, they can alternatively or additionally be used with any of various other types of endoscopes, such as cystoscopes, laryngoscopes, ureteroscopes, and laparoscopes. Similarly, while the operative cannulas 100, 200, 300, 400, 500, 600, 700, 800, 900, 1000 have been described as being used to enable operative procedures to be performed within uterine cavities of patients, the operative cannulas 100, 200, 300, 400, 500, 600, 700, 800, 900, 1000 can alternatively or additionally be used to enable operative procedures to be performed in other body cavities, such as a ureter, a bladder, an esophagus, or an abdominal cavity.

While the operative cannulas 100, 200, 300, 400, 500, 600, 700, 800, 900, 1000 have been described as including the working channels 114, 214, 314, 414, 514, 614, 714, 814, 914, 1014 as extending from proximal ends of the elongate shafts 102, 202, 302, 402, 502, 602, 702, 802, 902, 1002 to distal ends of the elongate shafts 102, 202, 302, 402, 502, 602, 702, 802, 902, 1002 other embodiments are possible. For example, in some embodiments, an operative cannula may include a working channel that does not extend all the way to a proximal end or all the way to a distal end of an elongate shaft of the operative cannula.

While the operative cannulas 100, 200, 300, 400, 500, 600, 800 have been described as including the working channels 114, 214, 314, 414, 514, 614, 814 that have beveled distal ends, other embodiments are possible. For example, in some embodiments, an operative cannula may include a working channel that does not have a beveled distal end and that therefore has a cylindrical shape (e.g., a circular cross section) along an entire length of the working channel.

While the operative cannulas 100, 200, 300, 400, 600, 800 have been described and illustrated as including the working channels 114, 214, 314, 414, 614, 814 with a predetermined shape, other embodiments are possible. For example, in some embodiments, an operative cannula may include a coiled working channel that can expand from a nominal state to accommodate a size of a surgical instrument as the surgical instrument is introduced into the working channel and slid within the working channel. Such working channels may have a nominal diameter that is smaller than a diameter of the working channels 114, 214, 314, 414, 614, 814 and may accordingly result in less discomfort to the patient while the operative cannula is disposed within the cervix of the patient.

While the operative cannulas 100, 200, 300, 400 have been described as including the entry ports 122, 222, 322, 422 that extend laterally from the elongate shafts 102, 202, 302, 402 of operative cannulas 100, 200, 300, 400, in some embodiments, an operative cannula alternatively includes an entry port that extends from a hole (e.g., leading to a working channel of the operative cannula) near a proximal end of an elongate shaft of the operative cannula.

While the operative cannulas 100, 200, 300, 400 have been described as including the entry ports 122, 222, 322, 422, other embodiments are possible. For example, in some embodiments, an operative cannula (e.g., including any of the elongate shafts 102, 202, 302, 402 and the any of the handle portions 104, 204, 304, 404) may not include an entry port. In such cases, a surgical instrument may be introduced into a working channel of the operative cannula at an accessible, proximal end of the working channel near a proximal end of an elongate shaft of the operative cannula. In some examples, a handle portion of the operative cannula may serve as a back-stop that locates the external orifice of the cervix if the handle portion abuts the cervix as the elongate shaft of the operative cannula is inserted into the cervix.

In some embodiments, an operative cannula that is substantially similar in structure and function to any of the operative cannulas 100, 200, 300, 400, 800, 900 can include one or more ring-like structures (e.g., arc-shaped members) that are positioned along one or more walls of an elongate shaft of the operative cannula near a distal end of the elongate shafts. The ring-like structure provides additional rigidity (e.g., stiffness) to the distal portion of the operative cannula to prevent the operative cannula from being easily removed from an endoscopic cannula (e.g., to prevent the operative cannula from being easily widened along an exterior opening while the operative cannula is attached to the endoscopic cannula). In some embodiments, the ring-like structure is a separate component that is attached to (e.g., overmolded into) the elongate shaft of the operative cannula. In some embodiments, the ring-like structure is an integral feature that is formed as a thickened layer of the distal portion of the elongate shaft of the operative cannula. The ring-like structure is typically made of one or more rigid materials, such as spring steel, stainless steel, or aluminum.

While the operative cannulas 100, 200, 300, 400, 500, 600, 700, 800, 900, 1000 have been described as being disposable (e.g., single-use) cannulas, other embodiments are possible. For example, in some embodiments, an operative cannula that is substantially similar in structure to any of the operative cannulas 100, 200, 300, 400, 500, 600, 700, 800, 900, 1000 may be a reusable operative cannula. Such an operative cannula may be made of one or more materials that can withstand decontamination procedures (e.g., autoclave treatments, chemical baths, ethylene oxide (TEO) processing, or irradiation). Example materials include stainless steel and aluminum.

While the operative cannulas 100, 300, 400, 500, 600, 700, 800, 900 have been described as being used with the curved endoscopic cannula 101, in some examples, an operative cannula that is substantially similar in structure to any of the operative cannulas 100, 300, 400, 500, 600, 700, 800, 900 can made of one or more materials that have a relatively high or low elasticity and a relatively high or low hardness. Such an operative cannula can be used with (e.g., secured to) a straight endoscopic cannula and pass relatively flexible surgical instruments or relatively rigid surgical instruments. In some embodiments, such an operative cannula may include an elongate shaft with a material formulation that typically has a hardness in a range of about 5 Shore D to about 95 Shore D.

While the operative cannulas 100, 200, 300, 400, 800, 900 have been described as being attachable to an endoscopic cannula via a clipping action, other attachment techniques are possible. For example, in some cases, the operative cannulas 100, 200, 300, 400, 800, 900 may be attached to an endoscopic cannula by sliding a distal portion of the endoscopic cannula into the interior pockets 112, 212, 312, 412, 812, 912 of the elongate shafts 102, 202, 302, 402, 802, 902 from proximal ends of the elongate shafts 102, 202, 302, 402, 802, 902.

While the operative cannula 800 has been described as a one-stage telescopic device, in some embodiments, an operative cannula can be configured as a two-stage or multiple-stage telescopic device that includes two or more defined extended configurations that result from mating or complementing features (e.g., detents, recesses, or other physical stops) located along an inner cannula and an outer guide of the operative cannula.

While the sheaths 534, 734 have been described as components of the operative cannulas 500, 700, in some embodiments, the sheaths 534, 734 can be provided as separate components that can be attached to (e.g., slid onto) an elongate body of an operative cannula. For example, a user of the operative cannula can slide a sheath 534, 734 onto a distal end of the elongate body and move the sheath 534, 734 proximally until the sheath 534, 734 is in contact with the elongate body of the operative cannula along an entire length of the sheath 534, 734.

While the operative cannula 1000 is described as being slid onto an endoscopic cannula during use, in some embodiments, the operative cannula 1000 is preloaded onto the endoscopic cannula such both the endoscopic cannula and the operative cannula 1000 can be inserted into a patient in a single step.

Figure 33:
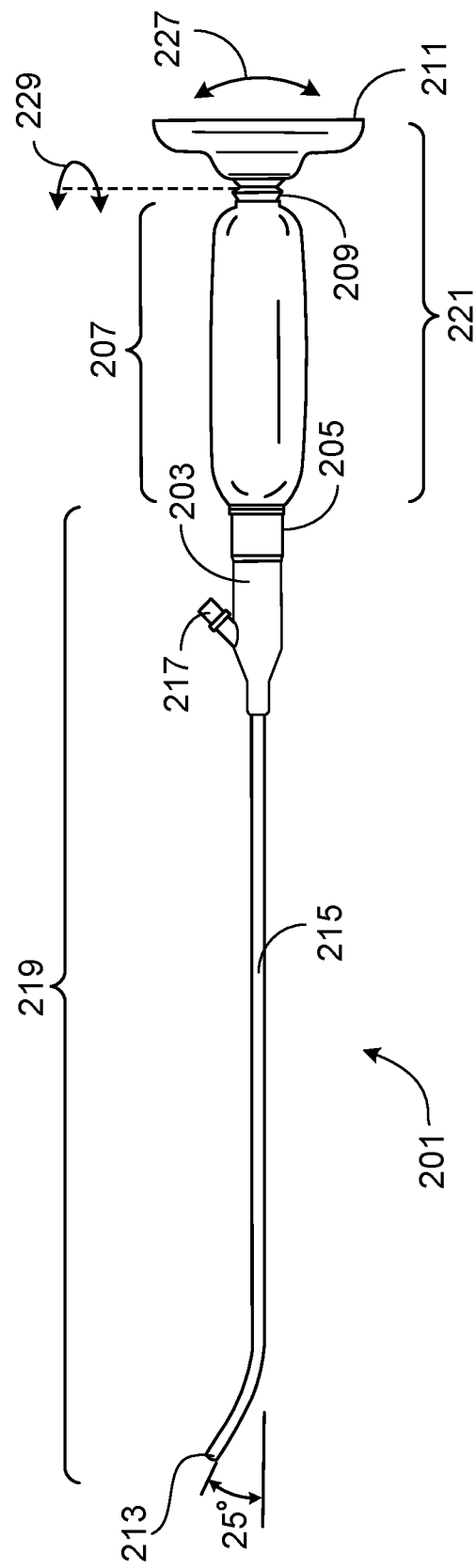
FIG. 33 is a side view of a hysteroscope including the endoscopic cannula of FIG. 1.

In some embodiments, the endoscopic cannula 101 is a component of a hysteroscope. For example, as shown in FIG. 33, a hysteroscope 201 includes the endoscopic cannula 101, a fluid hub 203, a sliding connector 205, a handle body 207, a display mount 211, and a display 213. The endoscopic cannula 101 is made of a distal tip 213 and a shaft 215. The fluid hub 203 includes a fluid port 217, which is configured to deliver fluid into the endoscopic cannula 101 and thus into the uterus. As shown, the shaft 215 is curved near its distal end. The distal tip 213 includes a video camera assembly, lighting elements and fluid ports for in-flow (e.g., out of the hysteroscope 100 and into the patient). According to some embodiments, an outer shell of the distal tip 213 and the shaft 215 are constructed of the same material, for example a heat and UV stabilized nylon 12 grade for tube extrusion such as Grilamid® L25. According to some embodiments the display 211 is a touch-screen display and is able to tilt upwards and downwards (e.g., by about 60 degrees in opposite directions for a total range of motion of 120 degrees) and pivot, or "pan" left and right (e.g., with a total range of motion 90 degrees) as shown by arrows 227 and 229, respectively.

According to some embodiments, the endoscopic cannula 101 (including the camera assembly, LED lighting, and the fluid port 217 integrated into the distal tip 213), the fluid hub 203, and the sliding connector 205 together form a single-use portion 219, which is designed for a single-use. According to these embodiments, the single-use portion 219 is delivered to a medical practitioner in pre-sterilized package and is intended to be disposed of after a single-use. In such embodiments, the handle body 207 and the display 211 form a reusable portion 221, which is designed to be re-used many times.

According to some embodiments, the hysteroscope 100 is a hand-held, compact single-use endoscope. In these cases, the hysteroscope 201 is provided in a sterile package, so is ready for immediate use without requiring any preparation for diagnostic or therapeutic procedures. Such a single-use hysteroscope needs no sophisticated connectors, as that the entire hysteroscope is supplied in a sterile package ready for use.

Figure 34:
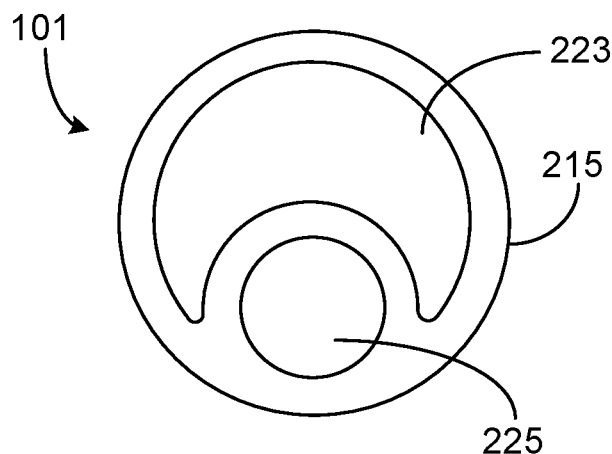
FIG. 34 is a cross-sectional view of the endoscopic cannula of FIG. 1.

FIG. 34 displays a cross-sectional view of the endoscopic cannula 101, which illustrates a first channel 223 that extends from the fluid port 217 and a second channel 225 that can deliver electrical cables to the distal tip 213 of the endoscopic cannula 101. In some examples, introducing an endoscopic cannula (e.g., of a hysteroscope) into the uterus of a patient can be problematic in women that have a tight cervix, such as nulliparous women. For example, a flexible shaft of an endoscopic cannula can be difficult to maneuver laterally in the such a population of women. In this regard, a hysteroscope that is similar in construction and function to the hysteroscope 201 may include an endoscopic cannula with features that can ease the insertion of the endoscopic cannula and improve the maneuverability of the endoscopic cannula as compared to the endoscopic cannula 101.

For example, in some embodiments, a tubing material of an endoscopic cannula is selected as one or more materials with a high durometer (e.g., Polysulfone, Acrylonitrile-Butadiene-Styrene (ABS), Polycarbonate, PEEK, etc.) to aid with ease of insertion and maneuverability of the endoscopic cannula. A higher durometer effectively makes the endoscopic cannula stiffer or less flexible.

Figure 35A:
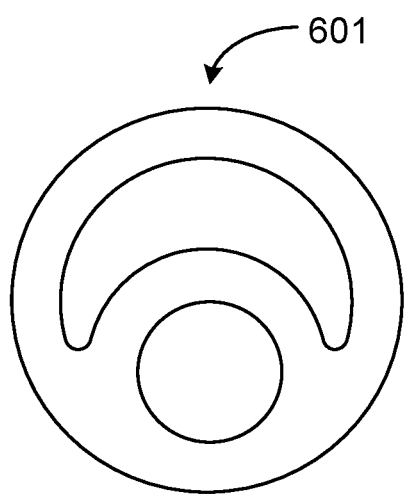
FIGS. 35A-35D are cross-sectional views of endoscopic cannulas with various shaft geometries.
Figure 35B:
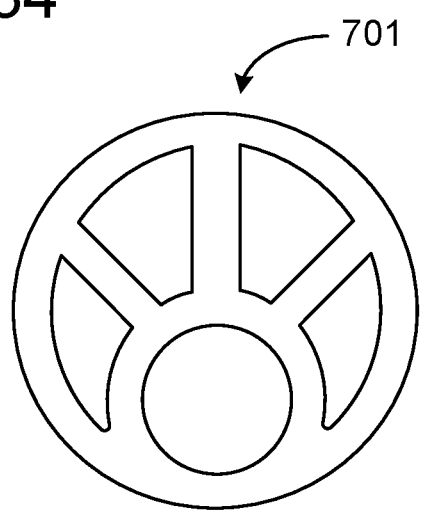
Figure 35C:
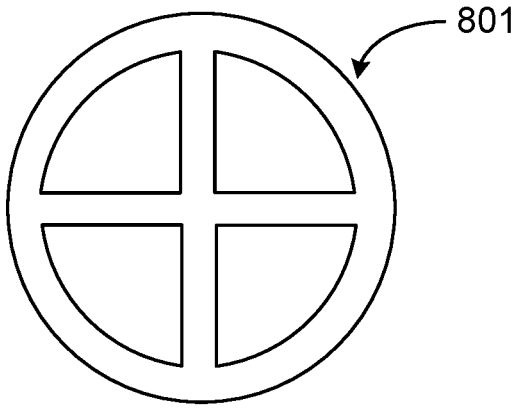
Figure 35D:
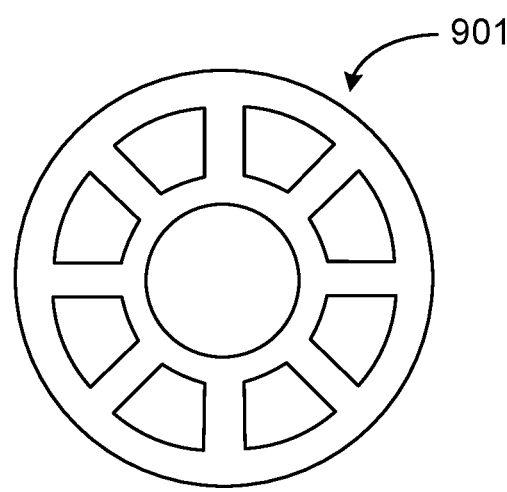

In some embodiments, a stiffness of an endoscopic cannula can be increased by changing the cross-sectional geometry of a shaft of the endoscopic cannula. For example, FIGS. 35A-35D display examples of alternative cross-sectional geometries that can be implemented to increase the stiffness of an endoscopic cannula as compared to the endoscopic cannula 101. Increasing a wall thickness of a shaft (as exemplified by an endoscopic cannula 601 in FIG. 35A) or including additional structures, such as septa (as exemplified by endoscopic cannulas 701, 801, 901 in FIGS. 35B-35D), can increase the stiffness of the endoscopic cannula by providing additional rigidity for insertion and manipulation.

In some embodiments, the stiffness of an endoscopic cannula may be increased by adding a stylet or rod down the tubing of a shaft of the endoscopic cannula. The stylet or rod may be made out of a rigid plastic (e.g., Polysulfone, Acrylonitrile-Butadiene-Styrene (ABS), Polycarbonate, PEEK, etc.) or a metal (e.g., stainless steel, aluminum, titanium, etc.). In some embodiments, such a stylet or rod may be movable proximally and distally along the endoscopic cannula. When the stylet or rod is pushed towards the distal tip of the endoscopic cannula, the stylet or rod forces a bend (e.g., such as the curve 107) near a distal tip of the endoscopic cannula to become straight. The endoscopic cannula can then be inserted in a straight form through the cervix into the uterine cavity. Once in the uterine cavity, the stylet or rod can be pulled back to the proximal end to release the bend at the distal tip back to its angled curvature.

In some embodiments, an overall length of an endoscopic cannula may be reduced by about 3 cm to about 6 cm. Reducing the length of the endoscopic cannula minimizes an associated moment arm and thus reduces the flexibility, thereby increasing an effective stiffness. In some embodiments, such a length reduction can be combined with a material durometer selection, a cross-sectional geometry change, a fixed stylet or rod, or a movable stylet or rod as discussed above to increase the stiffness of an endoscopic cannula.

Figure 36A:
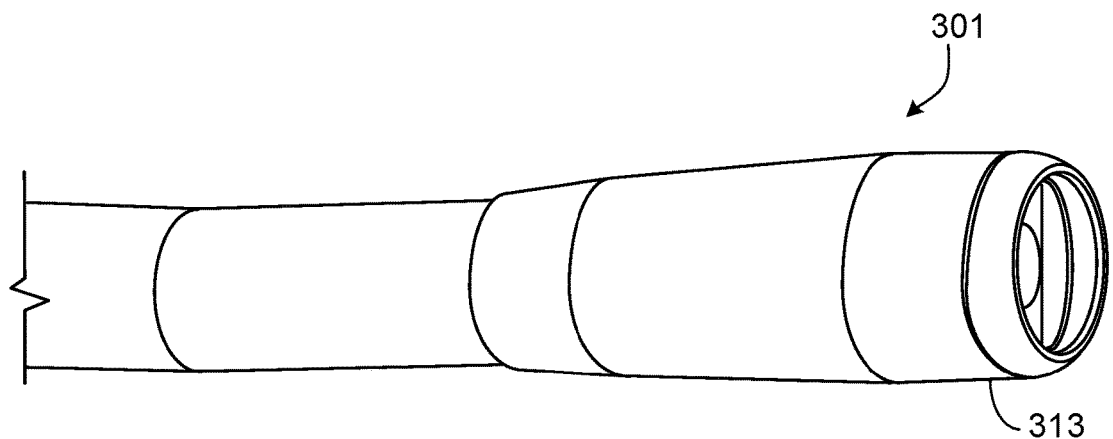
FIGS. 36A-36C are perspective views of end portions of endoscopic cannulas with various distal tip geometries.

In some embodiments, a hysteroscope that is similar in construction and function to the hysteroscope 201 may include an endoscopic cannula that has a distal tip with a shape that is different from that of the distal tip 213 of the endoscopic cannula 101. For example, as shown in FIG. 36A, a distal tip 313 of an endoscopic cannula 301 has a partial dome shape that rounds over a camera housing 327 seated therein. The partial dome shape provides smoother, more rounded edges as compared to the blunt edges of the distal tip 213 of the endoscopic cannula 101, which can help ease insertion of the endoscopic cannula 301. The partial dome-shaped distal tip 313 can still allow saline to pass through a small holes or slits along a frontal portion of the distal tip 313.

Figure 36B:
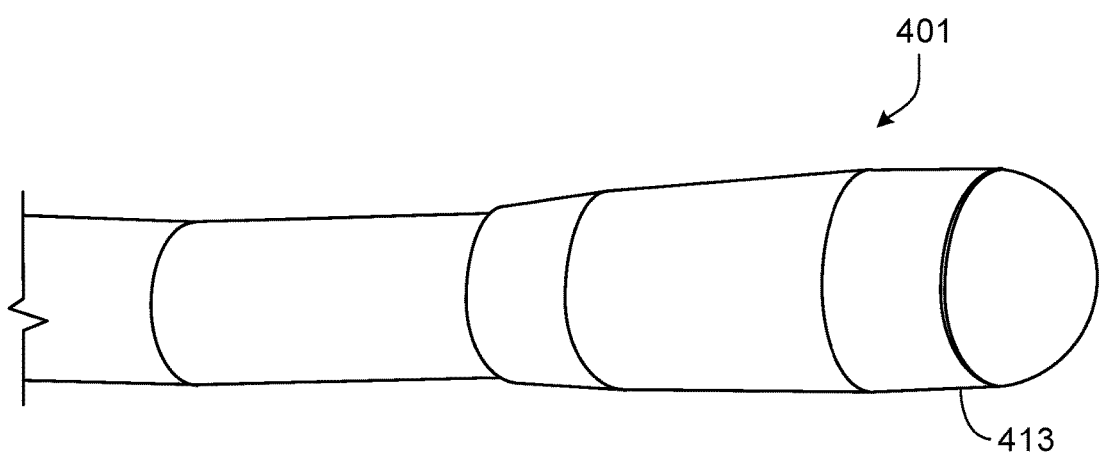
Figure 36C:
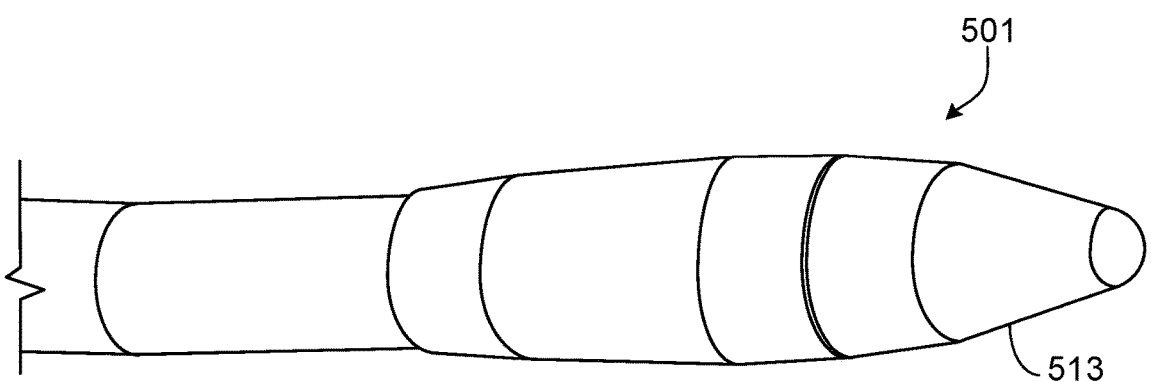

Other distal tip shapes that can similarly provide smoother, more rounded edges for easing insertion of an endoscopic cannula are shown in FIGS. 36B and 36C. For example, FIG. 36B illustrates an endoscopic cannula 401 with a distal tip 413 that has a dome shape, while FIG. 36C illustrates an endoscopic cannula 501 with a distal tip 513 that has a cone shape. As discussed above with respect to the endoscopic cannula 301, the distal tips 413, 513 can ease insertion of the endoscopic cannulas 401, 501 and allow saline to pass through small holes or slits along a frontal portion of the endoscopic cannulas 401, 501.

What is claimed is:

1. An operative cannula, comprising:
   an elongate shaft comprising:
   a first wall structure defining an interior pocket sized to receive a tubular member, the first wall structure being configured to grasp the tubular member when the tubular member is disposed within the interior pocket, the first wall structure comprising two wall portions that define an exterior opening of the elongate shaft, the interior pocket having a distal end formed as a through opening that is centered about a central axis of the first wall structure, and the through opening having a diameter that is at least as large as a diameter of the tubular member when the tubular member is disposed within the interior pocket for allowing movement of a distal end of the tubular member past the distal end of the interior pocket when the tubular member is disposed within the interior pocket, and
   a second wall structure defining a channel, the second wall structure being integral with and directly connected to the first wall structure along a length of the first wall structure, the channel having a maximum width that is smaller than the diameter of the through opening, and the channel being configured to allow passage of an instrument from a proximal end region of the elongate shaft through a distal end region of the elongate shaft; and
   a gripping device for manipulating the elongate shaft, the gripping device comprising two tabular members that extend outward in opposite directions from the proximal end region of the elongate shaft, the two tabular members being accessible and urgable together to widen the exterior opening of the elongate shaft to allow entry of the tubular member into the interior pocket.

2. The operative cannula of claim 1, wherein the exterior opening has a width that is smaller than the diameter of the tubular member and smaller than the diameter of the through opening.

3. The operative cannula of claim 2, wherein the two wall portions are configured to be urged apart to widen the exterior opening.

4. The operative cannula of claim 2, wherein each of the two wall portions defines multiple slots.

5. The operative cannula of claim 1, wherein the elongate shaft is deformable such that the elongate shaft can assume a curvature of the tubular member when the tubular member is disposed within the interior pocket of the elongate shaft and the elongate shaft is moved along the tubular member.

6. The operative cannula of claim 1, wherein the elongate shaft is made of one or more materials having a hardness in a range of about 0 Shore A to about 100 Shore A.

7. The operative cannula of claim 1, wherein the elongate shaft is made of one or more materials having a hardness in a range of about 5 Shore D to about 95 Shore D.

8. The operative cannula of claim 1, wherein the elongate shaft is rigid such that the tubular member assumes a profile of the wall structure of the elongate shaft when the tubular member is disposed within the interior pocket of the elongate shaft and the elongate shaft is moved along the tubular member.

9. The operative cannula of claim 1, wherein the channel comprises a beveled distal end that defines a channel opening.

10. The operative cannula of claim 9, wherein the channel opening has an area that is greater than a cross-sectional area of the channel.

11. The operative cannula of claim 1, wherein the channel is located adjacent to the interior pocket.

12. The operative cannula of claim 1, wherein the gripping device forms a handle of the operative cannula.

13. The operative cannula of claim 12, wherein the two tabular members together form a clip.

14. The operative cannula of claim 1, further comprising an entry port extending laterally from the channel.

15. The operative cannula of claim 1, wherein the elongate shaft is sized to be inserted through a cervix of a patient.

16. The operative cannula of claim 1, wherein the instrument comprises a surgical device.

17. The operative cannula of claim 1, wherein the operative cannula is a single-use device.

18. The operative cannula of claim 1, wherein the operative cannula is configured to facilitate a medical intervention within a body cavity of a patient.

19. The operative cannula of claim 1, wherein the distal end of the tubular member is configured to be positioned within a patient, and wherein the first wall structure is slidable proximally along the tubular member with respect to the distal end of the tubular member when the tubular member is disposed within the interior pocket, such that the proximal end region of the elongate shaft is configured to be positioned outside of the patient while the distal end of the tubular member is disposed within the patient.

20. The operative cannula of claim 1, wherein the diameter of the through opening is equal to a diameter of the interior pocket.

21. The operative cannula of claim 20, wherein the diameter of the interior pocket is centered about the central axis of the first wall structure.

22. The operative cannula of claim 1, wherein the first and second wall structures together define an elongate interior opening therebetween that opens to both the interior pocket and the channel.

* * * * *